United States Patent
Campbell et al.

(10) Patent No.: US 10,906,873 B2
(45) Date of Patent: Feb. 2, 2021

(54) SUBSTITUTED CYCLIC AMIDES AS HERBICIDES

(71) Applicant: FMC Corporation, Philadelphia, PA (US)

(72) Inventors: Matthew James Campbell, Flemington, NJ (US); Andrew Duncan Satterfield, Furlong, PA (US)

(73) Assignee: FMC Corporation, Philadelphia, PA (US)

( * ) Notice: Subject to any disclaimer, the term of this patent is extended or adjusted under 35 U.S.C. 154(b) by 169 days.

(21) Appl. No.: 15/572,029

(22) PCT Filed: May 19, 2016

(86) PCT No.: PCT/US2016/033231
§ 371 (c)(1),
(2) Date: Nov. 6, 2017

(87) PCT Pub. No.: WO2016/196019
PCT Pub. Date: Dec. 8, 2016

(65) Prior Publication Data
US 2018/0141904 A1    May 24, 2018

Related U.S. Application Data

(60) Provisional application No. 62/168,360, filed on May 29, 2015.

(51) Int. Cl.
*A01N 43/36* (2006.01)
*C07D 207/277* (2006.01)
*C07D 401/06* (2006.01)
*C07D 403/06* (2006.01)
*C07D 405/06* (2006.01)
*C07D 409/06* (2006.01)
*C07D 413/06* (2006.01)
*C07D 417/06* (2006.01)
*C07D 471/04* (2006.01)

(52) U.S. Cl.
CPC ......... *C07D 207/277* (2013.01); *A01N 43/36* (2013.01); *C07D 401/06* (2013.01); *C07D 403/06* (2013.01); *C07D 405/06* (2013.01); *C07D 409/06* (2013.01); *C07D 413/06* (2013.01); *C07D 417/06* (2013.01); *C07D 471/04* (2013.01)

(58) Field of Classification Search
None
See application file for complete search history.

(56) References Cited

U.S. PATENT DOCUMENTS

| | | |
|---|---|---|
| 3,741,989 A | 6/1973 | Zaugg |
| 3,959,481 A | 5/1976 | Davis et al. |
| 4,594,094 A | 6/1986 | Kollmeyer |
| 4,874,422 A | 10/1989 | Woolard |
| 5,196,534 A | 3/1993 | Whitehead et al. |
| 7,205,318 B2 | 4/2007 | Qiao et al. |
| 7,375,232 B2 | 5/2008 | Clark et al. |
| 8,293,926 B2 | 10/2012 | Yasuoka et al. |
| 8,461,202 B2 | 6/2013 | Sancho Sanz et al. |
| 8,575,154 B2 | 11/2013 | Kori et al. |
| 8,946,216 B2 | 2/2015 | Deng et al. |
| 9,119,397 B2 | 9/2015 | Yerkes |
| 9,446,995 B2 | 9/2016 | Chong et al. |
| 9,737,073 B2 | 8/2017 | Gifford |
| 9,944,602 B2 | 4/2018 | Satterfield et al. |
| 10,442,807 B2 | 10/2019 | Campbell et al. |
| 2004/0242671 A1 | 12/2004 | Grimee et al. |
| 2006/0019831 A1 | 1/2006 | Reinhard et al. |
| 2007/0123508 A1 | 5/2007 | Olsson et al. |
| 2009/0203694 A1 | 8/2009 | Hurley et al. |
| 2011/0218199 A1 | 9/2011 | Georges et al. |
| 2015/0173371 A1 | 6/2015 | Mann et al. |

(Continued)

FOREIGN PATENT DOCUMENTS

| | | |
|---|---|---|
| CN | 102531918 B | 10/2013 |
| DE | 1 262 277 B | 3/1968 |

(Continued)

OTHER PUBLICATIONS

XP002734980; Jan. 20, 2002.
XP002734981; WO0009481; Feb. 24, 2000.
XP002759805; Jan. 20, 2002.
XP002759806; Mar. 23, 2009.
Murata et al.; "Oxidation of N-Acyl-Pyrrolidines and -Piperidines with Iron(II)-Hydrogen Peroxide and an Iron Complex-Molecular Oxygen"; *J. Chem. Soc. Perkin Trans.*; 1987; 1259-1262. (XP055297105).
Cauliez et al.; "Studies on Pyrrolidinones. On the Carbamoylation of Some Pyroglutamic Derivatives"; *J. Het. Chem.*; 33; 1996; 1233-1237. (XP055297107).
Hwang et al.; "Diastereoselective Synthesis of Oxazolidinone Derivatives and Their Antifungal Activities"; *Korean J. of Med. Chem.*; vol. 4, No. 1; 1994; 52-56. (XP009191451).

(Continued)

*Primary Examiner* — Alton N Pryor
(74) *Attorney, Agent, or Firm* — Reed A Coats

(57) ABSTRACT

Disclosed are compounds of Formula 1, including all stereoisomers, N oxides, and salts thereof,

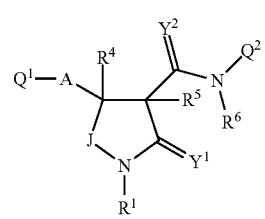

wherein $R^1$, $R^4$, $R^5$, $R^6$, J, $Q^1$, $Q^2$, A, $Y^1$, and $Y^2$ are as defined in the disclosure.
Also disclosed are compositions containing the compounds of Formula 1 and methods for controlling undesired vegetation comprising contacting the undesired vegetation or its environment with an effective amount of a compound or a composition of the invention.

14 Claims, No Drawings

(56) References Cited

U.S. PATENT DOCUMENTS

| | | |
|---|---|---|
| 2016/0137639 A1 | 5/2016 | Kotoku et al. |
| 2016/0289228 A1 | 10/2016 | Defays et al. |
| 2016/0297756 A1 | 10/2016 | Satterfield et al. |
| 2017/0158638 A1 | 6/2017 | Satterfield et al. |
| 2018/0049437 A1 | 2/2018 | Satterfield et al. |
| 2018/0057442 A1 | 3/2018 | Satterfield |
| 2018/0077931 A1 | 3/2018 | Stevenson et al. |
| 2018/0099935 A1 | 4/2018 | Satterfield et al. |
| 2018/0213788 A1 | 8/2018 | Satterfield et al. |
| 2020/0010446 A1 | 1/2020 | Chen |
| 2020/0095202 A1 | 3/2020 | Puri |
| 2020/0115337 A1 | 4/2020 | Campbell |

FOREIGN PATENT DOCUMENTS

| | | |
|---|---|---|
| EP | 2336104 A1 | 6/2011 |
| IN | 1462DEL08 | 6/2008 |
| JP | 53-056288 A | 5/1978 |
| JP | 54-088114 A | 7/1979 |
| JP | 08-269145 A | 10/1996 |
| KR | 20130142477 A | 12/2013 |
| RU | 2555370 C1 | 7/2015 |
| WO | 2000/09481 A1 | 2/2000 |
| WO | 2003024222 | 3/2003 |
| WO | 2004/046081 A1 | 6/2004 |
| WO | 2006/081562 A2 | 8/2006 |
| WO | 2009/062371 A1 | 5/2009 |
| WO | 2012034957 | 3/2012 |
| WO | 2015/084796 A1 | 6/2015 |
| WO | 2016/003997 A1 | 1/2016 |
| WO | 2016/094117 A1 | 6/2016 |
| WO | 2016/164201 A1 | 10/2016 |
| WO | 2016/176082 A1 | 11/2016 |
| WO | 2016/182780 A1 | 11/2016 |
| WO | 2016/196593 A1 | 12/2016 |
| WO | 2017/023515 A1 | 2/2017 |
| WO | 2018/118384 A1 | 6/2018 |
| WO | 2018175226 | 9/2018 |
| WO | 2018175231 | 9/2018 |

OTHER PUBLICATIONS

Campaigne et el.; Synthesis of Some Ureidodihydrofurans and Related Pyrimidones as Potential Antimalarials; *J. Med. Chem.*; 1969; 339-342. (XP002278920).

IPCOM000241978D; Jun. 11, 2015.

PubChem Entry CID 29937915 (45)-4-[3-(trifluoromethyl)phenyl]pyrrolidin-2-one: May 28, 2009.

Banerjee et al., "A Stereoselective Cyclization Strategy for the Preparation of gamma-Lactams and Their Use in the Synthesis of alpha-Methyl-beta-Proline", J. Org. Chem. 2012, vol. 77, pp. 10925-10930.

Wang et al., "Asymmetric Cyanation of Activated Olefins with Ethyl Cyanoformate Catalyzed by a Modular Titanium catalyst", Org. Lett., 2010, vol. 12(6), pp. 1280-1283.

Hajra et al., "Organocatalytic enantioselective conjugate addition of nitromethane to alkylidenemalonates: asymmetric synthesis of pyrrolidine-3-carboxylic acid derivatives", RSC Advances, vol. 3, No. 26, Jan. 1, 2013, pp. 10185-10188.

SUBSTITUTED CYCLIC AMIDES AS HERBICIDES

FIELD OF THE INVENTION

This invention relates to certain substituted cyclic amides, their N-oxides and salts, and compositions and methods of their use for controlling undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safer or have different sites of action.

SUMMARY OF THE INVENTION

This invention is directed to compounds of Formula 1 (including all stereoisomers), N-oxides and salts thereof, agricultural compositions containing them and their use as herbicides:

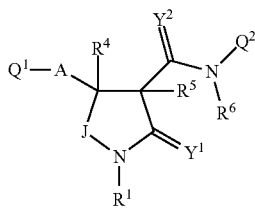

wherein
A is a saturated, partially unsaturated or fully unsaturated chain containing 1 to 3 atoms selected from up to 3 carbon, up to 1 O, up to 1 S and up to 2 N atoms, wherein up to 2 carbon members are independently selected from C(=O) and C(=S) and the sulfur atom member is selected from $S(=O)_u(=NR^8)_v$; the said chain optionally substituted with up to 5 substituents independently selected from $R^{15}$ on carbon atoms and $R^{16}$ on nitrogen atoms;

$Q^1$ is a phenyl ring or a naphthalenyl ring system, each ring or ring system optionally substituted with up to 5 substituents independently selected from $R^7$; or a 5- to 6-membered heteroaromatic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^7$ on carbon atom ring members and selected from $R^9$ on nitrogen atom ring members;

$Q^2$ is a phenyl ring or a naphthalenyl ring system, each ring or ring system optionally substituted with up to 5 substituents independently selected from $R^{10}$; or a 5- to 6-membered heteroaromatic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^{10}$ on carbon atom ring members and selected from $R^{11}$ on nitrogen atom ring members;

$Y^1$ and $Y^2$ are each independently O, S or $NR^{12}$;

J is —$CR^2R^3$—; or —$CR^2R^3$—$CR^{2a}R^{3a}$— wherein the —$CR^2R^3$— moiety is directly connected to N;

$R^1$ is H, hydroxy, amino, cyano, formyl, $C_3$-$C_8$ alkylcarbonylalkyl, —$C(C_1$-$C_4$ alkyl)=N—O($C_1$-$C_4$ alkyl), —C(O)NH$_2$, $C_1$-$C_6$ alkyl, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkenylalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_5$-$C_{10}$ cycloalkylcarbonylalkyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminoalkyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl; or arylcarbonyl, arylalkenylalkyl, arylcarbonylalklyl or —CPh=N—O($C_1$-$C_4$ alkyl), each optionally substituted on ring members with up to 5 substituents independently selected from $R^{13}$; or $G^1$;

$R^2$ and $R^3$ are each independently H, halogen, hydroxy, $C_1$-$C_4$ alkyl, $C_1$-$C_4$ haloalkyl or $C_1$-$C_4$ alkoxy; or $R^2$ and $R^3$ are taken together with the carbon atom to which they are bonded to form a $C_3$-$C_7$ cycloalkyl ring;

$R^{2a}$ and $R^{3a}$ are each independently H, halogen or $C_1$-$C_4$ alkyl; or $R^{2a}$ and $R^{3a}$ are taken together with the carbon atom to which they are bonded to form a $C_3$-$C_7$ cycloalkyl ring;

each $R^4$ is independently H, halogen, hydroxy, $C_1$-$C_4$ alkoxy or $C_1$-$C_4$ alkyl; each $R^5$ is independently H, halogen, hydroxy, $C_1$-$C_4$ alkoxy, cyano or $C_1$-$C_4$ alkyl;

$R^6$ is H, hydroxy, amino, $C_1$-$C_6$ alkyl, $C_1$-$C_6$ haloalkyl, $C_2$-$C_6$ alkenyl, $C_3$-$C_6$ alkynyl, $C_2$-$C_8$ alkoxyalkyl, $C_3$-$C_8$ alkoxyalkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl or $C_3$-$C_{10}$ trialkylsilyl; or $G^1$;

each $R^7$ is independently halogen, hydroxy, cyano, nitro, $C_1$-$C_8$ alkyl, $C_2$-$C_8$ cyanoalkyl, $C_1$-$C_8$ cyanoalkoxy, $C_1$-$C_8$ haloalkyl, $C_2$-$C_8$ alkenyl, $C_2$-$C_8$ haloalkenyl, $C_2$-$C_8$ alkynyl, $C_2$-$C_8$ haloalkynyl, $C_1$-$C_8$ nitroalkyl, $C_2$-$C_8$ nitroalkenyl, $C_2$-$C_8$ alkoxyalkyl, $C_3$-$C_8$ alkoxyalkoxyalkyl, $C_2$-$C_8$ haloalkoxyalkyl, $C_3$-$C_8$ cycloalkyl, $C_3$-$C_8$ halocycloalkyl, $C_4$-$C_{10}$ cycloalkylalkyl, $C_4$-$C_{10}$ alkylcyclolalkyl, $C_1$-$C_8$ alkoxy, $C_1$-$C_8$ haloalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_1$-$C_8$ alkylthio, $C_1$-$C_8$ haloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, hydroxy, formyl, $C_2$-$C_8$ alkylcarbonyl, $C_2$-$C_8$ alkylcarbonyloxy, $C_1$-$C_8$ alkylsulfonyloxy, $C_1$-$C_8$ haloalkylsulfonyloxy, amino, $C_1$-$C_4$ alkylamino, $C_2$-$C_4$ dialkylamino, formylamino, $C_2$-$C_4$ alkylcarbonylamino, —$SF_5$, —SCN, $C_4$-$C_{10}$ cycloalkylalkoxy, $C_4$-$C_{10}$ cycloalkylalkyl, $C_2$-$C_8$ alkenyloxy, $C_2$-$C_8$ haloalkenyloxy, $C_2$-$C_8$ alkoxyalkoxy, $C_2$-$C_8$ alkylthioalkyl, $C_2$-$C_8$ alkylsulfinylalkyl, $C_2$-$C_8$ alkylsulfonylalkyl, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_2$-$C_8$ alkynyl, $C_2$-$C_8$ haloalkynyl, $C_2$-$C_8$ alkoxyalkyl, $C_2$-$C_8$ haloalkoxyalkyl, $C_3$-$C_8$ haloalkoxyalkoxy, $C_2$-$C_8$ haloalkoxyhaloalkyl, $C_1$-$C_8$ haloalkyl, $C_3$-$C_8$ halocycloalkyl, $C_2$-$C_8$ alkylcarbonyloxy, $C_2$-$C_8$ haloalkylcarbonyloxy, $C_3$-$C_{12}$ trialkylsilyl, trimethylsilylmethyl or trimethylsilylmethoxy; or $G^2$; or $R^{17}ON\!\!=\!\!CR^{17a}\!\!-\!\!$, $(R^{18})_2C\!\!=\!\!NO\!\!-\!\!$, $(R^{19})_2NN\!\!=\!\!CR^{17a}\!\!-\!\!$, $(R^{18})_2C\!\!=\!\!NNR^{20a}$, $R^{20}N\!\!=\!\!CR^{17a}\!\!-\!\!$, $(R^{18})_2C\!\!=\!\!N\!\!-\!\!$, $R^{17}ON\!\!=\!\!CR^{17a}C(R^{23b})_2\!\!-\!\!$ or $(R^{18})_2C\!\!=\!\!NOC(R^{24a})_2\!\!-\!\!$, wherein the free bond projecting to the right indicates the connecting point to $Q^1$; or two adjacent $R^7$ are taken together along with the carbon atoms to which they are bonded to form a $C_3$-$C_7$ cycloalkyl ring;

each $R^{10}$ is independently halogen, hydroxy, cyano, nitro, $C_1$-$C_8$ alkyl, $C_2$-$C_8$ cyanoalkyl, $C_1$-$C_8$ cyanoalkoxy, $C_1$-$C_8$ haloalkyl, $C_2$-$C_8$ alkenyl, $C_2$-$C_8$ haloalkenyl, $C_2$-$C_8$ alkynyl, $C_2$-$C_8$ haloalkynyl, $C_1$-$C_8$ nitroalkyl, $C_2$-$C_8$ nitroalkenyl, $C_2$-$C_8$ alkoxyalkyl, $C_3$-$C_8$ alkoxyalkoxyalkyl, $C_2$-$C_8$ haloalkoxyalkyl, $C_3$-$C_8$ cycloalkyl, $C_3$-$C_8$ halocycloalkyl, $C_4$-$C_{10}$ cycloalkylalkyl, $C_4$-$C_{10}$ alkylcyclolalkyl, $C_1$-$C_8$ alkoxy, $C_1$-$C_8$ haloalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_1$-$C_8$ alkylthio, $C_1$-$C_8$ haloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, hydroxy, formyl, $C_2$-$C_8$ alkylcarbonyl, $C_2$-$C_8$ alkylcarbonyloxy, $C_1$-$C_8$ alkylsulfonyloxy, $C_1$-$C_8$ haloalkylsulfonyloxy, amino, $C_1$-$C_4$ alkylamino, $C_2$-$C_4$ dialkylamino, formylamino, $C_2$-$C_4$ alkylcarbonylamino, —$SF_5$, —SCN, $C_4$-$C_{10}$ cycloalkylalkoxy, $C_4$-$C_{10}$ cycloalkylalkyl, $C_2$-$C_8$ alkenyloxy, $C_2$-$C_8$ haloalkenyloxy, $C_2$-$C_8$ alkoxyalkoxy, $C_2$-$C_8$ alkylthioalkyl, $C_2$-$C_8$ alkylsulfinylalkyl, $C_2$-$C_8$ alkylsulfonylalkyl, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_2$-$C_8$ alkynyl, $C_2$-$C_8$ haloalkynyl, $C_2$-$C_8$ alkoxyalkyl, $C_2$-$C_8$ haloalkoxyalkyl, $C_3$-$C_8$ haloalkoxyalkoxy, $C_2$-$C_8$ haloalkoxyhaloalkyl, $C_1$-$C_8$ haloalkyl, $C_3$-$C_8$ halocycloalkyl, $C_2$-$C_8$ alkylcarbonyloxy, $C_2$-$C_8$ haloalkylcarbonyloxy, $C_3$-$C_{12}$ trialkylsilyl, trimethylsilylmethyl or trimethylsilylmethoxy; or $G^2$; or $R^{17}ON\!\!=\!\!CR^{17a}\!\!-\!\!$, $(R^{18})_2C\!\!=\!\!NO\!\!-\!\!$, $(R^{19})_2NN\!\!=\!\!CR^{17a}\!\!-\!\!$, $(R^{18})_2C\!\!=\!\!NNR^{20a}$, $R^{20}N\!\!=\!\!CR^{17a}\!\!-\!\!$, $(R^{18})_2C\!\!=\!\!N\!\!-\!\!$, $R^{17}ON\!\!=\!\!CR^{17a}C(R^{23b})_2\!\!-\!\!$ or $(R^{18})_2C\!\!=\!\!NOC(R^{24a})_2\!\!-\!\!$, wherein the free bond projecting to the right indicates the connecting point to $Q^2$; or two adjacent $R^{10}$ are taken together along with the carbon atoms to which they are bonded to form a $C_3$-$C_7$ cycloalkyl ring;

each $R^8$ is independently H, cyano, $C_2$-$C_3$ alkylcarbonyl or $C_2$-$C_3$ haloalkylcarbonyl;

each $R^9$ and $R^{11}$ is independently cyano, $C_1$-$C_3$ alkyl, $C_2$-$C_3$ alkenyl, $C_2$-$C_3$ alkynyl, $C_3$-$C_6$ cycloalkyl, $C_2$-$C_3$ alkoxyalkyl, $C_1$-$C_3$ alkoxy, $C_2$-$C_3$ alkylcarbonyl, $C_2$-$C_3$ alkoxycarbonyl, $C_2$-$C_3$ alkylaminoalkyl or $C_3$-$C_4$ dialkylaminoalkyl; each $R^{12}$ is independently H, cyano, $C_1$-$C_4$ alkyl, $C_1$-$C_4$ haloalkyl, $C_1$-$C_4$ alkoxy, $C_1$-$C_4$ haloalkoxy, —(C=O)CH$_3$ or —(C=O)CF$_3$;

each $G^1$ is independently phenyl, phenylmethyl (i.e. benzyl), pyridinylmethyl, phenylcarbonyl (i.e. benzoyl), phenoxy, phenylethynyl, phenylsulfonyl, phenylcarbonylalkyl, 2-, 3- or 4-pyridinyloxy or a 5- or 6-membered heteroaromatic ring, each optionally substituted on ring members with up to 5 substituents independently selected from $R^{13}$;

each $G^2$ is independently phenyl, phenylmethyl (i.e. benzyl), pyridinylmethyl, phenylcarbonyl (i.e. benzoyl), phenylcarbonylalkyl, phenoxy, phenylethynyl, phenylsulfonyl, 2-, 3- or 4-pyridinyloxy or a 5- or 6-membered heteroaromatic ring, each optionally substituted on ring members with up to 5 substituents independently selected from $R^{14}$;

each $R^{13}$ and $R^{14}$ is independently halogen, cyano, hydroxy, amino, nitro, —CHO, —C(=O)OH, —C(=O)NH$_2$, —SO$_2$NH$_2$, $C_1$-$C_6$ alkyl, $C_1$-$C_6$ haloalkyl, $C_2$-$C_6$ alkenyl, $C_2$-$C_6$ alkynyl, $C_2$-$C_8$ alkylcarbonyl, $C_2$-$C_8$ haloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylaminosulfonyl, $C_2$-$C_8$ dialkylaminosulfonyl, $C_3$-$C_{10}$ trialkylsilyl, $C_1$-$C_6$ alkylamino, $C_2$-$C_8$ dialkylamino, $C_2$-$C_8$ alkylcarbonylamino, $C_1$-$C_6$ alkylsulfonylamino, phenyl, pyridinyl or thienyl;

each $R^{15}$ is independently halogen, cyano, hydroxy, $C_1$-$C_4$ alkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl, $C_3$-$C_6$ cycloalkyl or $C_4$-$C_8$ cycloalkylalkyl; or two $R^{15}$ are taken together with the carbon atom(s) to which they are bonded to form a $C_3$-$C_7$ cycloalkyl ring;

each $R^{16}$ is independently cyano, $C_1$-$C_4$ alkyl, $C_1$-$C_4$ haloalkyl, $C_1$-$C_4$ alkoxy, $C_2$-$C_4$ alkylcarbonyl, $C_2$-$C_4$ alkoxycarbonyl or $C_3$-$C_6$ cycloalkyl;

each $R^{17}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl or $C_3$-$C_{10}$ trialkylsilyl; or $G^1$;

each $R^{17a}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy, $C_1$-$C_6$ alkylthio, $C_1$-$C_6$ haloalkylthio, $C_3$-$C_8$ cycloalkylthio or $C_3$-$C_{10}$ trialkylsilyl; or $G^1$;

each $R^{18}$ is independently H, hydroxy, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl or $C_3$-$C_{10}$ trialkylsilyl; or $G^1$;

each $R^{19}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl or $C_3$-$C_{10}$ trialkylsilyl; or $G^1$;

each $R^{20}$ is independently H, hydroxy, amino, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl or $C_3$-$C_{10}$ trialkylsilyl; or $G^1$;

each $R^{20a}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy or $C_3$-$C_{10}$ trialkylsilyl; or $G^1$;

each $R^{23b}$ is independently H, halogen, cyano, hydroxy, $C_1$-$C_4$ alkyl, $C_3$-$C_8$ cycloalkyl, $C_4$-$C_8$ cycloalkylalkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl or $C_3$-$C_6$ cycloalkyl;

each $R^{24a}$ is independently H, $C_1$-$C_4$ alkyl, $C_3$-$C_8$ cycloalkyl, $C_4$-$C_8$ cycloalkylalkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl or $C_3$-$C_6$ cycloalkyl; and each u and v are independently 0, 1 or 2 in each instance of $S(=O)_u(=NR^8)_v$, provided that the sum of u and v is 0, 1 or 2;

provided when A is S and $Q^1$ is unsubstituted phenyl, $Q^2$ is other than unsubstituted phenyl.

More particularly, this invention pertains to a compound of Formula 1 (including all stereoisomers), an N-oxide or a salt thereof. This invention also relates to a herbicidal composition comprising a compound of the invention (i.e. in a herbicidally effective amount) and at least one component selected from the group consisting of surfactants, solid diluents and liquid diluents. This invention further relates to a method for controlling the growth of undesired vegetation comprising contacting the vegetation or its environment with a herbicidally effective amount of a compound of the invention (e.g., as a composition described herein).

This invention also includes a herbicidal mixture comprising (a) a compound selected from Formula 1, N-oxides and salts thereof, and (b) at least one additional active ingredient selected from (b1) through (b16); and salts of compounds of (b1) through (b16), as described below.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated.

For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method or apparatus that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated)

the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed.

As referred to herein, the term "broadleaf" used either alone or in words such as "broadleaf weed" means dicot or dicotyledon, a term used to describe a group of angiosperms characterized by embryos having two cotyledons.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl, and the different butenyl, pentenyl and hexynyl isomers. The term "trialkylsilyl" me and three alkyl groups attached through silicon, with each alkyl being the same or different.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2-$, $CH_3OCH_2CH_2-$, $CH_3CH_2OCH_2-$, $CH_3CH_2CH_2CH_2OCH_2-$ and $CH_3CH_2OCH_2CH_2-$. "Alkoxyalkoxy" denotes alkoxy substitution on alkoxy. "Alkoxyalkoxyalkyl" denotes alkoxy substitution on the alkoxy moiety of alkoxyalkyl moiety. Examples of "alkoxyalkoxyalkyl" include $CH_3OCH_2OCH_2-$, $CH_3CH_2O(CH_3)CHOCH_2-$ and $(CH_3O)_2CHOCH_2-$. "Alkenyloxy" includes straight-chain or branched alkenyloxy moieties. Examples of "alkenyloxy" include $H_2C=CHCH_2O-$, $(CH_3)_2C=CHCH_2O-$, $(CH_3)CH=CHCH_2O-$, $(CH_3)CH=C(CH_3)CH_2O-$ and $CH_2=CHCH_2CH_2O-$. "Alkynyloxy" includes straight-chain or branched alkynyloxy moieties. Examples of "alkynyloxy" include $HC\equiv CCH_2O-$, $CH_3C\equiv CCH_2O-$ and $CH_3C\equiv CCH_2CH_2O-$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)-$, $CH_3CH_2S(O)-$, $CH_3CH_2CH_2S(O)-$, $(CH_3)_2CHS(O)-$ and the different butylsulfinyl, pentylsulfinyl and hexylsulfinyl isomers. Examples of "alkylsulfonyl" include $CH_3S(O)_2-$, $CH_3CH_2S(O)_2-$, $CH_3CH_2CH_2S(O)_2-$, $(CH_3)_2CHS(O)_2-$, and the different butylsulfonyl, pentylsulfonyl and hexylsulfonyl isomers. Examples of "alkyl sulfonylamino" include $CH_3S(O)_2NH-$, $CH_3CH_2S(O)_2NH-$, $CH_3CH_2CH_2S(O)_2NH-$, $(CH_3)_2CHS(O)_2NH-$, and the different butylsulfonylamino, pentylsulfonylamino and hexylsulfonylamino isomers. Examples of "alkylaminosulfonyl" include $CH_3NHS(O)_2-$, $CH_3CH_2NHS(O)_2-$, $CH_3CH_2CH_2NHS(O)_2-$, $(CH_3)_2CHNHS(O)_2-$, and the different butylsulfonylamino, pentylsulfonylamino and hexylsulfonylamino isomers. Examples of "alkylsulfonyloxy" include $CH_3S(O)_2O-$, $CH_3CH_2S(O)_2O-$, $CH_3CH_2CH_2S(O)_2O-$, $(CH_3)_2CHS(O)_2O-$, and the different butylsulfonyloxy, pentylsulfonyloxy and hexylsulfonyloxy isomers. "Alkylthioalkyl" denotes alkylthio substitution on alkyl. Examples of "alkylthioalkyl" include $CH_3SCH_2-$, $CH_3SCH_2CH_2-$, $CH_3CH_2SCH_2-$, $CH_3CH_2CH_2CH_2SCH_2-$ and $CH_3CH_2SCH_2CH_2-$. "Cyanoalkyl" denotes an alkyl group substituted with one cyano group. Examples of "cyanoalkyl" include $NCCH_2-$, $NCCH_2CH_2-$ and $CH_3CH(CN)CH_2-$. "Cyanoalkoxy" denotes an alkoxy group substituted with one cyano group. Examples of "cyanoalkoxy" include $NCCH_2O-$, $NCCH_2CH_2O-$ and $CH_3CH(CN)CH_2O-$. "Nitroalkenyl" denotes an alkenyl group substituted with one nitro group. Examples of "nitroalkenyl" include $O_2NCH=CH-$, $O_2NCH_2CH=CH-$ and $CH_2=CH(NO_2)CH_2-$. "nitroalkyl" denotes an alkyl group substituted with one nitro group. Examples of "nitroalkyl" include $O_2NCH_2-$, $O_2NCH_2CH_2-$ and $CH_3CH_2CH(NO_2)-$. "Alkylsulfinylalkyl" denotes alkylsulfinyl substitution on alkyl. Examples of "alkylsulfinylalkyl" include $CH_3S(=O)CH_2-$, $CH_3S(=O)CH_2CH_2-$, $CH_3CH_2S(=O)CH_2-$ and $CH_3CH_2S(=O)CH_2CH_2-$. "Alkyl sulfonylalkyl" denotes alkylsulfonyl substitution on alkyl. Examples of "alkylsulfonylalkyl" include $CH_3S(=O)_2CH_2-$, $CH_3S(=O)_2CH_2CH_2-$, $CH_3CH_2S(=O)_2CH_2-$ and $CH_3CH_2S(=O)_2CH_2CH_2-$. "Cyloalkylthio" denotes a cycloalkyl group bonded through sulfur. Examples of "cycloalkylthio" include c-PrS—, c-BuS- and c-HexS—. "Cycloalkysulfinyl" and "cycloalkylsulfonyl" are defined analogously, "Alkylamino", "dialkylamino", and the like, are defined analogously to the above examples. Examples of "alkylaminoalkyl" include $CH_3NHCH_2-$, $(CH_3)_2CHNHCH_2-$ and $CH_3NHCH(CH_3)-$. Examples of "alkylaminocarbonyl" include $CH_3NHC(O)-$, $(CH_3)_2CHNHC(O)-$ and $CH_3CH_2NHC(O)-$. Examples of "dialkylaminoalkyl" include $(CH_3)_2NCH_2-$, $(CH_3)_2NC(CH_3)H-$ and $(CH_3)(CH_3)NCH_2-$. Examples of "alkylaminocarbonyl" include $CH_3NC(O)-$ and $CH_3CH_2NC(O)-$. Examples of "dialkylaminocarbonyl" include $(CH_3)_2NC(O)-$. Examples of "dialkylaminosulfonyl" include $(CH_3)_2NS(O)_2-$.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. The term "cycloalkoxy" denotes cycloalkyl linked through an oxygen atom such as cyclopentyloxy and cyclohexyloxy. "Cycloalkylalkoxycarbonyl" denotes cycloalkyl substitution on an alkoxycarbonyl moiety. Examples of "cycloalkylalkoxycarbonyl" include c-PrCH$_2$OC(=O)-c-BuCH$_2$OC(=O)— and c-HexCH$_2$OC(=O)—. "Cycloalkoxycarbonyl" denotes cycloalkoxy substitution on a carbonyl moiety. Examples of "cycloalkoxycarbonyl" include cyclopropoxycarbonyl, cyclopentoxycarbonyl, and other moieties bonded to straight-chain or branched alkyl groups. "Cycloalkylalkoxy" denotes cycloalkylalkyl linked through an oxygen atom attached to the alkyl chain. Examples of "cycloalkylalkoxy" include cyclopropylmethoxy, cyclopentylethoxy, and other cycloalkyl moieties bonded to straight-chain or branched alkoxy groups.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$—, $ClCH_2$—, $CF_3CH_2$— and $CF_3CCl_2$—. The terms "halocycloalkyl", "haloalkoxy", "haloalkoxyalkyl", "haloalkylthio", "haloalkylsulfinyl" "haloalkylsulfonyl", "haloalkylsulfonyloxy" "haloalkenyl", "haloalkenylalkyl", "haloalkynyl", "haloalkenyloxy", "haloalkoxycarbonyl", "haloalkylcarbonyloxy" and the like, are defined analogously to the term "haloalkyl". Examples of "haloalkoxy" include $CF_3O$—, $CCl_3CH_2O$—, $HCF_2CH_2CH_2O$— and $CF_3CH_2O$—. Examples of "haloalkoxyalkyl" include $CCl_3OCH_2$—, $CF_3OCH_2CH_2$— and $CCl_3CH_2CH_2O$—. Examples of "haloalkylthio" include $CCl_3S$—, $CF_3S$—, $CCl_3CH_2S$— and $ClCH_2CH_2CH_2S$—. Examples of "haloalkylsulfinyl" include $CF_3S(O)$—, $CCl_3S(O)$—, $CF_3CH_2S(O)$— and $CF_3CF_2S(O)$—. Examples of "haloalkylsulfonyl" include $CF_3S(O)_2$—, $CCl_3S(O)_2$—, $CF_3CH_2S(O)_2$— and $CF_3CF_2S(O)_2$—. Examples of "haloalkylsulfonyloxy" include $CF_3S(O)_2O$—, $CCl_3S(O)_2O$—, $CF_3CH_2S(O)_2O$— and $CF_3CF_2S(O)_2O$—. Examples of "haloalkenyl" and "haloalkenylalkyl" include $(Cl)_2C=CHCH_2$— and $CF_3CH_2CH=CHCH_2$—. Examples of "haloalkynyl" include $HC\equiv CCHCl$—, $CF_3C\equiv C$—, $CCl_3C\equiv C$— and $FCH_2C\equiv CCH_2$—. Examples of "haloalkoxyalkoxy" include $CF_3OCH_2O$—, $ClCH_2CH_2OCH_2CH_2O$—, $Cl_3CCH_2OCH_2O$— as well as branched alkyl derivatives. Examples of "haloalkenyloxy" include $CF_3CH=CHO$—, $ClCH_2CH=CH\ CH_2O$—, $CH_3CCl=ClCH_2O$— as well as branched derivatives. Examples of "haloalkoxycarbonyl" include $CF_3CH_2OC(=O)$—, $ClCH_2CH_2OC(=O)$— and $CH_3CCl_2CH_2OC(=O)$—. Examples of "haloalkylcarbonyloxy" include $CF_3CH_2C(=O)O$—, $ClCH_2CH_2C(=O)O$— and $CH_3CCl_2CH_2C(=O)O$—.

"Alkylcarbonyl" denotes a straight-chain or branched alkyl moieties bonded to a $C(=O)$ moiety. Examples of "alkylcarbonyl" include $CH_3C(=O)$—, $CH_3CH_2CH_2C(=O)$— and $(CH_3)_2CHC(=O)$—. Examples of "alkylcarbonylalkyl" include $CH_3C(=O)CH_2$—, $CH_3CH_2CH_2C(=O)CH_2$— and $(CH_3)_2CHC(=O)CH_2$—. Examples of "alkoxycarbonyl" include $CH_3OC(=O)$—, $CH_3CH_2OC(=O)$—, $CH_3CH_2CH_2OC(=O)$—, $(CH_3)_2CHOC(=O)$— and the different butoxy- or pentoxycarbonyl isomers. "Alkylcarbonyloxy" denotes an alkylcarbonyl moiety linked through an oxygen atom attached to the carbonyl. Examples of "alkylcarbonyloxy" include $CH_3C(=O)O$—, $CH_3CH_2CH_2C(=O)O$— and $(CH_3)_2CHC(=O)O$—. "Alkylcarbonylamino" denotes an alkylcarbonyl moiety linked through an amino moiety atom attached to the carbonyl. Examples of "alkylcarbonylamino" include $CH_3C(=O)NH$—, $CH_3CH_2CH_2C(=O)NH$— and $(CH_3)_2CHC(=O)NH$—. "Cycloalkylaminocarbonyl" denotes cycloalkyl substitution on an aminocarbonyl moiety. Examples of "cycloalkylaminocarbonyl" include c-PrNHC(=O)—, c-BuNHC(=O)— and c-HexNHC(=O)—. "Cycloalkylcarbonyl" denotes cycloalkyl substitution on a carbonyl moiety. Examples of "cycloalkylcarbonyl" include c-PrC(=O)—, c-BuCH$_2$NHC(=O)— and c-HexCH$_2$NHC(=O)-cycloalkylcarbonyl. "Cycloalkylcarbonylalkyl" denotes cycloalkyl substitution on a carbonylalkyl moiety. Examples of "cycloalkylcarbonylalkyl" include c-PrC(=O)CH$_2$—, c-Bu(=O)CH$_2$CH$_2$— and c-HexC(=O)CH$_2$—.

The total number of carbon atoms in a substituent group is indicated by the "$C_i$-$C_j$" prefix where i and j are numbers from 1 to 12. For example, $C_1$-$C_4$ alkylsulfonyl designates methylsulfonyl through butylsulfonyl; $C_2$ alkoxyalkyl designates $CH_3OCH_2$—; $C_3$ alkoxyalkyl designates, for example, $CH_3CH(OCH_3)$—, $CH_3OCH_2CH_2$— or $CH_3CH_2OCH_2$—; and $C_4$ alkoxyalkyl designates the various isomers of an alkyl group substituted with an alkoxy group containing a total of four carbon atoms, examples including $CH_3CH_2CH_2OCH_2$— and $CH_3CH_2OCH_2CH_2$—.

When a compound is substituted with a substituent bearing a subscript that indicates the number of said substituents can exceed 1, said substituents (when they exceed 1) are independently selected from the group of defined substituents, e.g., ($[(R^{10})_n]$, n is 1, 2, 3, 4 or 5). Further, when the subscript indicates a range, e.g. $(R)_{i-j}$, then the number of substituents may be selected from the integers between i and j inclusive. When a group contains a substituent which can be hydrogen, for example ($R^1$ or $R^6$), then when this substituent is taken as hydrogen, it is recognized that this is equivalent to said group being unsubstituted. When a variable group is shown to be optionally attached to a position, for example $[(R^{10})_n]$ wherein n may be 0, then hydrogen may be at the position even if not recited in the variable group definition. When one or more positions on a group are said to be "not substituted" or "unsubstituted", then hydrogen atoms are attached to take up any free valency.

The expression "fully saturated" in relation to a ring of atoms means that the bonds between the atoms of the ring are all single. The expression "fully unsaturated" in relation to a ring means that the bonds between the atoms in the ring are single or double bonds according to valence bond theory and furthermore the bonds between the atoms in the ring include as many double bonds as possible without double bonds being cumulative (i.e. no C=C=C, N=C=C, etc.). The term "partially unsaturated" in relation to a ring denotes a ring comprising at least one ring member bonded to an adjacent ring member though a double bond and which conceptually potentially accommodates a number of non-cumulated double bonds through adjacent ring members (i.e. in its fully unsaturated counterpart form) greater than the number of double bonds present (i.e. in its partially unsaturated form). When a fully unsaturated ring satisfies Hückel's rule then it can also be described as aromatic.

Unless otherwise indicated, a "ring" or "ring system" as a component of Formula 1 (e.g., substituent $Q^1$) is carbocyclic or heterocyclic. The term "ring system" denotes two or more fused rings. The terms "bicyclic ring system" denote a ring system consisting of two fused rings, in which either ring can be saturated, partially unsaturated, or fully unsaturated unless otherwise indicated. The term "ring member" refers to an atom or other moiety (e.g., C(=O), C(=S), S(O) or S(O)$_2$) forming the backbone of a ring or ring system.

The terms "carbocyclic ring" or "carbocyclic ring system" denote a ring or ring system wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

The terms "heterocyclic ring", "heterocycle" or "heterocyclic ring system" denote a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring". The term "heteroaromatic bicyclic ring system" denotes a heterocyclic ring system in which at least one of the ring system is aromatic. Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and that (4n+2) π electrons, where n is a positive integer, are associated with the ring to comply with Hückel's rule. The term "aromatic ring system" denotes a carbocyclic or heterocyclic ring system in which at least one ring of the ring system is aromatic.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

As described in the Summary of the Invention, J can be either —CR$^2$R$^3$—; or —CR$^2$R$^3$—CR$^{2a}$R$^{3a}$— wherein the —CR$^2$R$^3$— moiety is directly connected to N. For example, when J is —CR$^2$R$^3$—, the compound of Formula 1 is represented by Formula 1A. When J is —CR$^2$R$^3$—CR$^{2a}$R$^{3a}$—, the compound of Formula 1 is represented by Formula 1B

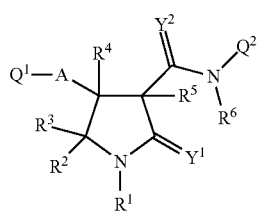

1A

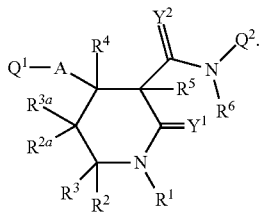

1B where each of the remaining variables are defined in the Summary of the Invention.

As described in the Summary of the Invention, A can be a saturated, partially unsaturated or fully unsaturated chain containing 1 to 3 atoms selected from up to 3 carbon, up to 1 O, up to 1 S and up to 2 N atoms, wherein up to 2 carbon members are independently selected from C(=O) and C(=S) and the sulfur atom member is selected from S(=O)$_u$(=NR$^8$)$_v$; the said chain optionally substituted with up to 5 substituents independently selected from R$^{15}$ on carbon atoms and R$^{16}$ on nitrogen atoms. Examples of A include —ON=CH—, —ON=C(CH$_3$)—, —NHN=CH—, —NHN=C(CH$_3$)—, —N=CH—, —N=C(CH$_3$)—, —CH=NO—, —C(CH$_3$)=NO—, —CH=NNH—, —C(CH$_3$)=NNH—, —CH=N—, —C(CH$_3$)=N—, —CH$_2$CH$_2$CH$_2$—, —CH$_2$CH$_2$—, —CH$_2$—, —CF$_2$—, —C(=O)—, —CH=CH—, —CH=CHCH$_2$—, —CH$_2$CH=CH—, —C≡C—, —C≡CCH$_2$—, —CH$_2$C≡C—, —CH$_2$CH$_2$O—, —CH$_2$O—, —O—, —OCH$_2$CH$_2$—, —OCH$_2$—, —CH$_2$CH$_2$S—, —CH$_2$S—, —S—, —SO—, —SO$_2$—, —SCH$_2$CH$_2$—, —SCH$_2$—, —CH$_2$CH$_2$NH—, —CH$_2$NH—, —NH—, —NHCH$_2$— and —NHCH$_2$CH$_2$— wherein the bond projecting to the left is connected to the Q$^1$ moiety, and the bond projecting to the right is connected to the remainder of Formula 1.

As noted above, Q$^1$ and Q$^2$ can be (among others) phenyl optionally substituted with one or more substituents selected from a group of substituents as defined in the Summary of the Invention. An example of phenyl optionally substituted with one to five substituents is the ring illustrated as U-1 in Exhibit 1, wherein, for example, R$^v$ is R$^7$ as defined in the Summary of the Invention for Q$^1$ and r is an integer (from 0 to 5); or R$^v$ is R$^{10}$ as defined in the Summary of the Invention for Q$^2$, and r is an integer (from 0 to 5); or R$^v$ is R$^9$ as defined in the Summary of the Invention for Q$^1$ and r is an integer (from 0 to 5) when R$^v$ is bonded to nitrogen atom; or R$^v$ is R$^{11}$ as defined in the Summary of the Invention for Q$^2$ and r is an integer (from 0 to 5) when R$^v$ is bonded to nitrogen atom. In the Summary of the Invention R$^1$ can be arylcarbonyl, arylalkenylalkyl, arylcarbonylalkyl or —CPh=N—O(C$_1$-C$_4$ alkyl), each optionally substituted on ring members with up to 5 substituents independently selected from R$^{13}$. In this context, the term the "aryl" can be substituted by R$^{13}$ and is connected to the remainder of Formula 1 through a carbonyl group, an alkenylalkyl group or a carbonylalkyl group as defined above (e.g., aryl (C=O)—, aryl(C$_2$-C$_8$ alkenylalkyl)- or aryl(C=O)(C$_1$-C$_4$ alkyl)-). The phenyl group in the —CPh=N—O(C$_1$-C$_4$ alkyl) moiety can be further substituted by R$^{13}$.

As noted above, Q$^1$ and Q$^2$ can be (among others) a 5- or 6-membered heteroaromatic ring, optionally substituted with one or more substituents selected from a group of substituents as defined in the Summary of the Invention. Examples of a 5- or 6-membered heteroaromatic ring optionally substituted with from one or more substituents include the rings U-2 through U-61 illustrated in Exhibit 1 wherein R$^v$ is any substituent as defined in the Summary of the Invention for Q$^1$ and Q$^2$, and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by (R$^v$)$_r$.

Exhibit 1
U-1 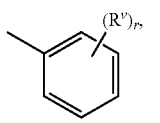
U-2 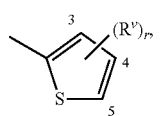
U-3 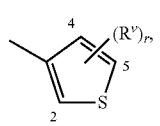
U-4 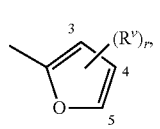
U-5 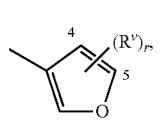
U-6 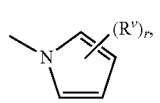
U-7 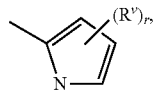
U-8 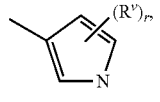
U-9 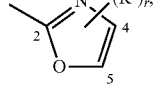
U-10 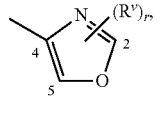
U-11 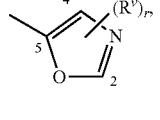
U-12 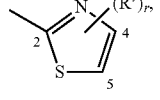
-continued
U-13 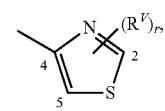
U-14 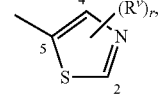
U-15 
U-16 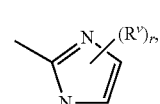
U-17 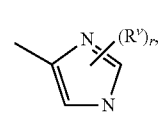
U-18 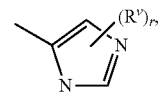
U-19 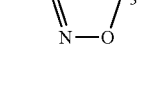
U-20 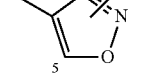
U-21 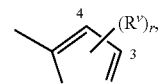
U-22 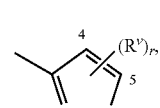
U-23 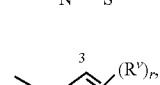
U-24 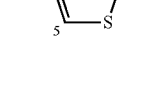
U-25 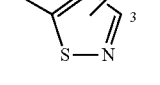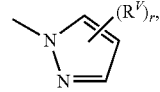

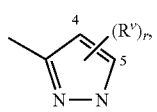  U-26
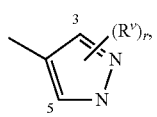  U-27
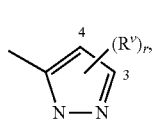  U-28
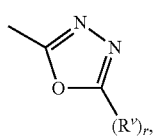  U-29
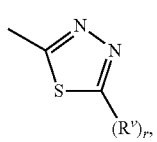  U-30
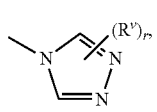  U-31
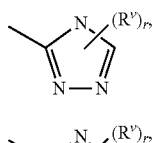  U-32
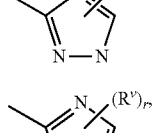  U-33
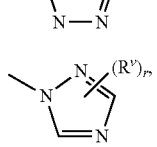  U-34
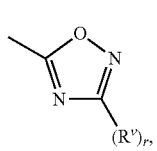  U-35
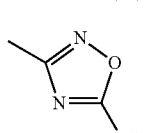  U-36
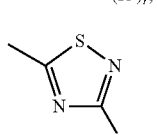  U-37
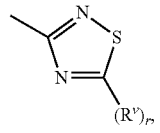  U-38
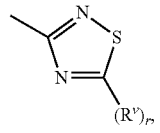  U-39
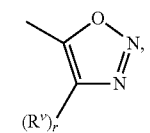  U-40
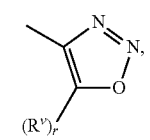  U-41
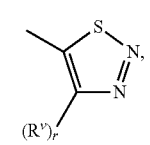  U-42
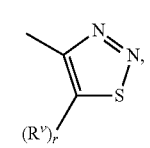  U-43
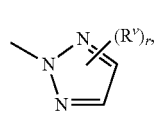  U-44
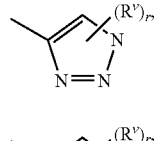  U-45
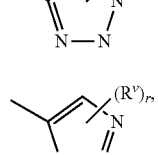  U-46
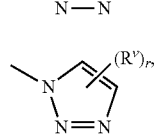  U-47
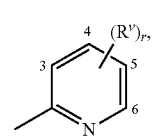  U-48
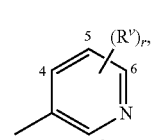  U-49
U-50

-continued

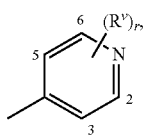 U-51

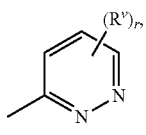 U-52

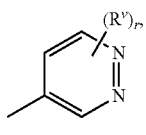 U-53

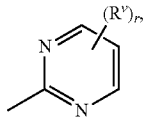 U-54

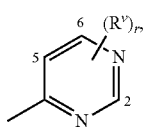 U-55

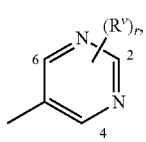 U-56

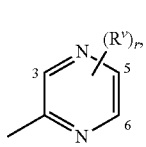 U-57

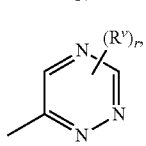 U-58

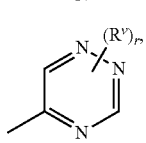 U-59

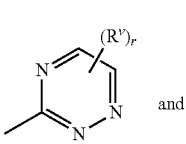 U-60 and

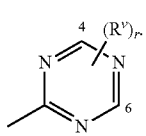 U-61

As noted above, $Q^1$ and $Q^2$ can be (among others) an 8- to 10-membered heteroaromatic bicyclic ring system optionally substituted with one or more substituents selected from a group of substituents as defined in the Summary of the Invention (i.e. $R^7$ and $R^{10}$). Examples of an 8- to 10-membered heteroaromatic bicyclic ring system optionally substituted with from one or more substituents include the rings U-62 through U-100 illustrated in Exhibit 2 wherein $R^v$ is any substituent as defined in the Summary of the Invention for $Q^1$ or $Q^2$, and r is typically an integer from 0 to 5.

Exhibit 2

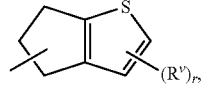 U-62

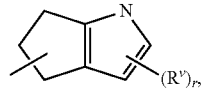 U-63

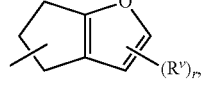 U-64

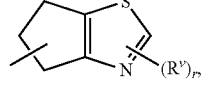 U-65

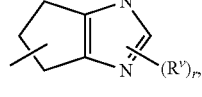 U-66

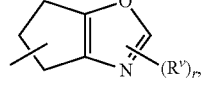 U-67

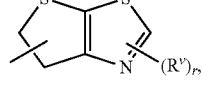 U-68

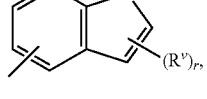 U-69

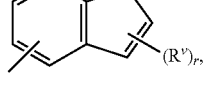 U-70

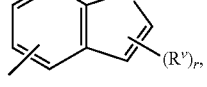 U-71

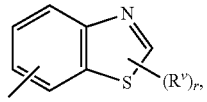 U-72

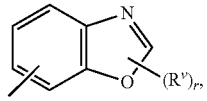 U-73

-continued
U-74 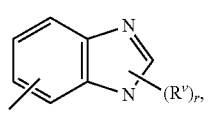
U-75 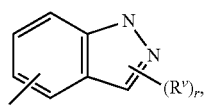
U-76 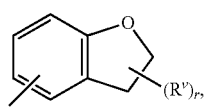
U-77 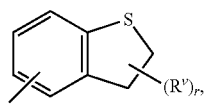
U-78 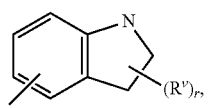
U-79 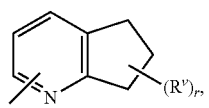
U-80 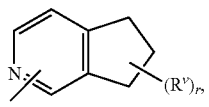
U-81 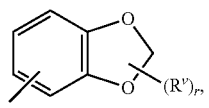
U-82 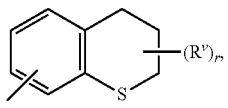
U-83 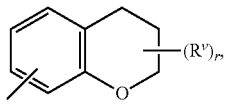
U-84 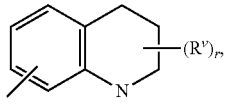
U-85 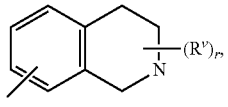
U-86 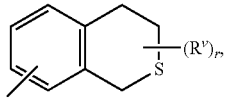
U-87 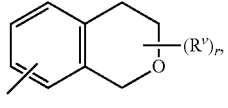
-continued
U-88 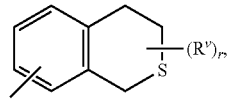
U-89 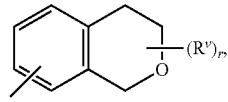
U-90 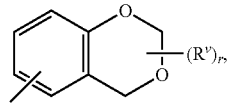
U-91 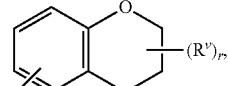
U-92 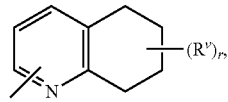
U-93 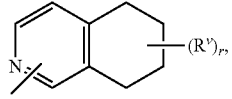
U-94 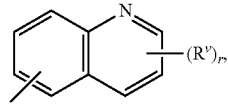
U-95 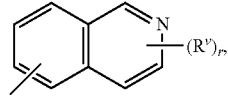
U-96 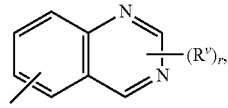
U-97 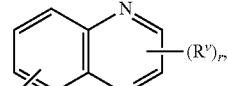
U-98 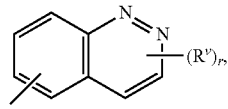
U-99 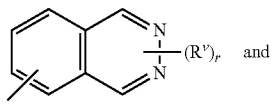 and
U-100 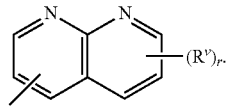
Although $R^v$ groups are shown in the structures U-1 through U-100, it is noted that they do not need to be present since they are optional substituents. Note that when $R^v$ is H when attached to an atom, this is the same as if said atom is unsubstituted. The nitrogen atoms that require substitution to fill their valence are substituted with H or R$^v$. Note that when the attachment point between (R$^v$)$_r$ and the U group is illustrated as floating, (R$^v$)$_r$ can be attached to any available carbon atom or nitrogen atom of the U group. Note that when the attachment point on the U group is illustrated as floating, the U group can be attached to the remainder of Formula 1 through any available carbon or nitrogen of the U group by replacement of a hydrogen atom. Note that some U groups can only be substituted with less than 4 R$^v$ groups (e.g., U-2 through U-5, U-7 through U-48, and U-52 through U-61).

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how separate, enrich, and/or to selectively prepare said stereoisomers. The compounds of the invention may be present as a mixture of stereoisomers, individual stereoisomers or as an optically active form. Particularly when R$^4$ and R$^5$ are each H, the C(O)N(Q$^2$)(R$^6$) and Q$^1$ substituents are typically mostly in the thermodynamically preferred trans configuration on the cyclic amide ring.

For example, the C(O)N(Q$^2$)(R$^6$) moiety (i.e. when each of Y$^1$ and Y$^2$ are O; and J is —CR$^2$R$^3$—; and R$^2$ is H; and R$^3$ is H) bonded to the carbon at the 3-position of the cyclic amide ring and -A-Q$^1$ (bonded to the carbon at the 4-position of the cyclic amide ring) are generally found in the trans configuration. The carbon atoms at both the 3- and 4-positions of each possess a chiral center. The most prevalant pair of enantiomers are depicted as Formula 1' and Formula 1". While this invention pertains to all stereoisomers, the preferred enantiomer for biological operability is identified as Formula 1'. The skilled artisan will understand the designation or R or S at a particular chiral center is a function of the specific substitution pattern at that center. For the compounds of Formulae 1' and 1" may therefore be reversed depending on the value of the A variable. For a comprehensive discussion of all aspects of stereoisomerism, see Ernest L. Eliel and Samuel H. Wilen, *Stereochemistry of Organic Compounds*, John Wiley & Sons, 1994.

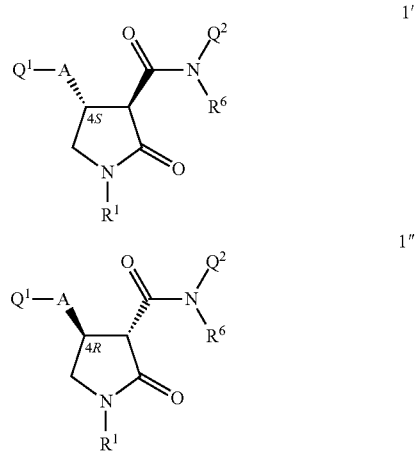

Molecular depictions drawn herein follow standard conventions for depicting stereochemistry. To indicate stereoconfiguration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the narrow end of the wedge is attached to the atom further away from the viewer.

Constant width lines indicate bonds with a direction opposite or neutral relative to bonds shown with solid or dashed wedges; constant width lines also depict bonds in molecules or parts of molecules in which no particular stereoconfiguration is intended to be specified.

This invention comprises racemic mixtures, for example, equal amounts of the enantiomers of Formulae 1' and 1". In addition, this invention includes compounds that are enriched compared to the racemic mixture in an enantiomer of Formula 1. Also included are the essentially pure enantiomers of compounds of Formula 1, for example, Formula 1' and Formula 1".

When enantiomerically enriched, one enantiomer is present in greater amounts than the other, and the extent of enrichment can be defined by an expression of enantiomeric excess ("ee"), which is defined as (2x−1)·100%, where x is the mole fraction of the dominant enantiomer in the mixture (e.g., an ee of 20% corresponds to a 60:40 ratio of enantiomers).

Preferably the compositions of this invention have at least a 50% enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Compounds of Formula 1 can comprise additional chiral centers. For example, substituents and other molecular constituents such as R$^7$ and R$^{10}$ may themselves contain chiral centers. This invention comprises racemic mixtures as well as enriched and essentially pure stereoconfigurations at these additional chiral centers.

Compounds of this invention can exist as one or more conformational isomers due to restricted rotation about the amide bond (e.g., C(O)N(Q$^2$)(R$^6$) when Y$^1$ is O) in Formula 1.

This invention comprises mixtures of conformational isomers. In addition, this invention includes compounds that are enriched in one conformer relative to others.

Compounds of Formula 1 typically exist in more than one form, and Formula 1 thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Embodiments of the present invention as described in the Summary of the Invention include (where Formula 1 as used in the following Embodiments includes N-oxides and salts thereof):

Embodiment 1

A compound of Formula 1 wherein A is —CH$_2$—, —CH$_2$O—, —CH$_2$N—, —OCH$_2$—, —NCH$_2$—, —CH=CH—, —C≡C—, —NH—, —O—, —S—, —SO— or —SO$_2$— wherein the free bond projecting to the left indicates the connecting point of A to Q$^1$ and the free bond projecting to the right indicates the connecting point of A to the remainder of Formula 1.

Embodiment 2

A compound of Embodiment 1 wherein A is —CH$_2$—, —CH$_2$O—, —CH$_2$N—, —OCH$_2$—, —NCH$_2$—, —CH=CH—, —C≡C—, —N— or —O—.

Embodiment 3

A compound of Embodiment 2 wherein A is —CH$_2$—.

Embodiment 4

A compound of Formula 1 or any one of Embodiment 1 through Embodiment 3 wherein Q$^1$ is a 5- to 6-membered heteroaromatic ring or an 8- to 10-membered heteroaromatic bicyclic ring system, each ring or ring system optionally substituted with up to 5 substituents independently selected from R$^7$ on carbon atom ring members and selected from R$^9$ on nitrogen atom ring members.

Embodiment 5

A compound of Formula 1 or any one of Embodiment 1 through Embodiment 3 wherein Q$^1$ is a phenyl ring or a naphthalenyl ring system, each ring or ring system optionally substituted with up to 4 substituents independently selected from R$^7$.

Embodiment 6

A compound of Embodiment 5 wherein Q$^1$ is a phenyl ring substituted with up to 2 substituents independently selected from R$^7$.

Embodiment 7

A compound of Embodiment 6 wherein $Q^1$ is a phenyl ring substituted with 1 substituent independently selected from $R^7$.

Embodiment 8

A compound of Formula 1 or any one of Embodiment 1 through Embodiment 7 wherein when $Q^2$ is a 5- to 6-membered heteroaromatic ring or an 8- to 10-membered heteroaromatic bicyclic ring system, each ring or ring system optionally substituted with up to 5 substituents independently selected from $R^{10}$ on carbon atom ring members and selected from $R^{11}$ on nitrogen atom ring members.

Embodiment 9

A compound of Formula 1 or any one of Embodiment 1 through Embodiment 7 wherein $Q^2$ is a phenyl ring substituted with up to 4 substituents independently selected from $R^{10}$.

Embodiment 10

A compound of Embodiment 9 wherein $Q^2$ is a phenyl ring substituted with up to 3 substituents independently selected from $R^{10}$ Embodiment 11.

A compound of Embodiment 10 wherein $Q^2$ is a phenyl ring substituted with up to 2 substituents independently selected from $R^{10}$ Embodiment 12.

A compound of Embodiment 9 wherein $Q^2$ is a phenyl ring having at least one substituent selected from $R^{10}$ at an ortho position (and optionally other substituents).

Embodiment 13

A compound of Embodiment 12 wherein $Q^2$ is a phenyl ring having 2 substituents selected from $R^{10}$ and one of the said substituents is at an ortho position and the other said substituent is at meta or para position.

Embodiment 14

A compound of Embodiment 10 wherein when $Q^2$ is a phenyl ring substituted with three substituents selected from $R^{10}$ and the three substituents are at an ortho (e.g., 2-), meta (e.g., 3-) and para (e.g., 4-) positions (of the phenyl ring).

Embodiment 15

A compound of Formula 1 or any one of Embodiment 1 through Embodiment 14 wherein $Y^1$ is O.

Embodiment 16

A compound of Formula 1 or any one of Embodiment 1 through Embodiment 15 wherein $Y^2$ is O.

Embodiment 17

A compound of Formula 1 or any one of Embodiment 1 through Embodiment 16 wherein $Y^1$ and $Y^2$ are both O.

Embodiment 18

A compound of Formula 1 or any one of Embodiment 1 through Embodiment 17 wherein J is —$CR^2R^3$—.

Embodiment 19

A compound of Formula 1 or any one of Embodiment 1 through Embodiment 17 wherein J is —$CR^2R^3$—$CR^{2a}R^{3a}$—.

Embodiment 20

A compound of Formula 1 or any one of Embodiment 1 through Embodiment 19 wherein $R^1$ is H, hydroxy, amino, cyano, formyl, $C_3$-$C_8$ alkylcarbonylalkyl, —C($C_1$-$C_4$ alkyl)=N—O($C_1$-$C_4$ alkyl), —C(O)$NH_2$, $C_1$-$C_6$ alkyl, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_3$-$C_8$ alkoxyalkoxyalkyl or $C_2$-$C_8$ haloalkoxyalkyl.

Embodiment 21

A compound of Embodiment 20 wherein $R^1$ is H, hydroxy, amino, $C_1$-$C_6$ alkyl, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl or $C_4$-$C_8$ cycloalkylalkyl.

Embodiment 22

A compound of Embodiment 21 wherein $R^1$ is H, $C_1$-$C_6$ alkyl or $C_1$-$C_6$ haloalkyl.

Embodiment 23

A compound of Embodiment 22 wherein $R^1$ is H Me Et or $CHF_2$.

Embodiment 23

A compound of Embodiment 22 wherein $R^1$ is H, Me, Et or $CHF_2$.

Embodiment 24

A compound of Embodiment 23 wherein $R^1$ is H, Me or Et.

Embodiment 25

A compound of Embodiment 24 wherein $R^1$ is H.

Embodiment 26

A compound of Embodiment 24 wherein $R^1$ is Me.

Embodiment 27

A compound of Formula 1 or any one of Embodiment 1 through Embodiment 26 wherein $R^2$ is H or $CH_3$.

Embodiment 28

A compound of Embodiment 27 wherein $R^2$ is H.

Embodiment 29

A compound of Formula 1 or any one of Embodiment 1 through Embodiment 28 wherein $R^3$ is H or $CH_3$.

Embodiment 30

A compound of Embodiment 29 wherein $R^3$ is H.

Embodiment 31

A compound of Formula 1 or any one of Embodiment 1 through Embodiment 30 wherein $R^{2a}$ is H or $CH_3$.

Embodiment 32

A compound of Embodiment 31 wherein $R^{2a}$ is H.

Embodiment 33

A compound of Formula 1 or any one of Embodiment 1 through Embodiment 32 wherein $R^{3a}$ is H or $CH_3$.

Embodiment 34

A compound of Embodiment 33 wherein $R^{3a}$ is H.

Embodiment 35

A compound of Formula 1 or any one of Embodiment 1 through Embodiment 34 wherein $R^4$ is H or $CH_3$.

Embodiment 36

A compound of Embodiment 35 wherein $R^4$ is H.

Embodiment 37

A compound of Formula 1 or any one of Embodiment 1 through Embodiment 36 wherein $R^5$ is H or $CH_3$.

Embodiment 38

A compound of Embodiment 37 wherein $R^5$ is H.

Embodiment 39

A compound of Formula 1 or any one of Embodiment 1 through Embodiment 38 wherein $R^6$ is H, hydroxy, amino, $C_1$-$C_6$ alkyl, $C_1$-$C_6$ haloalkyl, $C_2$-$C_6$ alkenyl, $C_3$-$C_6$ alkynyl, $C_2$-$C_8$ alkoxyalkyl, $C_3$-$C_8$ alkoxyalkoxyalkyl or $C_2$-$C_8$ haloalkoxyalkyl.

Embodiment 40

A compound of Embodiment 39 wherein $R^6$ is H or $CH_3$.

Embodiment 41

A compound of Embodiment 40 wherein $R^6$ is H.

Embodiment 42

A compound of Formula 1 or any one of Embodiment 1 through Embodiment 41 wherein each $R^7$ is independently halogen, cyano, nitro, $C_1$-$C_8$ alkyl, $C_2$-$C_8$ cyanoalkyl, $C_1$-$C_8$ cyanoalkoxy, $C_1$-$C_8$ haloalkyl, $C_2$-$C_8$ alkenyl, $C_2$-$C_8$ haloalkenyl, $C_2$-$C_8$ alkynyl, $C_2$-$C_8$ haloalkynyl, $C_1$-$C_8$ nitroalkyl, $C_2$-$C_8$ nitroalkenyl, $C_2$-$C_8$ alkoxyalkyl, $C_3$-$C_8$ alkoxyalkoxyalkyl, $C_2$-$C_8$ haloalkoxyalkyl, $C_3$-$C_8$ cycloalkyl, $C_3$-$C_8$ halocycloalkyl, $C_4$-$C_{10}$ cycloalkylalkyl, $C_4$-$C_{10}$ alkylcycloalkyl, $C_1$-$C_8$ alkoxy, $C_1$-$C_8$ haloalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_1$-$C_8$ alkylthio, $C_1$-$C_8$ haloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, hydroxy, formyl, $C_2$-$C_8$ alkylcarbonyl, $C_2$-$C_8$ alkylcarbonyloxy, $C_1$-$C_8$ alkylsulfonyloxy, $C_1$-$C_8$ haloalkylsulfonyloxy, amino, $C_1$-$C_4$ alkylamino, $C_2$-$C_4$ dialkylamino, formylamino, $C_2$-$C_4$ alkylcarbonylamino, —$SF_5$, —SCN, $C_3$-$C_{12}$ trialkylsilyl, trimethylsilylmethyl or trimethylsilylmethoxy.

Embodiment 43

A compound of Embodiment 42 wherein each $R^7$ is independently halogen, cyano, $C_1$-$C_2$ alkyl, $C_1$-$C_3$ haloalkyl or $C_1$-$C_3$ alkylsulfonyl.

Embodiment 44

A compound of Embodiment 43 each wherein $R^7$ is independently halogen or $C_1$-$C_2$ haloalkyl.

Embodiment 45

A compound of Embodiment 44 wherein each $R^7$ is independently halogen or $CF_3$.

Embodiment 46

A compound of Embodiment 45 wherein each $R^7$ is independently F, Cl or $CF_3$.

Embodiment 47

A compound of Formula 1 or any one of Embodiment 1 through Embodiment 46 wherein each $R^{10}$ is independently halogen, hydroxy, cyano, nitro, $C_1$-$C_8$ alkyl, $C_2$-$C_8$ cyanoalkyl, $C_1$-$C_8$ cyanoalkoxy, $C_1$-$C_8$ haloalkyl, $C_2$-$C_8$ alkenyl, $C_2$-$C_8$ haloalkenyl, $C_2$-$C_8$ alkynyl, $C_2$-$C_8$ haloalkynyl, $C_1$-$C_8$ nitroalkyl, $C_2$-$C_8$ nitroalkenyl, $C_2$-$C_8$ alkoxyalkyl, $C_3$-$C_8$ alkoxyalkoxyalkyl, $C_2$-$C_8$ haloalkoxyalkyl or $C_3$-$C_8$ cycloalkyl.

Embodiment 48

A compound of Embodiment 47 wherein each $R^{10}$ is independently halogen, cyano, nitro, $C_1$-$C_2$ alkyl, $C_1$-$C_3$ haloalkyl or $C_1$-$C_3$ alkylsulfonyl.

Embodiment 49

A compound of Embodiment 48 wherein each $R^{10}$ is independently halogen or $C_1$-$C_2$ haloalkyl.

Embodiment 50

A compound of Embodiment 49 wherein each $R^{10}$ is independently halogen or $CF_3$.

Embodiment 51

A compound of Embodiment 50 wherein each $R^{10}$ is independently F or $CF_3$.

Embodiment 52

A compound of Embodiment 51 wherein each $R^{10}$ is independently F.

Embodiment 53

A compound of any one Embodiments 1, 2 or 4 through 52 wherein A is —$CH_2$—, —$(CH_2)_2C(=O)NH$—, —$CH_2CH_2$—, —$C(=O)NH$—, —$CH_2NH$—, —$OCH_2$—, —$NHCH_2$—, —CH=CH—, —C≡C—, —N—, —O—, —S—, —SO— or —$SO_2$— wherein the free bond projecting to the left indicates the connecting point of A to $Q^1$ and the free bond projecting to the right indicates the connecting point of A to the remainder of Formula 1.

Embodiment 54

A compound of Embodiment 54 wherein A is —$CH_2$—, —$CH_2CH_2$—, —$C(=O)NH$—, —CH=CH— or —C≡C— wherein the bond projecting to the left is connected to the $Q^1$ moiety, and the bond projecting to the right is connected to the remainder of Formula 1.

Embodiment 55

A compound of Embodiment 54 wherein A is —$CH_2$—, —$CH_2CH_2$—, —CH=CH— or —C≡C—.

Embodiment 56

A compound of Embodiment 55 wherein A is —$CH_2$—.

Embodiment 57

A compound of Embodiment 55 wherein A is —$CH_2CH_2$—.

Embodiment 58

A compound of Embodiment 56 wherein A is —CH=CH—.

Embodiment 59

A compound of Embodiment 56 wherein A is —C≡C—.

Embodiment 60

A compound of Embodiment 1 wherein $Q^1$ is an 8- to 10-membered heteroaromatic bicyclic ring system, each ring system containing ring members selected from carbon atoms and 1 to 4 heteroatoms independently selected from up to 2 O and up to 2 N atoms, wherein up to 3 carbon ring members are independently selected from C(=O) and C(=S), each ring system optionally substituted with up to 4 substituents independently selected from $R^7$ on carbon atom ring members and selected from $R^9$ on nitrogen atom ring members.

Embodiment 61

A compound of Embodiment 60 wherein $Q^1$ is an 8- to 9-membered heteroaromatic bicyclic ring system, each ring system containing ring members selected from carbon atoms and 1 to 4 heteroatoms independently selected from up to 2 O atoms, each ring system optionally substituted with up to 4 substituents independently selected from $R^7$ on carbon atom ring members.

Embodiment 62

A compound of Embodiment 61 wherein $Q^1$ is an 9-membered heteroaromatic bicyclic ring system containing ring members selected from carbon atoms and 1 to 4 heteroatoms independently selected from up to 2 O atoms, each ring system optionally substituted with up to 4 substituents independently selected from $R^7$ on carbon atom ring members.

Embodiment 63

A compound of Embodiment 62 wherein $Q^1$ is an 9-membered heteroaromatic bicyclic ring system containing ring members selected from carbon atoms and 2 O atoms, system optionally substituted with up to 3 substituents independently selected from $R^7$ on carbon atom ring members (i.e. U-81 in Exhibit 2).

Embodiment 64

A compound of Embodiment 63 wherein $Q^1$ is U-81A;

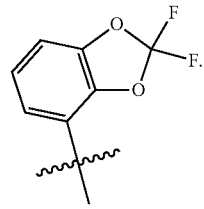

U-81A

Embodiment 65

A compound of Formula 1 or any one of Embodiments 1 through 3, 5 or 8 through 64 wherein $Q^1$ is a phenyl ring optionally substituted with 1 to 4 substituents independently selected from $R^7$; or a 5- to 6-membered heteroaromatic ring containing ring members selected from carbon atoms and 1 to 4 heteroatoms independently selected from up to 2 O, up to 2 S and up to 4 N atoms, optionally substituted with up to 4 substituents independently selected from $R^7$ on carbon atom ring members and selected from $R^9$ on nitrogen atom ring members.

Embodiment 66

A compound of Formula 1 or any one of Embodiments 1 through 7 or 15 through 65 wherein $Q^2$ is a phenyl ring optionally substituted with up to 5 substituents independently selected from $R^{10}$; or a 5- to 6-membered fully unsaturated heterocyclic ring, each ring containing ring members selected from carbon atoms and 1 to 4 heteroatoms independently selected from up to 2 O, up to 2 S and up to 4 N atoms, each ring or ring system optionally substituted with up to 5 substituents independently selected from $R^{11}$ on carbon atom ring members and selected from $R^{11}$ on nitrogen atom ring members.

Embodiment 67

A compound of Embodiment 66 wherein $Q^2$ is a phenyl ring optionally substituted with up to 5 substituents independently selected from $R^{10}$; or a 6-membered fully unsaturated heterocyclic ring, each ring containing ring members selected from carbon atoms and 1 to 4 heteroatoms independently selected from up to 4 N atoms, each ring or ring system optionally substituted with up to 5 substituents independently selected from $R^{11}$ on carbon atom ring members.

Embodiment 68

A compound of Embodiment 67 wherein $Q^2$ is a phenyl ring optionally substituted with up to 4 substituents independently selected from $R^{10}$; or a pyridyl ring, optionally substituted with up to 4 substituents independently selected from $R^{11}$ on carbon atom ring members.

Embodiment 69

A compound of Embodiment 68 wherein $Q^2$ is a 3-pyridyl ring optionally substituted with up to 3 substituents independently selected from $R^{10}$ on carbon atom ring members.

Embodiment 70

A compound of Embodiment 69 wherein $Q^2$ is a 3-pyridyl ring optionally substituted with up to 3 substituents independently selected from $C_1$-$C_8$ alkyl or $C_1$-$C_8$ haloalkyl.

Embodiment 71

A compound of Formula 1 wherein A is —CH$_2$—, —CH$_2$O—, —CH$_2$NH—, —OCH$_2$—, —NHCH$_2$—, —CH=CH—, —C≡C—, —NH—, —O—, —S—, —SO— or —SO$_2$— wherein the free bond projecting to the left indicates the connecting point of A to $Q^1$ and the free bond projecting to the right indicates the connecting point of A to the remainder of Formula 1.

Embodiment 72

A compound of Formula 2 wherein A is wherein A is —CH$_2$—, —CH$_2$O—, —CH$_2$NH—, —OCH$_2$—, —NHCH$_2$—, —CH=CH—, —C≡C—, —NH— or —O—.

Embodiment 73

A compound of Formula 1 wherein A is selected from —ON=CH—, —ON=C(CH$_3$)—, —NHN=CH—, —NHN=C(CH$_3$)—, —N=CH—, —N=C(CH$_3$)—, —CH=NO—, —C(CH$_3$)=NO—, —CH=NNH—, —C(CH$_3$)=NNH—, —CH=N—, —C(CH$_3$)=N—, —CH$_2$CH$_2$CH$_2$—, —CH$_2$CH$_2$—, —CH$_2$—, —CF$_2$—, —C(=O)—, —CH=CH—, —CH=CHCH$_2$—, —CH$_2$CH=CH—, —C≡C—, —C≡CCH$_2$—, —CH$_2$C≡C—, —CH$_2$CH$_2$O—, —CH$_2$O—, —O—, —OCH$_2$CH$_2$—, —OCH$_2$—, —CH$_2$CH$_2$S—, —CH$_2$S—, —S—, —SO—, —SO$_2$—, —SCH$_2$CH$_2$—, —SCH$_2$—, —CH$_2$CH$_2$NH—, —CH$_2$NH—, —NH—, —NHCH$_2$— and —NHCH$_2$CH$_2$—, wherein the bond projecting to the left is connected to the $Q^1$ moiety, and the bond projecting to the right is connected to the remainder of Formula 1.

Embodiment 74

A compound of Embodiment 73 wherein A is selected from —ON=CH—, —ON=C(CH$_3$)—, —NHN=CH—, —NHN=C(CH$_3$)—, —N=CH—, —N=C(CH$_3$)—, —CH=NO—, —C(CH$_3$)=NO—, —CH=NNH—, —C(CH$_3$)=NNH—, —CH=N— and —C(CH$_3$)=N—.

Embodiment 75

A compound of Embodiment 74 wherein A is selected from —ON=CH—, —ON=C(CH$_3$)—, —NHN=CH—, —NHN=C(CH$_3$)—, —N=CH—, and —N=C(CH$_3$)—.

Embodiment 76

A compound of Embodiment 74 wherein A is selected from —CH=NO—, —C(CH$_3$)=NO—, —CH=NNH—, —C(CH$_3$)=NNH—, —CH=N— and —C(CH$_3$)=N—.

Embodiment 77

A compound of Formula 1 wherein $R^{15}$ is other than $C_4$-$C_8$ cycloalkylalkyl.

Embodiments of this invention, including Embodiments 1 through 77 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-77 above as well as any other embodiments described herein, and any combination thereof, pertain to the compositions and methods of the present invention.

Combinations of Embodiments 1-77 are illustrated by:

Embodiment A

A compound of Formula 1 wherein

A is —CH$_2$—, —CH$_2$O—, —CH$_2$NH—, —OCH$_2$—, —NHCH$_2$—, —CH=CH—, —C≡C—, —NH— or —O— wherein the free bond projecting to the left indicates the connecting point of A to $Q^1$ and the free bond projecting to the right indicates the connecting point of A to the remainder of Formula 1;

$Q^1$ is a phenyl ring substituted with up to 2 substituents independently selected from $R^7$;

$Q^2$ is a phenyl ring substituted with up to 3 substituents independently selected from $R^{10}$;

$Y^1$ and $Y^2$ are both O; and J is —CR$^2$R$^3$—.

Embodiment B

A compound of Formula 1 wherein
A is —$CH_2$—, —$CH_2O$—, —$CH_2NH$—, —$OCH_2$—, —$NHCH_2$—, —CH=CH—, —C≡C—, —NH— or —O— wherein the free bond projecting to the left indicates the connecting point of A to $Q^1$ and the free bond projecting to the right indicates the connecting point of A to the remainder of Formula 1;
$Q^1$ is a phenyl ring substituted with up to 2 substituents independently selected from $R^7$;
$Q^2$ is a phenyl ring substituted with up to 3 substituents independently selected from $R^{10}$;
$Y^1$ and $Y^2$ are both O; and
J is —$CR^2R^3$—$CR^{2a}R^{3a}$—.

Embodiment C

A compound of Embodiment A wherein
A is —$CH_2$—;
$R^1$ is H, Me or Et;
$R^2$ is H;
$R^3$ is H;
$R^4$ is H;
$R^5$ is H;
$R^6$ is H;
$R^7$ is independently is independently halogen, cyano, nitro, $C_1$-$C_8$ alkyl, $C_2$-$C_8$ cyanoalkyl, $C_1$-$C_8$ cyanoalkoxy, $C_1$-$C_8$ haloalkyl, $C_2$-$C_8$ alkenyl, $C_2$-$C_8$ haloalkenyl, $C_2$-$C_8$ alkynyl, $C_2$-$C_8$ haloalkynyl, $C_1$-$C_8$ nitroalkyl, $C_2$-$C_8$ nitroalkenyl, $C_2$-$C_8$ alkoxyalkyl, $C_3$-$C_8$ alkoxyalkoxyalkyl, $C_2$-$C_8$ haloalkoxyalkyl, $C_3$-$C_8$ cycloalkyl, $C_3$-$C_8$ halocycloalkyl, $C_4$-$C_{10}$ cycloalkylalkyl, $C_4$-$C_{10}$ alkylcyclolalkyl, $C_1$-$C_8$ alkoxy, $C_1$-$C_8$ haloalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_1$-$C_8$ alkylthio, $C_1$-$C_8$ haloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, hydroxy, formyl, $C_2$-$C_8$ alkylcarbonyl, $C_2$-$C_8$ alkylcarbonyloxy, $C_1$-$C_8$ alkylsulfonyloxy, $C_1$-$C_8$ haloalkylsulfonyloxy, amino, $C_1$-$C_4$ alkylamino, $C_2$-$C_4$ dialkylamino, formylamino, $C_2$-$C_4$ alkylcarbonylamino, —$SF_5$, —SCN, $C_3$-$C_{12}$ trialkylsilyl, trimethylsilylmethyl or trimethylsilylmethoxy; and
$R^{10}$ is independently halogen, cyano, nitro, $C_1$-$C_2$ alkyl, $C_1$-$C_3$ haloalkyl or $C_1$-$C_3$ alkylsulfonyl.

Embodiment D

A compound of Embodiment B wherein
A is —$CH_2$—;
$R^1$ is H, Me or Et;
$R^2$ is H;
$R^3$ is H;
$R^{2a}$ is H;
$R^{3a}$ is H;
$R^4$ is H;
$R^5$ is H;
$R^6$ is H;
$R^7$ is independently is independently halogen, cyano, nitro, $C_1$-$C_8$ alkyl, $C_2$-$C_8$ cyanoalkyl, $C_1$-$C_8$ cyanoalkoxy, $C_1$-$C_8$ haloalkyl, $C_2$-$C_8$ alkenyl, $C_2$-$C_8$ haloalkenyl, $C_2$-$C_8$ alkynyl, $C_2$-$C_8$ haloalkynyl, $C_1$-$C_8$ nitroalkyl, $C_2$-$C_8$ nitroalkenyl, $C_2$-$C_8$ alkoxyalkyl, $C_3$-$C_8$ alkoxyalkoxyalkyl, $C_2$-$C_8$ haloalkoxyalkyl, $C_3$-$C_8$ cycloalkyl, $C_3$-$C_8$ halocycloalkyl, $C_4$-$C_{10}$ cycloalkylalkyl, $C_4$-$C_{10}$ alkylcyclolalkyl, $C_1$-$C_8$ alkoxy, $C_1$-$C_8$ haloalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_1$-$C_8$ alkylthio, $C_1$-$C_8$ haloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, hydroxy, formyl, $C_2$-$C_8$ alkylcarbonyl, $C_2$-$C_8$ alkylcarbonyloxy, $C_1$-$C_8$ alkylsulfonyloxy, $C_1$-$C_8$ haloalkylsulfonyloxy, amino, $C_1$-$C_4$ alkylamino, $C_2$-$C_4$ dialkylamino, formylamino, $C_2$-$C_4$ alkylcarbonylamino, —$SF_5$, —SCN, $C_3$-$C_{12}$ trialkylsilyl, trimethylsilylmethyl or trimethylsilylmethoxy; and
$R^{10}$ is independently halogen, cyano, nitro, $C_1$-$C_2$ alkyl, $C_1$-$C_3$ haloalkyl or $C_1$-$C_3$ alkylsulfonyl.

Embodiment E

A compound of Embodiment C wherein
each $R^7$ is independently halogen, cyano, $C_1$-$C_2$ alkyl, $C_1$-$C_3$ haloalkyl or $C_1$-$C_3$ alkylsulfonyl; and each $R^{10}$ is independently halogen or $C_1$-$C_2$ haloalkyl.

Embodiment F

A compound of Embodiment E wherein
$Q^1$ is a phenyl ring substituted with 1 substituent independently selected from $R^7$;
$Q^2$ is a phenyl ring having 2 substituents selected from $R^{10}$ and one of the said substituents is at an ortho position and the other said substituent is at meta or para position.

Embodiment G

A compound of Embodiment E wherein
$Q^2$ is a phenyl ring substituted with three substituents selected from $R^{10}$ and the three substituents are at an ortho, meta and para positions of the phenyl ring.

Embodiment H

A compound of Formula 1 wherein
A is selected from —ON=CH—, —ON=C($CH_3$)—, —NHN=CH—, —NHN=C($CH_3$)—, —N=CH—, —N=C($CH_3$)—, —CH=NO—, —C($CH_3$)=NO—, —CH=NNH—, —C($CH_3$)=NNH—, —CH=N—, —C($CH_3$)=N—, —$CH_2CH_2CH_2$—, —$CH_2CH_2$—, —$CH_2$—, —$CF_2$—, —C(=O)—, —CH=CH—, —CH=CHCH_2—, —$CH_2$CH=CH—, —C≡C—, —C≡CCH$_2$—, —$CH_2$C≡C—, —$CH_2CH_2O$—, —$CH_2O$—, —O—, —$OCH_2CH_2$—, —$OCH_2$—, —$CH_2CH_2S$—, —$CH_2S$—, —S—, —SO—, —$SO_2$—, —$SCH_2CH_2$—, —$SCH_2$—, —$CH_2CH_2NH$—, —$CH_2NH$—, —NH—, —$NHCH_2$— and —$NHCH_2CH_2$—, wherein the bond projecting to the left is connected to the $Q^1$ moiety, and the bond projecting to the right is connected to the remainder of Formula 1;
$Q^1$ is a phenyl ring optionally substituted with 1 to 4 substituents independently selected from $R^7$; or a 5- to 6-membered heteroaromatic ring containing ring members selected from carbon atoms and 1 to 4 heteroatoms independently selected from up to 2 O, up to 2 S and up to 4 N atoms, optionally substituted with up to 4 substituents independently selected from $R^7$ on carbon atom ring members and selected from $R^9$ on nitrogen atom ring members;

$Q^2$ is a phenyl ring optionally substituted with up to 5 substituents independently selected from $R^{10}$; or a 5- to 6-membered fully unsaturated heterocyclic ring, each ring containing ring members selected from carbon atoms and 1 to 4 heteroatoms independently selected from up to 2 O, up to 2 S and up to 4 N atoms, each ring or ring system optionally substituted with up to 5 substituents independently selected from $R^{11}$ on carbon atom ring members and selected from $R^{11}$ on nitrogen atom ring members;

$Y^1$ and $Y^2$ are both O;

$R^1$ is H, hydroxy, amino, cyano, formyl, $C_3$-$C_8$ alkylcarbonylalkyl, —C($C_1$-$C_4$ alkyl)=N—O($C_1$-$C_4$ alkyl), —C(O)NH$_2$, $C_1$-$C_6$ alkyl, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_3$-$C_8$ alkoxyalkoxyalkyl or $C_2$-$C_8$ haloalkoxyalkyl;

$R^6$ is H, hydroxy, amino, $C_1$-$C_6$ alkyl, $C_1$-$C_6$ haloalkyl, $C_2$-$C_6$ alkenyl, $C_3$-$C_6$ alkynyl, $C_2$-$C_8$ alkoxyalkyl, $C_3$-$C_8$ alkoxyalkoxyalkyl or $C_2$-$C_8$ haloalkoxyalkyl;

each $R^7$ is independently halogen, cyano, nitro, $C_1$-$C_8$ alkyl, $C_2$-$C_8$ cyanoalkyl, $C_1$-$C_8$ cyanoalkoxy, $C_1$-$C_8$ haloalkyl, $C_2$-$C_8$ alkenyl, $C_2$-$C_8$ haloalkenyl, $C_2$-$C_8$ alkynyl, $C_2$-$C_8$ haloalkynyl, $C_1$-$C_8$ nitroalkyl, $C_2$-$C_8$ nitroalkenyl, $C_2$-$C_8$ alkoxyalkyl, $C_3$-$C_8$ alkoxyalkoxyalkyl, $C_2$-$C_8$ haloalkoxyalkyl, $C_3$-$C_8$ cycloalkyl, $C_3$-$C_8$ halocycloalkyl, $C_4$-$C_{10}$ cycloalkylalkyl, $C_4$-$C_{10}$ alkylcyclolalkyl, $C_1$-$C_8$ alkoxy, $C_1$-$C_8$ haloalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_1$-$C_8$ alkylthio, $C_1$-$C_8$ haloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, hydroxy, formyl, $C_2$-$C_8$ alkylcarbonyl, $C_2$-$C_8$ alkylcarbonyloxy, $C_1$-$C_8$ alkylsulfonyloxy, $C_1$-$C_8$ haloalkylsulfonyloxy, amino, $C_1$-$C_4$ alkylamino, $C_2$-$C_4$ dialkylamino, formylamino, $C_2$-$C_4$ alkylcarbonylamino, —SF$_5$, —SCN, $C_3$-$C_{12}$ trialkylsilyl, trimethylsilylmethyl or trimethylsilylmethoxy; and each $R^{10}$ is independently halogen, hydroxy, cyano, nitro, $C_1$-$C_8$ alkyl, $C_2$-$C_8$ cyanoalkyl, $C_1$-$C_8$ cyanoalkoxy, $C_1$-$C_8$ haloalkyl, $C_2$-$C_8$ alkenyl, $C_2$-$C_8$ haloalkenyl, $C_2$-$C_8$ alkynyl, $C_2$-$C_8$ haloalkynyl, $C_1$-$C_8$ nitroalkyl, $C_2$-$C_8$ nitroalkenyl, $C_2$-$C_8$ alkoxyalkyl, $C_3$-$C_8$ alkoxyalkoxyalkyl, $C_2$-$C_8$ haloalkoxyalkyl or $C_3$-$C_8$ cycloalkyl.

Specific embodiments include compounds of Formula 1 selected from the group consisting of:

N-(2,3-difluorophenyl)-4-[(4-fluorophenyl)methyl]-2-oxo-3-pyrrolidinecarboxamide (Compound 13); and 4-[(3-chlorophenyl)methyl]-N-(2,3-difluorophenyl)-2-oxo-3-pyrrolidinecarboxamide (Compound 1).

This invention also relates to a method for controlling undesired vegetation comprising applying to the locus of the vegetation herbicidally effective amounts of the compounds of the invention (e.g., as a composition described herein). Of note as embodiments relating to methods of use are those involving the compounds of embodiments described above. Compounds of the invention are particularly useful for selective control of weeds in crops such as wheat, barley, maize, soybean, sunflower, cotton, oilseed rape and rice, and specialty crops such as sugarcane, citrus, fruit and nut crops.

Also noteworthy as embodiments are herbicidal compositions of the present invention comprising the compounds of embodiments described above.

This invention also includes a herbicidal mixture comprising (a) a compound selected from Formula 1, N-oxides, and salts thereof, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, hydantocidin, metam, methyldymron, oleic acid, oxaziclomefone, pelargonic acid and pyributicarb, and (b16) herbicide safeners; and salts of compounds of (b1) through (b16).

"Photosystem II inhibitors" (b1) are chemical compounds that bind to the D-1 protein at the $Q_B$-binding niche and thus block electron transport from $Q_A$ to $Q_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The $Q_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazon, nitriles such as bromoxynil and phenyl-pyridazines such as pyridate. Examples of photosystem II inhibitors include ametryn, amicarbazone, atrazine, bentazon, bromacil, bromofenoxim, bromoxynil, chlorbromuron, chloridazon, chlorotoluron, chloroxuron, cumyluron, cyanazine, daimuron, desmedipham, desmetryn, dimefuron, dimethametryn, diuron, ethidimuron, fenuron, fluometuron, hexazinone, ioxynil, isoproturon, isouron, lenacil, linuron, metamitron, methabenzthiazuron, metobromuron, metoxuron, metribuzin, monolinuron, neburon, pentanochlor, phenmedipham, prometon, prometryn, propanil, propazine, pyridafol, pyridate, siduron, simazine, simetryn, tebuthiuron, terbacil, terbumeton, terbuthylazine, terbutryn and trietazine. Of note is a compound of the invention mixed with atrazine, bromoxynil or metribuzin.

"AHAS inhibitors" (b2) are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for protein synthesis and cell growth. Examples of AHAS inhibitors include amidosulfuron, azimsulfuron, bensulfuron-methyl, bispyribac-sodium, cloransulam-methyl, chlorimuron-ethyl, chlorsulfuron, cinosulfuron, cyclosulfamuron, diclosulam, ethametsulfuron-methyl, ethoxysulfuron, flazasulfuron, florasulam, flucarbazone-sodium, flumetsulam, flupyrsulfuron-methyl, flupyrsulfuron-sodium, foramsulfuron, halosulfuron-methyl, imazamethabenzmethyl, imazamox, imazapic, imazapyr, imazaquin, imazethapyr, imazosulfuron, iodosulfuron-methyl (including sodium salt), iofensulfuron (2-iodo-N-[[(4-methoxy-6-methyl-1,3,5-triazin-2-yl)amino]carbonyl]benzenesulfonamide), mesosulfuron-methyl, metazosulfuron (3-chloro-4-(5,6-dihydro-5-methyl-1,4,2-dioxazin-3-yl)-N-[[(4,6-dimethoxy-2-pyrimidinyl)amino]carbonyl]-1-methyl-1H-pyrazole-5-sulfonamide), metosulam, metsulfuron-methyl, nicosulfuron, oxasulfuron, penoxsulam, primisulfuron-methyl, propoxycarbazone-sodium, propyrisulfuron (2-chloro-N-[[(4,6-dimethoxy-2-pyrimidinyl)amino]carbonyl]-6-propylimidazo[1,2-b]pyridazine-3-sulfonamide), prosulfuron, pyrazosulfuron-ethyl, pyribenzoxim, pyriftalid, pyriminobac-methyl, pyrithiobac-sodium, rimsulfuron, sulfometuron-methyl, sulfosulfuron, thiencarbazone, thifensulfuron-methyl, triafamone (N-[2-[(4,6-dimethoxy-1,3,5-triazin-2-yl)carbonyl]-6-fluorophenyl]-1,1-difluoro-N-methylmethanesulfonamide), triasulfuron, tribenuron-methyl, trifloxysulfuron (including sodium salt), triflusulfuron-methyl and tritosulfuron. Of note is a compound of the invention mixed with nicosulfuron, flupyrsulfuron or chlorimuron.

"ACCase inhibitors" (b3) are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include alloxydim, butroxydim, clethodim, clodinafop, cycloxydim, cyhalofop, diclofop, fenoxaprop, fluazifop, haloxyfop, pinoxaden, profoxydim, propaquizafop, quizalofop, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl. Of note is a compound of the invention mixed with pinoxaden or quizalofop.

Auxin is a plant hormone that regulates growth in many plant tissues. "Auxin mimics" (b4) are chemical compounds mimicking the plant growth hormone auxin, thus causing uncontrolled and disorganized growth leading to plant death in susceptible species. Examples of auxin mimics include aminocyclopyrachlor (6-amino-5-chloro-2-cyclopropyl-4-pyrimidinecarboxylic acid) and its methyl and ethyl esters and its sodium and potassium salts, aminopyralid, benazolin-ethyl, chloramben, clacyfos, clomeprop, clopyralid, dicamba, 2,4-D, 2,4-DB, dichlorprop, fluroxypyr, halauxifen (4-amino-3-chloro-6-(4-chloro-2-fluoro-3-methoxyphenyl)-2-pyridinecarboxylic acid), halauxifen-methyl (methyl 4-amino-3-chloro-6-(4-chloro-2-fluoro-3-methoxyphenyl)-2-pyridinecarboxylate), MCPA, MCPB, mecoprop, picloram, quinclorac, quinmerac, 2,3,6-TBA, triclopyr, and methyl 4-amino-3-chloro-6-(4-chloro-2-fluoro-3-methoxyphenyl)-5-fluoro-2-pyridinecarboxylate. Of note is a compound of the invention mixed with dicamba.

"EPSP synthase inhibitors" (b5) are chemical compounds that inhibit the enzyme, 5-enol-pyruvylshikimate-3-phosphate synthase, which is involved in the synthesis of aromatic amino acids such as tyrosine, tryptophan and phenylalanine. EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate).

"Photosystem I electron diverters" (b6) are chemical compounds that accept electrons from Photosystem I, and after several cycles, generate hydroxyl radicals. These radicals are extremely reactive and readily destroy unsaturated lipids, including membrane fatty acids and chlorophyll. This destroys cell membrane integrity, so that cells and organelles "leak", leading to rapid leaf wilting and desiccation, and eventually to plant death. Examples of this second type of photosynthesis inhibitor include diquat and paraquat.

"PPO inhibitors" (b7) are chemical compounds that inhibit the enzyme protoporphyrinogen oxidase, quickly resulting in formation of highly reactive compounds in plants that rupture cell membranes, causing cell fluids to leak out. Examples of PPO inhibitors include acifluorfen-sodium, azafenidin, benzfendizone, bifenox, butafenacil, carfentrazone, carfentrazone-ethyl, chlomethoxyfen, cinidon-ethyl, fluazolate, flufenpyr-ethyl, flumiclorac-pentyl, flumioxazin, fluoroglycofen-ethyl, fluthiacet-methyl, fomesafen, halosafen, lactofen, oxadiargyl, oxadiazon, oxyfluorfen, pentoxazone, profluazol, pyraclonil, pyraflufen-ethyl, saflufenacil, sulfentrazone, thidiazimin, trifludimoxazin (dihydro-1,5-dimethyl-6-thioxo-3-[2,2,7-trifluoro-3,4-dihydro-3-oxo-4-(2-propyn-1-yl)-2H-1,4-benzoxazin-6-yl]-1,3,5-triazine-2,4(1H,3H)-dione) and tiafenacil (methyl N-[2-[[2-chloro-5-[3,6-dihydro-3-methyl-2,6-dioxo-4-(trifluoromethyl)-1(2H)-pyrimidinyl]-4-fluorophenyl]thio]-1-oxopropyl]-β-alaninate).

"GS inhibitors" (b8) are chemical compounds that inhibit the activity of the glutamine synthetase enzyme, which plants use to convert ammonia into glutamine. Consequently, ammonia accumulates and glutamine levels decrease. Plant damage probably occurs due to the combined effects of ammonia toxicity and deficiency of amino acids required for other metabolic processes. The GS inhibitors include glufosinate and its esters and salts such as glufosinate-ammonium and other phosphinothricin derivatives, glufosinate-P ((2S)-2-amino-4-(hydroxymethylphosphinyl)butanoic acid) and bilanaphos.

"VLCFA elongase inhibitors" (b9) are herbicides having a wide variety of chemical structures, which inhibit the elongase. Elongase is one of the enzymes located in or near chloroplasts which are involved in biosynthesis of VLCFAs. In plants, very-long-chain fatty acids are the main constituents of hydrophobic polymers that prevent desiccation at the leaf surface and provide stability to pollen grains. Such herbicides include acetochlor, alachlor, anilofos, butachlor, cafenstrole, dimethachlor, dimethenamid, diphenamid, fenoxasulfone (3-[[(2,5-dichloro-4-ethoxyphenyl)methyl]sulfonyl]-4,5-dihydro-5,5-dimethylisoxazole), fentrazamide, flufenacet, indanofan, mefenacet, metazachlor, metolachlor, naproanilide, napropamide, napropamide-M ((2R)—N,N-diethyl-2-(1-naphthalenyloxy)propanamide), pethoxamid, piperophos, pretilachlor, propachlor, propisochlor, pyroxasulfone, and thenylchlor, including resolved forms such as S-metolachlor and chloroacetamides and oxyacetamides. Of note is a compound of the invention mixed with flufenacet.

"Auxin transport inhibitors" (b10) are chemical substances that inhibit auxin transport in plants, such as by binding with an auxin-carrier protein. Examples of auxin transport inhibitors include diflufenzopyr, naptalam (also known as N-(1-naphthyl)phthalamic acid and 2-[(1-naphthalenylamino)carbonyl]benzoic acid).

"PDS inhibitors" (b11) are chemical compounds that inhibit carotenoid biosynthesis pathway at the phytoene desaturase step. Examples of PDS inhibitors include beflubutamid, diflufenican, fluridone, flurochloridone, flurtamone norflurzon and picolinafen.

"HPPD inhibitors" (b12) are chemical substances that inhibit the biosynthesis of synthesis of 4-hydroxyphenyl-pyruvate dioxygenase. Examples of HPPD inhibitors include benzobicyclon, benzofenap, bicyclopyrone (4-hydroxy-3-[[2-[(2-methoxyethoxy)methyl]-6-(trifluoromethyl)-3-pyridinyl]carbonyl]bicyclo[3.2.1]oct-3-en-2-one), fenquinotrione (2-[[8-chloro-3,4-dihydro-4-(4-methoxyphenyl)-3-oxo-2-quinoxalinyl]carbonyl]-1,3-cyclohexanedione), isoxachlortole, isoxaflutole, mesotrione, pyrasulfotole, pyrazolynate, pyrazoxyfen, sulcotrione, tefuryltrione, tembotrione, tolpyralate (1-[[1-ethyl-4-[3-(2-methoxyethoxy)-2-methyl-4-(methylsulfonyl)benzoyl]-1H-pyrazol-5-yl]oxy]ethyl methyl carbonate), topramezone, 5-chloro-3-[(2-hydroxy-6-oxo-1-cyclohexen-1-yl)carbonyl]-1-(4-methoxyphenyl)-2(1H)-quinoxalinone, 4-(2,6-diethyl-4-methylphenyl)-5-hydroxy-2,6-dimethyl-3 (2H)-pyridazinone, 4-(4-fluorophenyl)-6-[(2-hydroxy-6-oxo-1-cyclohexen-1-yl)carbonyl]-2-methyl-1,2,4-triazine-3,5(2H, 4H)-dione, 5-[(2-hydroxy-6-oxo-1-cyclohexen-1-yl)carbonyl]-2-(3-methoxyphenyl)-3-(3-methoxypropyl)-4 (3H)-pyrimidinone, 2-methyl-N-(4-methyl-1,2,5-oxadiazol-3-yl)-3-(methylsulfinyl)-4-(trifluoromethyl)benzamide and 2-methyl-3-(methyl sulfonyl)-N-(1-methyl-1H-tetrazol-5-yl)-4-(trifluoromethyl)benzamide. Of note is a compound of the invention mixed with mesotrione or pyrasulfatole.

"HST inhibitors" (b13) disrupt a plant's ability to convert homogentisate to 2-methyl-6-solanyl-1,4-benzoquinone, thereby disrupting carotenoid biosynthesis. Examples of HST inhibitors include haloxydine, cyclopyrimorate (6-chloro-3-(2-cyclopropyl-6-methylphenoxy)-4-pyridazinyl 4-morpholinecarboxylate), pyriclor, 3-(2-chloro-3,6-difluorophenyl)-4-hydroxy-1-methyl-1,5-naphthyridin-2 (1H)-one, 7-(3,5-dichloro-4-pyridinyl)-5-(2,2-difluoroethyl)-8-hydroxypyrido[2,3-b]pyrazin-6(5H)-one and 4-(2,6-diethyl-4-methylphenyl)-5-hydroxy-2,6-dimethyl-3 (2H)-pyridazinone.

HST inhibitors also include compounds of Formulae A and B.

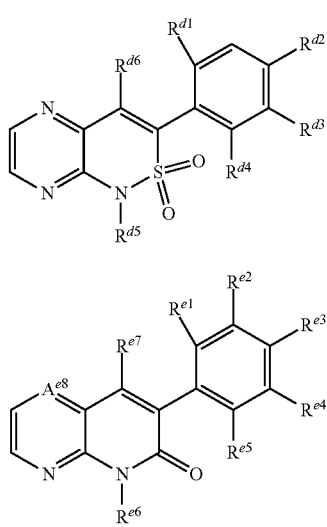

A

B wherein $R^{d1}$ is H, Cl or CF$_3$; $R^{d2}$ is H, Cl or Br; $R^{d3}$ is H or Cl; $R^{d4}$ is H, Cl or CF$_3$; $R^{d5}$ is CH$_3$, CH$_2$CH$_3$ or CH$_2$CHF$_2$; and $R^{d6}$ is OH, or —OC(=O)-i-Pr; and $R^{e1}$ is H, F, Cl, CH$_3$ or CH$_2$CH$_3$; $R^{e2}$ is H or CF$_3$; $R^{e3}$ is H, CH$_3$ or CH$_2$CH$_3$; $R^{e4}$ is H, F or Br; $R^{e5}$ is Cl, CH$_3$, CF$_3$, OCF$_3$ or CH$_2$CH$_3$; $R^{e6}$ is H, CH$_3$, CH$_2$CHF$_2$ or C≡CH; $R^{e7}$ is OH, —OC(=O)Et, —OC(=O)-i-Pr or —OC(=O)-t-Bu; and $A^{e8}$ is N or CH.

"Cellulose biosynthesis inhibitors" (b14) inhibit the biosynthesis of cellulose in certain plants. They are most effective when applied preemergence or early postemergence on young or rapidly growing plants. Examples of cellulose biosynthesis inhibitors include chlorthiamid, dichlobenil, flupoxam, indaziflam (N$^2$-[(1R,2S)-2,3-dihydro-2,6-dimethyl-1H-inden-1-yl]-6-(1-fluoroethyl)-1,3,5-triazine-2,4-diamine), isoxaben and triaziflam.

"Other herbicides" (b15) include herbicides that act through a variety of different modes of action such as mitotic disruptors (e.g., flamprop-M-methyl and flamprop-M-isopropyl), organic arsenicals (e.g., DSMA, and MSMA), 7,8-dihydropteroate synthase inhibitors, chloroplast isoprenoid synthesis inhibitors and cell-wall biosynthesis inhibitors. Other herbicides include those herbicides having unknown modes of action or do not fall into a specific category listed in (b1) through (b14) or act through a combination of modes of action listed above. Examples of other herbicides include aclonifen, asulam, amitrole, bromobutide, cinmethylin, clomazone, cumyluron, daimuron, difenzoquat, etobenzanid, fluometuron, flurenol, fosamine, fosamine-ammonium, dazomet, dymron, ipfencarbazone (1-(2,4-dichlorophenyl)-N-(2,4-difluorophenyl)-1,5-dihydro-N-(1-methylethyl)-5-oxo-4H-1,2,4-triazole-4-carboxamide), metam, methyldymron, oleic acid, oxaziclomefone, pelargonic acid, pyributicarb and 5-[[(2,6-difluorophenyl)methoxy]methyl]-4,5-dihydro-5-methyl-3-(3-methyl-2-thienyl)isoxazole.

"Herbicide safeners" (b16) are substances added to a herbicide formulation to eliminate or reduce phytotoxic effects of the herbicide to certain crops. These compounds protect crops from injury by herbicides but typically do not prevent the herbicide from controlling undesired vegetation. Examples of herbicide safeners include but are not limited to benoxacor, cloquintocet-mexyl, cumyluron, cyometrinil, cyprosulfamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride, oxabetrinil, N-(aminocarbonyl)-2-methylbenzenesulfonamide and N-(aminocarbonyl)-2-fluorobenzenesulfonamide, 1-bromo-4-[(chloromethyl)sulfonyl]benzene, 2-(dichloromethyl)-2-methyl-1,3-dioxolane (MG 191), 4-(dichloroacetyl)-1-oxa-4-azospiro[4.5]decane (MON 4660), 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide.

The compounds of Formula 1 can be prepared by general methods known in the art of synthetic organic chemistry. One or more of the following methods and variations as described in Schemes 1-19 can be used to prepare the compounds of Formula 1. The definitions of $R^1$, $R^2$, $R^3$, $R^4$, $R^5$, $R^6$, $Q^1$, $Q^2$, J, A, $Y^1$, and $Y^2$ in the compounds of Formulae 1-19 below are as defined above in the Summary of the Invention unless otherwise noted. The compounds of Formulae 1a, 1b, 1aa, 1ab, 1ba, 1bb, 1c, 1d, 1e, 1f, 1g, 1g', 1h, 2', 4a, 4b, 5a, 5b, 5c, 5d, 5a', 5b', 7a, 7b, 8a, 8b, 10a and 10b are various subsets of a compound of Formulae 1, 2, 4, 5, 7, 8 and 10 respectively As shown in Scheme 1 a compound of Formula 1a (i.e. Formula 1 wherein $R^1$, $R^4$ and $R^5$ are H, and $Y^1$ and $Y^2$ are 0) can be prepared by reaction of acids of Formula 2 with amines of Formula 3 in the presence of a dehydrative coupling reagent such as propylphosphonic anhydride, dicyclohexylcarbodiimide, N-(3-dimethylaminopropyl)-N-ethylcarbodiimide, N,N-carbonyldiimidazole, 2-chloro-1,3-dimethylimidazolium chloride or 2-chloro-1-methylpyridinium iodide. Polymer-supported reagents, such as polymer-supported cyclohexylcarbodiimide, are also suitable. These reactions are typically run at temperatures ranging from 0 to 60° C. in a solvent such as dichloromethane, acetonitrile, N,N-dimethylformamide or ethyl acetate in the presence of a base such as triethylamine, N,N-diisopropylamine, or 1,8-diazabicyclo[5.4.0]undec-7-ene. See *Organic Process Research & Development* 2009, 13, 900-906 for coupling conditions employing propylphosphonic anhydride. The method of Scheme 1 utilizing propylphosphonic anhydride is illustrated by Step E of Synthesis Example 1. The method of Scheme 1 is illustrated by Step E of Synthesis Example 1 and Step D of Synthesis Example 2.

include, but are not limited to, hydroxides such as sodium and potassium hydroxide and carbonates such as sodium and potassium carbonate. Suitable acids for the reaction include, but are not limited to, inorganic acids such as hydrochloric acid, hydrobromic acid and sulfuric acid, and organic acids such as acetic acid and trifluoroacetic acid. A wide variety of co-solvents are suitable for the reaction including, but not limited to, methanol, ethanol and tetrahydrofuran. The reaction is conducted at temperatures ranging from −20° C. to the boiling point of the solvent, and typically from 0 to 100° C. The method of Scheme 3 is illustrated by Step D of Synthesis Example 1 and Step D of Synthesis Example 2.

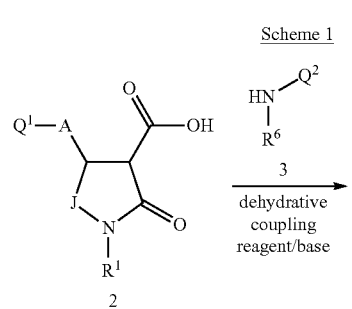

Scheme 1

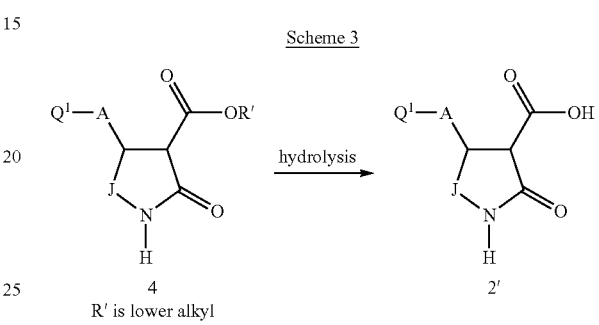

Scheme 3

As shown in Scheme 2, a compound of Formula 2 can be prepared by reaction of a compound of Formula 2' with corresponding electrophiles of Formula 18 in the presence of a base. In Formula 18, G denotes a leaving group, i.e. a nucleofuge. Depending upon selection of $R^1$, suitable electrophiles for the reaction can include alkyl halides such as alkyl chlorides, alkyl bromides and alkyl iodides, alkylsulfonates, acid anhydrides such as tert-butoxycarbonyl anhydride and acetic anhydride, and haloalkylsilanes such as chlorotrimethylsilane. Suitable bases for the reaction include inorganic bases such as alkali or alkaline earth metal (e.g., lithium, sodium, potassium and cesium) hydroxides, alkoxides, carbonates, and phosphates, and organic bases such as triethylamine, N,N-diisopropylethylamine and 1,8-diazabicyclo[5.4.0]undec-7-ene. A wide variety of solvents are suitable for the reaction including, but not limited to, tetrahydrofuran, dichloromethane, N,N-dimethylformamide, N,N-dimethylacetamide, N-methylpyrrolidinone, acetonitrile, $C_2$-$C_6$ alcohols and acetone as well as mixtures of these solvents. This reaction is conducted at temperatures ranging from −20 to 200° C., and typically between 0 and 50° C.

As shown in Scheme 4, a compound of Formulae 4a or 4b can be obtained by reduction of a compound of Formulae 5a or 5b respectively and subsequent in situ cyclization of the resulting intermediate amine. A wide variety of methods for reduction of the aliphatic nitro or nitrile group in compounds of Formula 5a or 5b are known in the literature. These methods include catalytic hydrogenation in the presence of palladium on carbon or Raney nickel, iron or zinc metal in acidic medium (see, for example, *Berichte der Deutschen Chemischen Gesellschaft* 1904, 37, 3520-3525), and lithium aluminum hydride. Reduction of an aliphatic nitro group can also be achieved with samarium(II) iodide in the presence of a proton source such as methanol (see for example, *Tetrahedron Letters* 1991, 32 (14), 1699-1702). Alternatively sodium borohydride in the presence of a nickel catalyst such as nickel(II) acetate or nickel(II) chloride can be used (see for example, *Tetrahedron Letters* 1985, 26 (52), 6413-6416). The method of Scheme 4 utilizing sodium borohydride in the presence of nickel(II) acetate is illustrated by Step C of Synthesis Example 1. The method of Scheme 4 utilizing iron in the presence of ammonium chloride is illustrated by Step C of Synthesis Example 2.

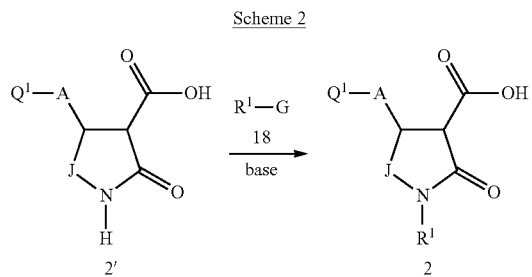

Scheme 2

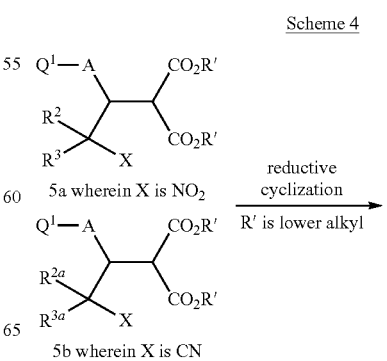

Scheme 4

As shown in Scheme 3, a compound of Formula 2' can be prepared by hydrolysis of esters of Formula 4. Hydrolysis is carried out with aqueous base or aqueous acid, typically in the presence of a co-solvent. Suitable bases for the reaction

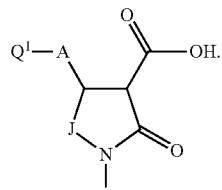

4a wherein J is
—CR²R³—;
and 4b wherein J is
—CR²ᵃR³ᵃ—CR²R³—
and R²ᵃ and R³ᵃ are
both H.

As shown in Scheme 5, a compound of Formula 5a or 5b can be prepared by reacting diesters of Formula 6 with nitroalkanes of Formula 7a or nitriles of Formula 7b respectively, typically in the presence of a base. Suitable bases for the reaction include alkali metal lower alkoxides such as sodium methoxide in methanol or sodium ethoxide in ethanol. Compounds of Formula 6 can readily be prepared by various methods such as by Knoevenagel condensation of aldehydes and malonates (see for example G. Jones, *Organic Reactions* Volume 15, John Wiley and Sons, 1967).

Scheme 5

Compounds of Formula 5c or 5d (i.e. compounds of Formulae 5a or 5b wherein R² and R³ are H) can be prepared by reacting compounds of Formula 8a or 8b with malonates of Formula 9 in the presence of a base as shown in Scheme 6. Suitable bases for this reaction include, but are not limited to, alkali metal lower alkoxides such as sodium methoxide in methanol or sodium ethoxide in ethanol, or bases such as lithium bis(trimethylsilyl)amide, sodium bis(trimethylsilyl)amide and lithium diisopropylamide in solvents such as tetrahydrofuran. Typically, the reaction is carried out in the range of from −78° C. to 23° C. such as those described in *Synthesis* 2005, 2239-2245. Conditions for effecting this transformation in refluxing water in the absence of a catalyst are reported in *Synthetic Communications* 2013, 43, 744-748.

Scheme 6

A compound of Formula 6 can readily be prepard by Knoevenagel condensation of aldehydes of Formula 14 and malonates of Formula 9 as shown in Scheme 7. Also shown in Scheme 7, compounds of Formulae 8a and 8b can be prepared by Knoevenagel condensation of aldehydes of Formula 14 and nitromethane or acetonitrile respectively.

Scheme 7

Compounds of Formulae 5a' and 5a" can be prepared stereoselectively by reacting a nitroalkene of Formula 8a with a malonate of Formula 9 in the presence of a chiral catalyst and optionally in the presence of a suitable base as shown in Scheme 8. Suitable catalysts include, but are not limited to Ni(II) with vicinal diamine ligands such as Ni(II) Bis[(R,R)—N,N'-dibenzylcyclohexane-1,2-diamine]dibromide, Ni(II) Bis[(S,S)—N,N-dibenzylcyclohexane-1,2-diamine]dibromide or nickel(II) bromide with chiral 1,1'-bi (tetrahydroisoquinoline) type diamines. Suitable organic bases for this reaction include, but are not limited to, piperidine, morpholine, triethylamine, 4-methylmorpholine or N,N-diisopropylethylamine. This transformation can be accomplished neat or in solvents such as tetrahydrofuran, toluene or dichloromethane. Typically, the reaction is carried out in the range of from −78° C. to 80° C. using 0 to 1 equivalent of catalyst and optionally 0 to 1 equivalent of a base. Conditions for effecting this transformation have been reported in *J. Am. Chem. Soc.* 2005, 9958-9959 or *Eur. J Org. Chem.* 2011, 5441-5446 for conditions. Nitroalkenes of Formula 8a can readily be prepared from aldehydes and nitromethane by methods known to those skilled in the art.

Scheme 8

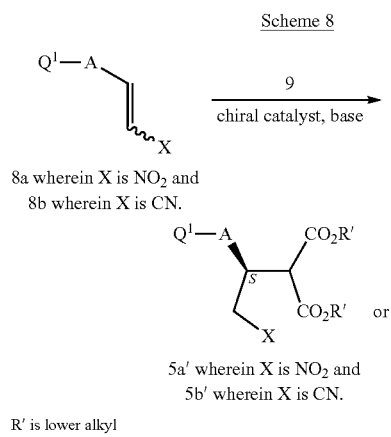

8a wherein X is NO₂ and
8b wherein X is CN.

5a' wherein X is NO₂ and
5b' wherein X is CN.

R' is lower alkyl

As shown in Scheme 9, compounds of Formulae 1aa and 1ab can also be prepared by reductive cyclization of compounds of Formulae 10a and 10b analogous to the method of Scheme 4. As also shown in Scheme 9, compounds of Formula 1ba and 1bb (i.e. Formula 1 wherein $R^1$ is OH, $R^4$ and $R^5$ are H; and $Y^1$ and $Y^2$ are O) can be prepared from compounds of Formulae 10a and 10b respectively by catalytic transfer hydrogenation with ammonium formate in the presence of palladium on carbon, and subsequent in situ cyclization of the intermediate hydroxylamine. See J. Med. Chem. 1993, 36, 1041-1047 for catalytic transfer hydrogenation/cyclization conditions to produce N-hydroxypyrrolidinones.

Scheme 9

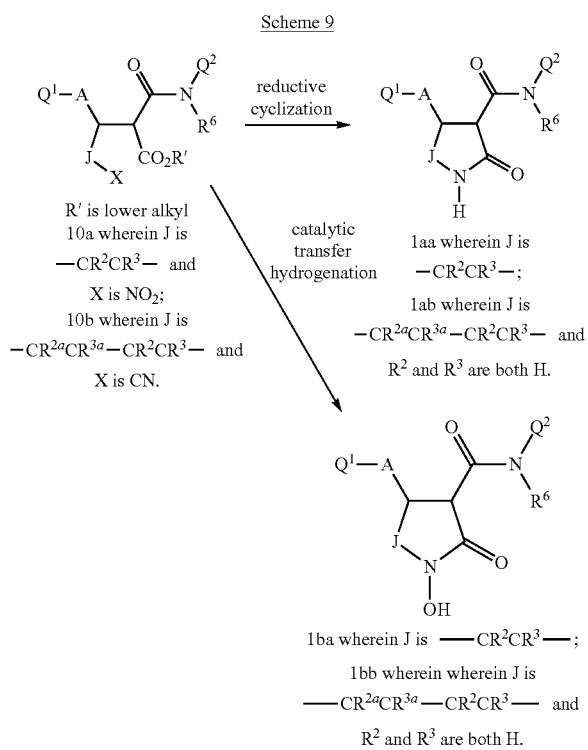

As shown in Scheme 10, compounds of Formulae 10a and 10b can be prepared by reacting a compound of Formula 11 with a compound of Formula 7a or a compound of Formula 7b respectively in a solvent, in the presence of a base analogous to the method described in Scheme 5.

Scheme 10

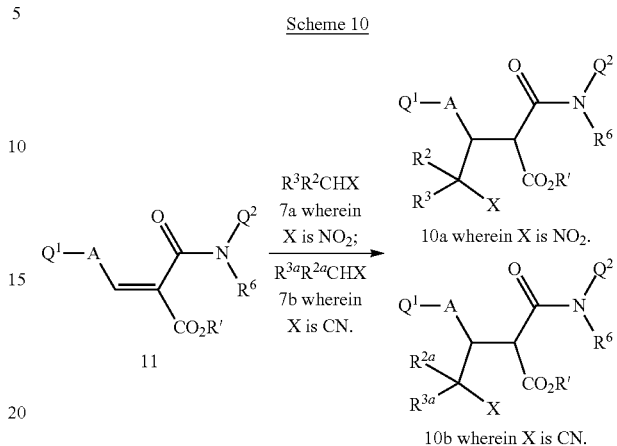

As shown in Scheme 11, a compound of Formula 10aa (i.e. Formula 10a wherein $R^{2a}$ and $R^{3a}$ are H) can be prepared, analogous to the method of Scheme 6, by reacting nitroalkenes of Formula 8 with a malonate of Formula 12.

Scheme 11

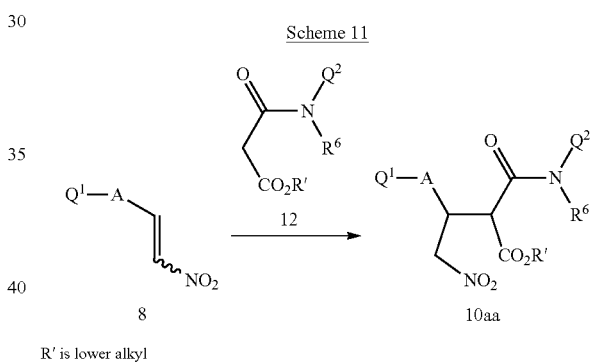

R' is lower alkyl

As shown in Scheme 12, a compound of Formula 11 can be prepared by reaction of a malonic amide of Formula 12 with an aldehyde of Formula 14. Also as shown in Scheme 12, a malonic amide of Formula 12 can readily be prepared from lower alkyl malonyl chlorides of Formula 13 such as methyl malonyl chloride and amines of Formula 3.

Scheme 12

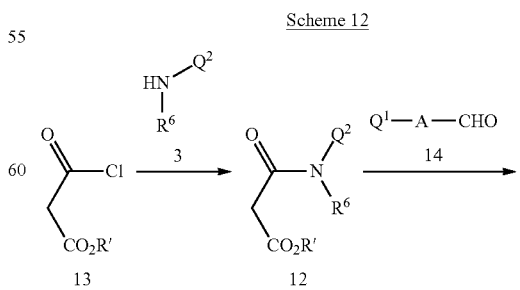

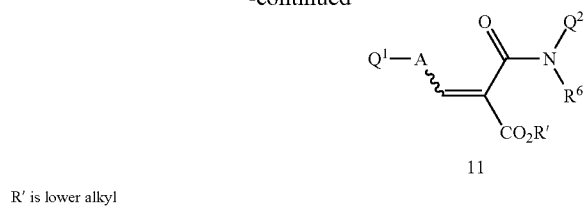

R' is lower alkyl

As shown in Scheme 13, mixtures of a compound of Formulae 1c (i.e. Formula 1 wherein $R^1$ and $R^5$ are H, $R^4$ is halogen and $Y^1$ and $Y^2$ are O) and 1d (i.e. Formula 1 wherein $R^1$ and $R^4$ are H, $R^5$ is halogen and $Y^1$ and $Y^2$ are O) can be prepared by reacting compounds of Formula 1a with a halogen source in a solvent, in the presence or absence of an initiator. Separation of the regioisomers produced in this reaction can be achieved by standard methods such as chromatography or fractional crystallization. Suitable halogen sources for this reaction include bromine, chlorine, N-chlorosuccinimide, N-bromosuccinimide and N-iodosuccinimide. Suitable initiators for this reaction include 2,2'-azobisisobutyronitrile (AIBN) and benzoyl peroxide. Typically, the reaction is carried out in solvents such as dichloromethane in the range of from 0° C. to the boiling point of the solvent.

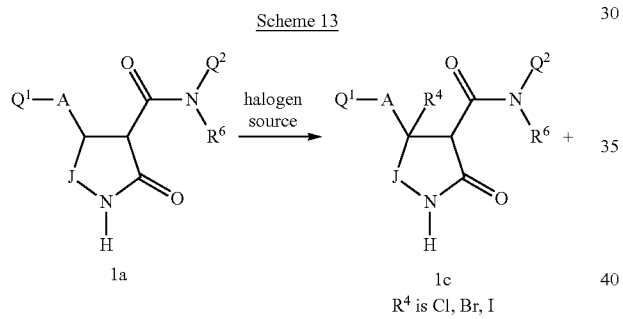

Scheme 13

1a

1c
$R^4$ is Cl, Br, I

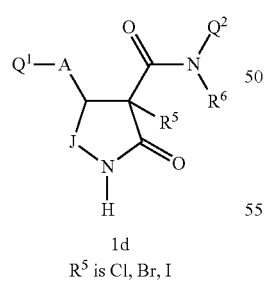

1d
$R^5$ is Cl, Br, I

As shown in Scheme 14, a compound of Formula 1e (i.e. Formula 1 wherein $R^1$ is $NH_2$, $R^4$ and $R^5$ are H and $Y^1$ and $Y^2$ are O) can be prepared by reacting compounds of Formula 1a with an aminating reagent such as O-(diphenylphosphinyl)hydroxylamine and hydroxylamino-O-sulphonic acid. For procedures, conditions and reagents see *Bioorganic & Medicinal Chemistry Letters* 2009, 19, 5924-5926 and *Journal of Organic Chemistry* 2002, 67, 6236-6239.

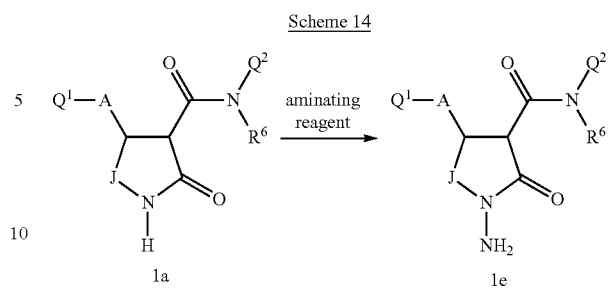

Scheme 14

1a

1e

As shown in Scheme 15, a compound of Formula 1f (i.e. Formula 1 wherein $R^4$, $R^5$ and $R^6$ are H and $Y^1$ is O) can be produced by reaction of a compound of Formula 15 with an isocyanate (i.e. of Formula 16 wherein $Y^2$ is O) or an isothiocyanates (i.e. of Formula 16 wherein $Y^2$ is S) in the presence of base. Examples of the base which can be used for the present process include those listed for the method of Scheme 5. The reaction temperature can be selected from the range of from -78° C. to the boiling point of an inert solvent used. Typically, the reaction is carried out at temperatures ranging from -78° C. to 100° C. in a solvent such as toluene.

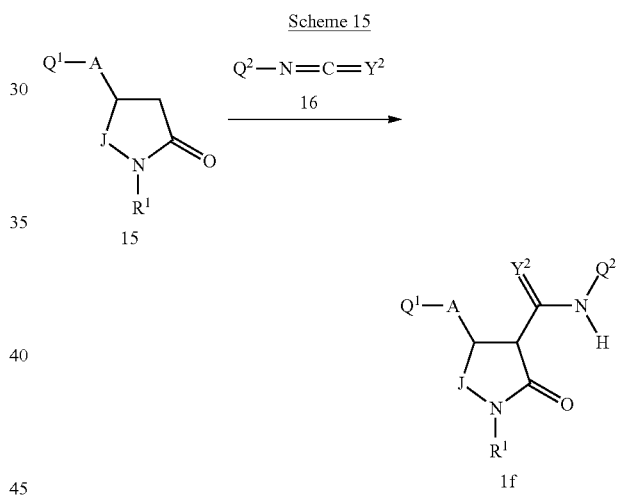

Scheme 15

15

16

1f

As shown in Scheme 16, a compound of Formula 15 can be prepared, analogous to the method described in Scheme 2, by reaction of compounds of Formula 17 with corresponding electrophiles of Formula 18 in the presence of base.

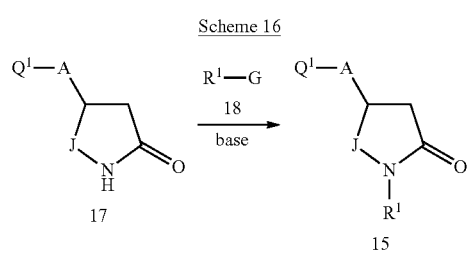

Scheme 16

17

18

15

As shown in Scheme 17, a compound of Formula 17 can be prepared by decarboxylation of an acid of Formula 2. Decarboxylation is carried by heating a compound of Formula 2 in a solvent, typically in the presence of an acid. Suitable acids for the reaction include, but are not limited to, p-toluenesulfonic acid. A wide variety of co-solvents are suitable for the reaction including, but not limited to, toluene, isopropanol acetate and isobutyl methylketone. The reaction is conducted at temperatures ranging from −20° C. and to the boiling point of the solvent, and typically from 0 to 150° C.

Scheme 17

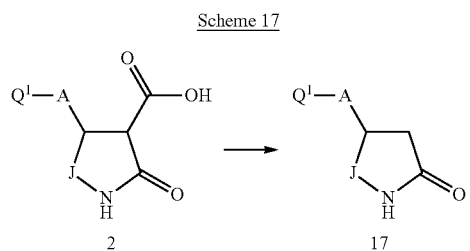

As shown in Scheme 18, a compound of Formula 1g (i.e. Formula 1 wherein $R^1$ is H $R^4$ and $R^5$ are H, and $Y^1$ and $Y^2$ are S) can be prepared by reacting a compound of Formula 1a with at least two equivalents of a thionation reagent such as Lawesson's reagent, tetraphosphorus decasulfide or diphosphorus pentasulfide in a solvent such as tetrahydrofuran or toluene. Typically, the reaction is carried out at temperatures ranging from 0 to 115° C. One skilled in the art recognizes that using less than two equivalents of the thionating reagent can provide mixtures comprising compounds of Formulae 1g and 1g' (products wherein $Y^1$ is O and $Y^2$ is S, or $Y^1$ is S and $Y^2$ is O), which can be separated by conventional methods such as chromatography and crystallization.

Scheme 18

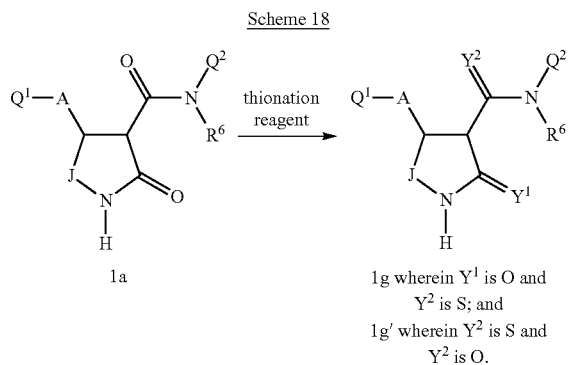

As shown in Scheme 19, a compound of Formula 1h (i.e. Formula 1 wherein $R^1$, $R^4$, $R^5$ are H, $Y^2$ is O and $Y^1$ is NH) can be prepared by alkylation of a compound of Formula 1a with triethyloxonium tetrafluoroborate (Meerwein's reagent) followed by treatment of the resulting imino ether of Formula 19 with aqueous ammonia.

Scheme 19

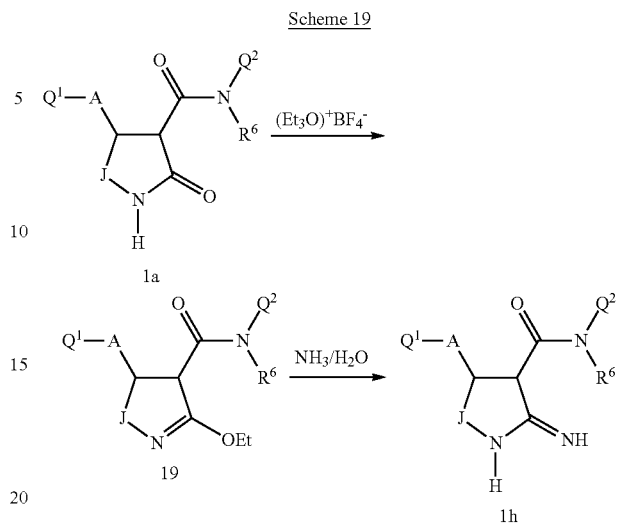

It is recognized by one skilled in the art that various functional groups can be converted into others to provide different compounds of Formula 1. For a valuable resource that illustrates the interconversion of functional groups in a simple and straightforward fashion, see Larock, R. C., *Comprehensive Organic Transformations: A Guide to Functional Group Preparations*, 2nd Ed., Wiley-VCH, New York, 1999. For example, intermediates for the preparation of compounds of Formula 1 may contain aromatic nitro groups, which can be reduced to amino groups, and then be converted via reactions well known in the art such as the Sandmeyer reaction, to various halides, providing compounds of Formula 1. The above reactions can also in many cases be performed in alternate order.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following non-limiting Examples are illustrative of the invention. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet; and "d" means doublet. Mass spectra (MS) are reported as the molecular weight of the highest isotopic abundance parent ion (M+1) formed by addition of H+ (molecular weight of 1) to the molecule, or (M−1) formed by the loss of H+ (molecular weight of 1) from the molecule, observed by using liquid chromatography coupled to a mass spectrometer (LCMS) using either atmospheric pressure chemical ionization (AP+) where "amu" stands for unified atomic mass units.

Synthesis Example 1

Preparation N-(2,3-difluorophenyl)-4-[(4-fluorophenyl)methyl]-2-oxo-3-pyrrolidinecarboxamide (Compound 13)

Step A: Preparation of 1,3-diethyl 2-[2-(4-fluorophenyl)ethylidene]propanedioate Titanium tetrachloride (14.5 mL, 14.5 mmol, 1 M in methylene chloride) was added dropwise to 20 mL of tetrahydrofuran and cooled to −1.5° C. The temperature was maintained under 3.5° C. during dropwise addition. The resulting yellow suspension was slowly combined with a solution of 4-fluorophenyl acetaldehyde (4 g, 29.0 mmol) and diethyl malonate (4.6 g, 29.0 mmol) in 25 mL of dry tetrahydrofuran while maintaining the internal temperature under 3° C. At this point, dry pyridine (9.2 mL, 115.8 mmol) was added to the solution which was then stirred for 1 h maintaining an internal temperature of −3° C. to 0° C. and then allowing the mixture to warm to ambient temperature over 16 h. The reaction mixture was diluted with water and extracted with ether. The combined organic extracts were washed with water, aqueous 0.5 N HCl, water, aqueous saturated NaHCO$_3$ and aqueous saturated NaCl sequentially and finally dried over Na$_2$SO$_4$. The crude material was chromatographed on silica gel (60-120 mesh), eluting with 30% ethyl acetate in petroleum ether to give 4.0 g of a crude product of the title compound which was carried on to Step B without characterization or further purification.

Step B: Preparation of 1,3-diethyl 2-[1-(4-fluorophenyl)methy]-2-nitroethyl]propanedioate To a solution of 1,3-diethyl 2-[2-(4-fluorophenyl)ethylidene]propanedioate (i.e. the product of Step A, 4 g, 14.3 mmol) in ethanol (40 mL) was added nitromethane (8.7 g, 142.7 mmol) followed by sodium ethoxide (0.388 g, 1.4 mmol, 25 wt % in ethanol) and the reaction mixture stirred at room temperature for 16 h. The reaction mixture was diluted with ethyl acetate and washed with water and brine solution. The organic layer was separated and dried over Na$_2$SO$_4$ and concentrated in vacuo. The crude material was chromatographed on silica gel (60-120 mesh), eluting with 30% ethyl acetate in petroleum ether to give 5.0 g of a crude product of the title compound which was carried on to Step C without characterization or further purification.

Step C: Preparation of ethyl 4-[(4-fluorophenyl)methyl]-2-oxo-3-pyrrolidinecarboxylate To a solution of 1,3-diethyl 2-[1-(4-fluorophenyl)methy]-2-nitroethyl]propanedioate (i.e. the product of Step B, 5.0 g, 14.7 mmol) in ethanol (50 mL) was added NiAc$_2$.4H$_2$O (18.2 g, 73.2 mmol). The solution was cooled to 0° C. and NaBH$_4$ (2.7 g, 73.2 mmol) was added portion wise. The solution was allowed to warmed to ambient temperature and stirred for 16 h. The reaction mixture was filtered through Celite® diatomaceous earth filter aid. The filtrate was diluted with ethyl acetate and washed with water and brine solution. The organic layer was separated and then dried over Na$_2$SO$_4$ and concentrated in vacuo. The crude material was chromatographed on silica gel (60-120 mesh), eluting with 60% ethyl acetate in petroleum ether to give the title compound as a solid (0.85 g).
MS: [M+1] 266.0.

Step D: Preparation of 4-[(4-fluorophenyl)methyl]-2-oxo-3-pyrrolidinecarboxylic acid To a solution of ethyl 4-[(4-fluorophenyl)methyl]-2-oxo-3-pyrrolidinecarboxylate (i.e. the product of Step C, 0.8 g, 3.0 mmol) in ethanol (10 mL) at 0° C. was added sodium hydroxide (0.362 g, 50 wt % aq solution). The solution was stirred and allowed to warm to ambient temperature for 16 h. The reaction mass was diluted with ethyl acetate and washed with aqueous 1 N HCl, water and brine solution. The organic layer was separated and then dried over Na$_2$SO$_4$ and concentrated in vacuo. The crude material was purified by tritrating with diethyl ether and pentane to give the title compound as a solid (0.5 g).
MS: [M−1] 236.0.

Step E: Preparation of N-(2,3-difluorophenyl)-4-[(4-fluorophenyl)methyl]-2-oxo-3-pyrrolidinecarboxamide To a solution of 4-[(4-fluorophenyl)methyl]-2-oxo-3-pyrrolidinecarboxylic acid (i.e. the product of Step D, 0.2 g, 0.84 mmol) in methylene chloride (2 mL) was added triethylamine (0.255 g, 2.5 mmol) and 2,3-difluoroanaline (0.120 g, 0.93 mmol) followed by propylphosphonic anhydride (0.456 g, 1.4 mmol). The solution was stirred for 16 h and then diluted with ethyl acetate, and washed with water and brine solution. The organic layer was separated and then dried over Na$_2$SO$_4$ and concentrated in vacuo. The crude material was purified by tritrating with diethyl ether and pentane to give the title compound as an off-white solid (0.18 g).
MS: [M−1] 236.0 and MP 173-176° C.;
$^1$H NMR (DMSO-d$_6$, 300 MHz) δ 10.06 (s, 1H), 7.97 (s, 1H), 7.61-7.64 (m, 1H), 7.01-7.28 (m, 6H), 3.45-3.48 (m, 1H), 3.25-3.27 (m, 1H), 2.95-3.08 (m, 2H), 2.79-2.81 (m, 2H).

Synthesis Example 2

Preparation of N-(2,3-difluorophenyl)-2-oxo-4-[(1E)-2-phenylethenyl]-3-pyrrolidinecarboxamide (Compound 33)

Step A: Preparation of 1,3-diethyl 2-[(2E)-3-phenyl-2-propen-1-ylidene]-propanedioate To a solution of (2E)-3-phenyl-2-propenal (5.0 g, 37.83 mmol), diethyl malonate (6.05 g, 37.83 mmol) and piperidine (0.64 g, 7.57 mmol) in toluene (30 mL) was added acetic acid (0.43 mL). The reaction mixture was refluxed for 3 h under a Dean-Stark trap to remove water by azeotropic distillation. The progress of the reaction was monitored by thin-layer chromatography analysis. After completion, the reaction mixture was poured into water (25 mL) and extracted with ethyl acetate (3×25 mL). The combined organic layers were washed with water (25 mL), dried over $Na_2SO_4$ and concentrated to afford the crude product. The crude product was purified by silica gel column chromatography, eluting with 0% to 100% ethyl acetate in petroleum ether, to afford the title compound (8.0 g) as a pale brown liquid.

$^1$H NMR δ 7.54-7.48 (m, 3H), 7.39-7.34 (m, 3H), 7.29-7.23 (m, 1H), 7.04 (d, J=15.2 Hz, 1H), 4.37 (q, J=6.8 Hz, 2H), 4.28 (q, J=6.8 Hz, 2H), 1.40-1.28 (m, 6H).

Step B: Preparation of 1,3-diethyl 2-[(2E)-1-(nitromethyl)-3-phenyl-2-propen-1-yl]propanedioate To a solution of 1,3-diethyl 2-[(2E)-3-phenyl-2-propen-1-ylidene]-propanedioate (i.e. the product of Step A, 6.0 g, 21.87 mmol) and nitromethane (2.0 g, 32.80 mmol) in ethanol (60 mL) at 0° C. was added sodium methoxide (120 mg, 2.18 mmol). The reaction mixture was stirred at 23° C. overnight. The progress of the reaction was monitored by thin-layer chromatography analysis. After completion, the reaction was concentrated under reduced pressure, and the crude reaction mass was extracted with ethyl acetate (3×40 mL). The organic layer was washed with water (50 mL), dried over $Na_2SO_4$ and concentrated to afford the crude product. The crude product was purified by column chromatography, eluting with 0% to 100% ethyl acetate in petroleum ether, to afford the title compound (3.9 g) as a pale yellow solid.

$^1$H NMR δ 7.33-7.24 (m, 5H), 6.57 (d, J=16.0 Hz, 1H), 6.15-6.08 (m, 1H), 4.77-4.66 (m, 2H), 4.25-4.16 (m, 4H), 3.75-3.72 (m, 1H), 3.66 (d, J=7.2 Hz, 1H), 1.29-1.20 (m, 6H).

Step C: Preparation of ethyl 2-oxo-4-[(1E)-2-phenylethenyl]-3-pyrrolidinecarboxylate A mixture of 1,3-diethyl 2-[(2E)-1-(nitromethyl)-3-phenyl-2-propen-1-yl]propanedioate (i.e. the product of Step B, 3.9 g, 11.62 mmol), iron powder (3.25 g, 58.15 mmol) and ammonium chloride (310 mg, 5.81 mmol) in a mixture of ethanol and water (9:1, 60 mL) was heated to the reflux temperature of the solvent for 24 h. The progress of the reaction was monitored by thin-layer chromatography analysis. After completion, the reaction mixture was filtered, and the filtrate was concentrated under reduced pressure to give crude product. The crude product was purified by silica gel column chromatography, eluting with 0% to 100% ethyl acetate in petroleum ether, to afford the title compound (1.5 g) as a pale yellow liquid.

$^1$H NMR δ 7.36-7.23 (m, 5H), 6.54 (d, J=15.6 Hz, 1H), 6.18-6.12 (m, 1H), 5.94 (brs, 1H), 4.26 (q, J=6.8 Hz, 2H), 3.73-3.63 (m, 2H), 3.32 (d, J=8.8 Hz, 1H), 3.25 (t, J=8.4 Hz, 1H), 1.31 (t, J=6.8 Hz, 3H).

Step D: Preparation of N-(2,3-difluorophenyl)-2-oxo-4-[(1E)-2-phenylethenyl]-3-pyrrolidinecarboxamide To a solution of 2-oxo-4-[(1E)-2-phenylethenyl]-3-pyrrolidinecarboxylate (i.e. the product of Step C, 1.5 g, 5.78 mmol) in a mixture of methanol and tetrahydrofuran (6:4, 20 mL) was added 1 N aqueous sodium hydroxide. The reaction mixture was stirred at 23° C. for 16 h. The progress of the reaction was monitored by thin-layer chromatography analysis. After completion, the reaction mixture was cooled to 0° C., acidified with 1 N hydrochloric acid and extracted with ethyl acetate (3×25 mL). The organic layer was washed with water (20 mL), dried over $Na_2SO_4$ and concentrated to afford the intermediate acid (1.12 g), which was used directly in the amine coupling step without any further purification. To a solution of the intermediate acid (0.6 g, 2.59 mmol), 2,3-difluoroaniline (0.4 g, 3.11 mmol) and triethylamine (1.09 mL, 7.78 mmol) in methylene chloride (20 mL) at 0° C. was added propylphosphonic anhydride (T3P®) (1.24 g, 3.89 mmol). The reaction mixture was stirred at 23° C. overnight. The progress of the reaction was monitored by thin-layer chromatography analysis. After completion, the reaction mixture was poured into water (15 mL) and extracted with dichloromethane (3×15 mL). The organic layer was separated, dried over $Na_2SO_4$ and concentrated under reduced pressure to afford crude product. The crude compound was purified by column chromatography, eluting with 0% to 100% ethyl acetate in petroleum ether, to afford the title compound, a compound of the present invention, as an off-white solid (0.5 g).

$^1$H NMR (DMSO-$d_6$) δ 10.23 (s, 1H), 8.10 (s, 1H), 7.80-7.76 (m, 1H), 7.41 (d, J=7.6 Hz, 2H), 7.32 (t, J=7.6 Hz, 2H), 7.24-7.15 (m, 3H), 6.52 (d, J=16 Hz, 1H), 6.40-6.34 (m, 1H), 3.67 (d, J=9.6 Hz, 1H), 3.60-3.56 (m, 1H), 3.49 (t, J=8.8 Hz, 1H), 3.17 (t, J=8.8 Hz, 1H).

Synthesis Example 3

Preparation of N-(2,3-difluorophenyl)-2-oxo-4-(2-phenylethyl)-3-pyrrolidinecarboxamide (Compound 35)

Step A: Preparation of N-(2,3-difluorophenyl)-2-oxo-4-(2-phenylethyl)pyrrolidine-3-carboxamide A solution of N-(2,3-difluorophenyl)-2-oxo-4-[(1E)-2-phenylethenyl]-3-pyrrolidinecarboxamide (i.e. the product of Example 2, Step D, 0.30 g, 0.87 mmol) in ethanol (20 mL) was placed under nitrogen atmosphere. Palladium on carbon (10%, 0.150 g) was added, and the reaction mixture was stirred under hydrogen balloon pressure at 23° C. for 2 h. The progress of the reaction was monitored by thin-layer chromatography analysis. After completion, the reaction mixture was filtered through Celite® diatomaceous earth filter aid, and the filtrate was concentrated under reduced pressure to afford the crude product. The crude product was purified by silica gel column chromatography, eluting with 0% to 100% ethyl acetate in petroleum ether, to afford the title compound, a compound of the invention, as a colorless solid (0.20 g).

$^1$H NMR (DMSO-$d_6$) δ 10.24 (s, 1H), 7.98 (s, 1H), 7.79-7.76 (m, 1H), 7.29-7.16 (m, 7H), 3.46-3.39 (m, 2H), 2.94 (t, J=8.8 Hz, 1H), 2.77-2.71 (m, 1H), 2.59 (t, J=8.0 Hz, 2H), 1.86-1.74 (m, 2H).

Synthesis Example 4

Preparation of 4-[2-(3-chlorophenyl)ethynyl]N-(2-fluorophenyl)-2-oxo-3-pyrrolidinecarboxamide (Compound 25)

Step A: Preparation of 3-(3-chlorophenyl)-2-propynal
Step B: Preparation of 1,3-diethyl 2-[3-(3-chlorophenyl)-2-propyn-1-ylidene]propanedioate
Step C: Preparation of 1,3-diethyl 2-[3-(3-chlorophenyl)-1-(nitromethyl)-2-propyn-1-yl]propanedioate
Step D Preparation of ethyl 4-[2-(3-chlorophenyl)ethynyl]-2-oxo-3-pyrrolidinecarboxylate
Step E: Preparation of 4-[2-(3-chlorophenyl)ethynyl]-2-oxo-3-pyrrolidinecarboxylic acid
Step F: Preparation of 4-[2-(3-chlorophenyl)ethynyl]-N-(2-fluorophenyl)-2-oxo-3-pyrrolidinecarboxamide By the procedures described herein together with methods known in the art, the following compounds of Tables 1 to 320 can be prepared. The following abbreviations are used in the Tables which follow: i means iso, c means cyclo, Me means methyl, Et means ethyl, Pr means propyl, Bu means butyl, i-Pr means isopropyl, c-Pr cyclopropyl, Ph means phenyl, OMe means methoxy, SMe means methylthio, NHMe means methylamino, CN means cyano, $NO_2$ means nitro, TMS means trimethylsilyl, SOMe means methylsulfinyl, $C_2F_5$ means $CF_2CF_3$ and $SO_2Me$ means methylsulfonyl.

TABLE 1

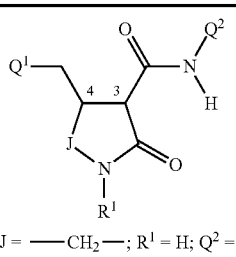

J = —$CH_2$—; $R^1$ = H; $Q^2$ =

Ph(2-F); and $Q^1$ =

| $Q^1$ | $Q^1$ | $Q^1$ |
|---|---|---|
| Ph(3-Cl) | Ph(3-Et) | Ph(3-$OCF_2H$) |
| Ph(3-F) | Ph(3-$CF_3$) | Ph(3-O-i-Pr) |
| Ph(3-Br) | Ph(3-$CH_2CF_3$) | Ph(3-OMe) |
| Ph(3-Me) | Ph(3-$OCF_3$) | Ph(3-$OCF_2CF_2H$) |
| Ph(2-Cl) | 2-Pyridinyl(6-$CF_3$) | 2-Thienyl |
| Ph(2-F) | 2-Pyridinyl(6-Me) | 2-Thienyl(4-$CF_3$) |
| Ph(2-Br) | 2-Pyridinyl(5-F) | 2-Thienyl(5-$CF_3$) |
| Ph(2-Me) | 2-Pyridinyl(5-$CF_3$) | 3-Thienyl |
| Ph(2-$CF_3$) | 2-Pyridinyl(5-Me) | 3-Thienyl(4-$CF_3$) |
| Ph(2-$OCF_3$) | 2-Pyridinyl(4-F) | 3-Thienyl(5-$CF_3$) |
| Ph(2-$OCF_2H$) | 2-Pyridinyl(4-$CF_3$) | 2-Furyl |
| Ph(2-OMe) | 2-Pyridinyl(4-Me) | 2-Furyl(4-$CF_3$) |
| Ph(2-$OCF_2CF_2H$) | 2-Pyridinyl(3-F) | 2-Furyl(5-$CF_3$) |
| Ph(2-$CH_2CF_3$) | 2-Pyridinyl(3-$CF_3$) | 3-Furyl |
| Ph(2-O-i-Pr) | 2-Pyridinyl(3-Me) | 3-Furyl(4-$CF_3$) |
| Ph(4-Cl) | 3-Pyridinyl | 3-Furyl(5-$CF_3$) |
| Ph(4-F) | 3-Pyridinyl(6-F) | 1H-Pyrazol-1-yl |
| Ph(4-Br) | 3-Pyridinyl(6-$CF_3$) | 4-$CF_3$-1H-Pyrazol-1-yl |
| Ph(4-Me) | 3-Pyridinyl(6-Me) | 1H-Imidazol-1-yl |
| Ph(4-Et) | 3-Pyridinyl(5-F) | 4-$CF_3$-1H-Imidazol-1-yl |
| Ph(4-$CF_3$) | 3-Pyridinyl(5-$CF_3$) | 2-$CF_3$-1H-Imidazol-1-yl |
| Ph(4-$OCF_3$) | 3-Pyridinyl(5-Me) | 1-Me-1H-Imidazol-2-yl |
| Ph(4-$OCF_2H$) | 3-Pyridinyl(4-F) | 1-Me-1H-Imidazol-4-yl |
| Ph(4-OMe) | 3-Pyridinyl(4-$CF_3$) | 3-Me-1H-Imidazol-4-yl |
| Ph(4-$CH_2CF_3$) | 3-Pyridinyl(4-Me) | 1-Me-1H-Pyrazol-4-yl |
| Ph(4-O-i-Pr) | 3-Pyridinyl(2-F) | 1-Me-1H-1,2,3-Triazol-4-yl |
| Ph(4-$OCF_2CF_2H$) | 3-Pyridinyl(2-$CF_3$) | 2-Me-1H-1,2,3-Triazol-4-yl |
| Ph(2,3-di-F) | 3-Pyridinyl(2-Me) | |
| Ph(2,4-di-F) | 4-Pyridinyl | |

TABLE 1-continued

J = —$CH_2$—; $R^1$ = H; $Q^2$ =

Ph(2-F); and $Q^1$ =

| $Q^1$ | $Q^1$ | $Q^1$ |
|---|---|---|
| Ph(2,5-di-F) | 4-Pyridinyl(6-F) | 4-Me-1H-1,2,3-Triazol-2-yl |
| Ph(2,6-di-F) | 4-Pyridinyl(6-$CF_3$) | 4-Me-1H-1,2,3-Triazol-1-yl |
| Ph(3,4-di-F) | 4-Pyridinyl(6-Me) | Pyrazin-2-yl |
| Ph(3,5-di-F) | 4-Pyridinyl(5-F) | Pyrazin-2-yl(5-$CF_3$) |
| Ph(3-Me,4-F) | 4-Pyridinyl(5-$CF_3$) | Pyrimidin-2-yl |
| Ph(3-F,4-Me) | 4-Pyridinyl(5-Me) | Pyrimidin-2-yl(5-$CF_3$) |
| Ph(3-$CF_3$,4-F) | 4-Pyridinyl(3-F) | Pyrimidin-5-yl |
| Ph(3-F,4-$CF_3$) | 4-Pyridinyl(3-$CF_3$) | Pyrimidin-5-yl(2-$CF_3$) |
| Ph(2,3,4-tri-F) | 4-Pyridinyl(3-Me) | 1,3,5-Triazin-2-yl |
| Ph(3,4,5-tri-F) | 4-Pyridinyl(2-F) | Thiazol-2-yl |
| 2-Pyridinyl | 4-Pyridinyl(2-$CF_3$) | Thiazol-2-yl(5-$CF_3$) |
| 2-Pyridinyl(6-F) | 4-Pyridinyl(2-Me) | Thiazol-5-yl |
| Oxazol-2-yl(5-$CF_3$) | 1,4-Dioxolan-2-yl | Thiazol-5-yl(2-$CF_3$) |
| Oxazol-5-yl | 1,4-Dithiolan-2-yl | Oxazol-2-yl |
| Oxazol-5-yl(2-$CF_3$) | 1-naphthyl | Ph(3-$SCF_3$) |
| Isothiazol-5-yl | 2-naphthyl | Ph(3-S-c-Pr) |
| Isothiazol-5-yl(3-$CF_3$) | Benzofuran-2-yl | Ph(3-SOMe) |
| Isothiazol-3-yl | Benzothiophen-2-yl | Ph(3-$SOCF_3$) |
| Isothiazol-3-yl(5-$CF_3$) | 1,3-Benzoxazol-2-yl | Ph(3-SO-c-Pr) |
| Isoxazol-5-yl | 1,3-Benzothiazol-2-yl | Ph(3-$SO_2Me$) |
| Isoxazol-5-yl(3-$CF_3$) | | Ph(3-$SO_2CF_3$) |
| Isoxazol-3-yl | 7-Quinolinyl | Ph(3-$SO_2$-c-Pr) |
| Isoxazol-3-yl(5-$CF_3$) | Indazol-1-yl | Ph(3-propargyl) |
| 1H-1,2,3,4-Tetrazol-1-yl | Benzimidazol-1-yl | Ph(3-(2-Butynyl)) |
| 5-Me-1H-1,2,3,4-Tetrazol-1-yl | Indol-1-yl | Ph(2-$CH_2CH_2$-$OCH_2CH_3$) |
| 1-Me-1H-1,2,3,4-Tetrazol-5-yl | Pyrrolo[2,3-c]pyridin-1-yl | |
| | Ph(3-$OCH_2$-c-Pr) | Ph(2-$CF_3$) |
| 1H-1,2,4-Triazol-1-yl | Ph(2-$OCH_2$-c-Pr) | Ph(3-$CF_3$) |
| 1,3,4-Oxadiazol-2-yl | Ph(4-O($CH_2)_4$-c-hex) | Ph(2-C(=O)$CH_3$) |
| 1,3,4-Thiadiazol-2-yl | Ph($CH_2$-c-Pr) | Ph(2-OC(=O)$CH_3$) |
| 1,2,4-Oxadiazol-3-yl | Ph(4-($CH_2)_4$-c-hex) | Ph(3-OC(=O)$CH_3$) |
| 1,2,4-Thiadiazol-3-yl | Ph(3-$OCH_2CF_2$)) | Ph(2-OC(=O)$CF_3$) |
| Tetrahydropyran-2-yl | Ph(2-(3,3-dichloro-allyloxy)) | Ph(3-OC(=O)$CF_3$) |
| | Ph(2-methoxyethoxy) | |
| Tetrahydropyran-3-yl | Ph(3-propoxypropoxy) | |
| Tetrahydrofuran-2-yl | Ph(2-$CH_2CH_2SCH_3$) | |
| Tetrahydrofuran-3-yl | Ph(2-$CH_2CH_2SOCH_3$) | |
| 1,3-Dioxolan-4-yl | Ph(2-$CH_2CH_2SO_2CH_3$) | |
| 2,2-di-F-1,3-Dioxolan-4-yl | Ph(3-SMe) | |
| 1,3-Dithiolan-4-yl | | |

Table 2 is constructed in the same manner except that the Row Heading "J=—$CH_2$—; $R^1$=H; $Q^2$=Ph(2-F); and $Q^1$=" is replaced with the Row Heading listed for Table 2 below (i.e. "J=—$CH_2$—; $R^1$=H; $Q^2$=Ph(2,3-di-F); and $Q^1$="). Therefore the first entry in Table 2 is a compound of Formula 1 wherein J is —$CH_2$—; $R^1$ is H; $Q^2$ is Ph(2,3-di-F); and $Q^1$ is Ph(3-Cl) (i.e. 3-chlorophenyl). Tables 3 through 40 are constructed similarly.

| Table | Row Heading |
|---|---|
| 2 | J = —$CH_2$—; $R^1$ = H; $Q^2$ = Ph(2,3-di-F); and $Q^1$ = |
| 3 | J = —$CH_2$—; $R^1$ = H; $Q^2$ = Ph(2,4-di-F); and $Q^1$ = |
| 4 | J = —$CH_2$—; $R^1$ = H; $Q^2$ = Ph(2,3,4-tri-F); and $Q^1$ = |
| 5 | J = —$CH_2$—; $R^1$ = H; $Q^2$ = Ph(2-$CF_3$); and $Q^1$ = |
| 6 | J = —$CH_2$—; $R^1$ = H; $Q^2$ = Ph(2-Me); and $Q^1$ = |

| Table | Row Heading |
|---|---|
| 7 | J = —CH$_2$—; R$^1$ = H; Q$^2$ = Ph(2-NO$_2$); and Q$^1$ = |
| 8 | J = —CH$_2$—; R$^1$ = H; Q$^2$ = Ph(2-Cl); and Q$^1$ = |
| 9 | J = —CH$_2$—; R$^1$ = H; Q$^2$ = Ph(2-SO$_2$Me); and Q$^1$ = |
| 10 | J = —CH$_2$—; R$^1$ = H; Q$^2$ = Ph(2-F,3-Cl); and Q$^1$ = |
| 11 | J = —CH$_2$CH$_2$—; R$^1$ = H; Q$^2$ = Ph(2-F); and Q$^1$ = |
| 12 | J = —CH$_2$CH$_2$—; R$^1$ = H; Q$^2$ = Ph(2,3-di-F); and Q$^1$ = |
| 13 | J = —CH$_2$CH$_2$—; R$^1$ = H; Q$^2$ = Ph(2,4-di-F); and Q$^1$ = |
| 14 | J = —CH$_2$CH$_2$—; R$^1$ = H; Q$^2$ = Ph(2,3,4-tri-F); and Q$^1$ = |
| 15 | J = —CH$_2$CH$_2$—; R$^1$ = H; Q$^2$ = Ph(2-CF$_3$); and Q$^1$ = |
| 16 | J = —CH$_2$CH$_2$—; R$^1$ = H; Q$^2$ = Ph(2-Me); and Q$^1$ = |
| 17 | J = —CH$_2$CH$_2$—; R$^1$ = H; Q$^2$ = Ph(2-NO$_2$); and Q$^1$ = |
| 18 | J = —CH$_2$CH$_2$—; R$^1$ = H; Q$^2$ = Ph(2-Cl); and Q$^1$ = |
| 19 | J = —CH$_2$CH$_2$—; R$^1$ = H; Q$^2$ = Ph(2-SO$_2$Me); and Q$^1$ = |
| 20 | J = —CH$_2$CH$_2$—; R$^1$ = H; Q$^2$ = Ph(2-F,3-Cl); and Q$^1$ = |
| 21 | J = —CH$_2$—; R$^1$ = Me; Q$^2$ = Ph(2-F); and Q$^1$ = |
| 22 | J = —CH$_2$—; R$^1$ = Me; Q$^2$ = Ph(2,3-di-F); and Q$^1$ = |
| 23 | J = —CH$_2$—; R$^1$ = Me; Q$^2$ = Ph(2,4-di-F); and Q$^1$ = |
| 24 | J = —CH$_2$—; R$^1$ = Me; Q$^2$ = Ph(2,3,4-tri-F); and Q$^1$ = |
| 25 | J = —CH$_2$—; R$^1$ = Me; Q$^2$ = Ph(2-CF$_3$); and Q$^1$ = |
| 26 | J = —CH$_2$—; R$^1$ = Me; Q$^2$ = Ph(2-Me); and Q$^1$ = |
| 27 | J = —CH$_2$—; R$^1$ = Me; Q$^2$ = Ph(2-NO$_2$); and Q$^1$ = |
| 28 | J = —CH$_2$—; R$^1$ = Me; Q$^2$ = Ph(2-Cl); and Q$^1$ = |
| 29 | J = —CH$_2$—; R$^1$ = Me; Q$^2$ = Ph(2-SO$_2$Me); and Q$^1$ = |
| 30 | J = —CH$_2$—; R$^1$ = Me; Q$^2$ = Ph(2-F,3-Cl); and Q$^1$ = |
| 31 | J = —CH$_2$CH$_2$—; R$^1$ = Me; Q$^2$ = Ph(2-F); and Q$^1$ = |
| 32 | J = —CH$_2$CH$_2$—; R$^1$ = Me; Q$^2$ = Ph(2,3-di-F); and Q$^1$ = |
| 33 | J = —CH$_2$CH$_2$—; R$^1$ = Me; Q$^2$ = Ph(2,4-di-F); and Q$^1$ = |
| 34 | J = —CH$_2$CH$_2$—; R$^1$ = Me; Q$^2$ = Ph(2,3,4-tri-F); and Q$^1$ = |
| 35 | J = —CH$_2$CH$_2$—; R$^1$ = Me; Q$^2$ = Ph(2-CF$_3$); and Q$^1$ = |
| 36 | J = —CH$_2$CH$_2$—; R$^1$ = Me; Q$^2$ = Ph(2-Me); and Q$^1$ = |
| 37 | J = —CH$_2$CH$_2$—; R$^1$ = Me; Q$^2$ = Ph(2-NO$_2$); and Q$^1$ = |
| 38 | J = —CH$_2$CH$_2$—; R$^1$ = Me; Q$^2$ = Ph(2-Cl); and Q$^1$ = |
| 39 | J = —CH$_2$CH$_2$—; R$^1$ = Me; Q$^2$ = Ph(2-SO$_2$Me); and Q$^1$ = |
| 40 | J = —CH$_2$CH$_2$—; R$^1$ = Me; Q$^2$ = Ph(2-F,3-Cl); and Q$^1$ = |

Table 41

Table 41 is constructed the same way as Table 1 above, except the structure is replaced with the following:

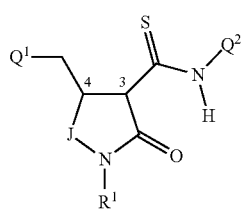

Tables 42 Through 80

This disclosure also includes Tables 42 through 80, each Table is constructed in the same fashion as Tables 2 through 40 above, except that the structure is replaced with the structure in Table 41 above.

Table 81

Table 81 is constructed the same way as Table 1 above, except the structure is replaced with the following:

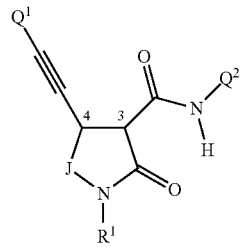

Tables 82 Through 120

This disclosure also includes Tables 82 through 120, each Table is constructed in the same fashion as Tables 2 through 40 above, except that the structure is replaced with the structure in Table 81 above.

Table 121

Table 121 is constructed the same way as Table 1 above, except the structure is replaced with the following:

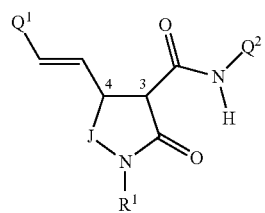

Tables 122 Through 160

This disclosure also includes Tables 122 through 160, each Table is constructed in the same fashion as Tables 2 through 40 above, except that the structure is replaced with the structure in Table 121 above.

Table 161

Table 161 is constructed the same way as Table 1 above, except the structure is replaced with the following:

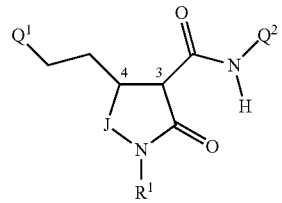

Tables 162 Through 200

This disclosure also includes Tables 162 through 200, each Table is constructed in the same fashion as Tables 2 through 40 above, except that the structure is replaced with the structure in Table 161 above.

Table 201

Table 201 is constructed the same way as Table 1 above, except the structure is replaced with the following:

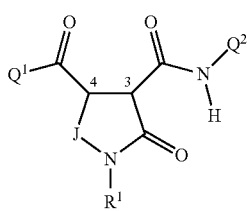

Tables 202 Through 240

This disclosure also includes Tables 202 through 240, each Table is constructed in the same fashion as Tables 2 through 40 above, except that the structure is replaced with the structure in Table 201 above.

Table 241

Table 241 is constructed the same way as Table 1 above, except the structure is replaced with the following:

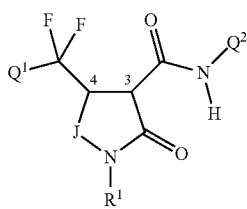

Tables 242 Through 280

This disclosure also includes Tables 242 through 280, each Table is constructed in the same fashion as Tables 2 through 40 above, except that the structure is replaced with the structure in Table 241 above.

Table 281

Table 281 is constructed the same way as Table 1 above, except the structure is replaced with the following:

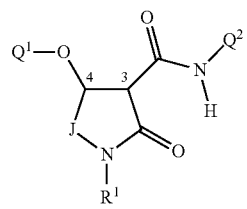

Tables 282 Through 320

This disclosure also includes Tables 282 through 320, each Table is constructed in the same fashion as Tables 2 through 40 above, except that the structure is replaced with the structure in Table 281 above.

Formulation/Utility

A compound of this invention will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil in water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil in water emulsion, flowable concentrate and suspo emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water dispersible ("wettable") or water soluble. Films and coatings formed from film forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

|  | Weight Percent | | |
|---|---|---|---|
|  | Active Ingredient | Diluent | Surfactant |
| Water Dispersible and Water soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone based surfactants; and sugar derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents,* annual American and International Editions published by McCutcheon's Division, The Manufacturing Confectioner Publishing Co.; Sisely and Wood, *Encyclopedia of Surface Active Agents,* Chemical Publ. Co., Inc., New York, 1964; and A. S. Davidson and B. Milwidsky, *Synthetic Detergents,* Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 jam range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", Chemical Engineering, Dec. 4, 1967, pp 147-48, Perry's Chemical Engineer's Handbook, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, U K, 2000.

In the following Examples, all percentages are by weight and all formulations are prepared in conventional ways. Compound numbers refer to compounds in Index Table A. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

High Strength Concentrate

| | |
|---|---|
| Compound 1 | 98.5% |
| silica aerogel | 0.5% |
| synthetic amorphous fine silica | 1.0% |

Example B

Wettable Powder

| | |
|---|---|
| Compound 1 | 65.0% |
| Dodecylphenol-polyethylene glycol ether | 2.0% |
| sodium ligninsulfonate | 4.0% |
| sodium silicoaluminate | 6.0% |
| montmorillonite (calcined) | 23.0% |

Example C

Granule

| | |
|---|---|
| Compound 1 | 10.0% |
| attapulgite granules (low volatile matter, 0.71/0.30 mm; U.S.S. No. 25-50 sieves) | 90.0% |

Example D

Extruded Pellet

| | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

Emulsifiable Concentrate

| | |
|---|---|
| Compound 1 | 10.0% |
| polyoxyethylene sorbitol hexoleate | 20.0% |
| $C_6$-$C_{10}$ fatty acid methyl ester | 70.0% |

Example F

Microemulsion

| | |
|---|---|
| Compound 1 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

Suspension Concentrate

| | |
|---|---|
| Compound 1 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example H

Emulsion in Water

| | |
|---|---|
| Compound 1 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| Water | 58.7% |

Example I

Oil Dispersion

| | |
|---|---|
| Compound 1 | 25% |
| polyoxyethylene sorbitol hexaoleate | 15% |
| organically modified bentonite clay | 2.5% |
| fatty acid methyl ester | 57.5% |

The present disclosure also includes Formulation Examples A through I above except "Compound 1" in each of the above Examples A through I is replaced with "Compound 2", "Compound 3", "Compound 4", "Compound 5", "Compound 7", "Compound 8", "Compound 9", "Compound 10", "Compound 11", "Compound 12", "Compound 13", "Compound 14", "Compound 15", "Compound 16", "Compound 17", "Compound 18", "Compound 19", "Compound 20", "Compound 21", "Compound 22", "Compound 23", "Compound 24", "Compound 25", "Compound 26", "Compound 27" "Compound 28" "Compound 29", "Compound 30", "Compound 31", "Compound 32", "Compound 33" "Compound 34" or "Compound 35".

Test results indicate that the compounds of the present invention are highly active preemergent and/or postemergent herbicides and/or plant growth regulants. The compounds of the invention generally show highest activity for postemergence weed control (i.e. applied after weed seedlings emerge from the soil) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this invention may show tolerance to important agronomic crops including, but is not limited to, alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as *eucalyptus* and conifers (e.g., loblolly pine), and turf species (e.g., Kentucky bluegrass, St. Augustine grass, Kentucky fescue and Bermuda grass). Compounds of this invention can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

As the compounds of the invention have (both preemergent and postemergent herbicidal) activity, to control undesired vegetation by killing or injuring the vegetation or reducing its growth, the compounds can be usefully applied by a variety of methods involving contacting a herbicidally effective amount of a compound of the invention, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation.

A herbicidally effective amount of the compounds of this invention is determined by a number of factors. These factors include: formulation selected, method of application, amount and type of vegetation present, growing conditions, etc. In general, a herbicidally effective amount of compounds of this invention is about 0.001 to 20 kg/ha with a preferred range of about 0.004 to 1 kg/ha. One skilled in the art can easily determine the herbicidally effective amount necessary for the desired level of weed control.

In one common embodiment, a compound of the invention is applied, typically in a formulated composition, to a locus comprising desired vegetation (e.g., crops) and undesired vegetation (i.e. weeds), both of which may be seeds, seedlings and/or larger plants, in contact with a growth medium (e.g., soil). In this locus, a composition comprising a compound of the invention can be directly applied to a plant or a part thereof, particularly of the undesired vegetation, and/or to the growth medium in contact with the plant.

Plant varieties and cultivars of the desired vegetation in the locus treated with a compound of the invention can be obtained by conventional propagation and breeding methods or by genetic engineering methods. Genetically modified plants (transgenic plants) are those in which a heterologous gene (transgene) has been stably integrated into the plant's genome. A transgene that is defined by its particular location in the plant genome is called a transformation or transgenic event.

Genetically modified plant cultivars in the locus which can be treated according to the invention include those that are resistant against one or more biotic stresses (pests such as nematodes, insects, mites, fungi, etc.) or abiotic stresses (drought, cold temperature, soil salinity, etc.), or that contain other desirable characteristics. Plants can be genetically modified to exhibit traits of, for example, herbicide tolerance, insect resistance, modified oil profiles or drought tolerance. Useful genetically modified plants containing single gene transformation events or combinations of transformation events are listed in Exhibit C.

Additional information for the genetic modifications listed in Exhibit C can be obtained from publicly available databases maintained, for example, by the U.S. Department of Agriculture.

The following abbreviations, T1 through T37, are used in Exhibit C for traits. A "-" means the entry is not available; "tol." means "tolerance" and "res." means resistance.

| Trait | Description |
|---|---|
| T1 | Glyphosate tol. |
| T2 | High lauric acid oil |
| T3 | Glufosinate tol. |
| T4 | Phytate breakdown |
| T5 | Oxynil tol. |
| T6 | Disease res. |
| T7 | Insect res. |
| T9 | Modified flower color |
| T11 | ALS Herbicide tol. |
| T12 | Dicamba tol. |
| T13 | Anti-allergy |
| T14 | Salt tol. |
| T15 | Cold tol. |
| T16 | Imidazolinone herb. tol. |
| T17 | Modified alpha-amylase |
| T18 | Pollination control |
| T19 | 2,4-D tol. |
| T20 | Increased lysine |
| T21 | Drought tol. |
| T22 | Delayed ripening/senescence |
| T23 | Modified product quality |
| T24 | High cellulose |
| T25 | Modified starch/carbohydrate |
| T26 | Insect & disease resist. |
| T27 | High tryptophan |
| T28 | Erect leaves semidwarf |
| T29 | Semidwarf |
| T30 | Low iron tol. |
| T31 | Modified oil/fatty acid |
| T32 | HPPD tol. |
| T33 | High oil |
| T34 | Aryloxyalkanoate tol. |
| T35 | Mesotrione tol. |
| T36 | Reduced nicotine |
| T37 | Modified product |

Exhibit C

| Crop | Event Name | Event Code | Trait(s) | Gene(s) |
|---|---|---|---|---|
| Alfalfa | J101 | MON-00101-8 | T1 | cp4 epsps (aroA:CP4) |
| Alfalfa | J163 | MON-ØØ163-7 | T1 | cp4 epsps (aroA:CP4) |
| Canola* | 23-18-17 (Event 18) | CGN-89465-2 | T2 | te |
| Canola* | 23-198 (Event 23) | CGN-89465-2 | T2 | te |
| Canola* | 61061 | DP-Ø61Ø61-7 | T1 | gat4621 |
| Canola* | 73496 | DP-Ø73496-4 | T1 | gat4621 |
| Canola* | GT200 (RT200) | MON-89249-2 | T1 | cp4 epsps (aroA:CP4); goxv247 |
| Canola* | GT73 (RT73) | MON-ØØØ73-7 | T1 | cp4 epsps (aroA:CP4); goxv247 |
| Canola* | HCN10 (Topas 19/2) | — | T3 | bar |
| Canola* | HCN28 (T45) | ACS-BNØØ8-2 | T3 | pat (syn) |
| Canola* | HCN92 (Topas 19/2) | ACS-BNØØ7-1 | T3 | bar |
| Canola* | MON88302 | MON-883Ø2-9 | T1 | cp4 epsps (aroA:CP4) |
| Canola* | MPS961 | — | T4 | phyA |
| Canola* | MPS962 | — | T4 | phyA |
| Canola* | MPS963 | — | T4 | phyA |
| Canola* | MPS964 | — | T4 | phyA |
| Canola* | MPS965 | — | T4 | phyA |
| Canola* | MS1 (B91-4) | ACS-BNØØ4-7 | T3 | bar |
| Canola* | MS8 | ACS-BNØØ5-8 | T3 | bar |
| Canola* | OXY-235 | ACS-BNØ11-5 | T5 | bxn |
| Canola* | PHY14 | — | T3 | bar |
| Canola* | PHY23 | — | T3 | bar |
| Canola* | PHY35 | — | T3 | bar |
| Canola* | PHY36 | — | T3 | bar |
| Canola* | RF1 (B93-101) | ACS-BNØØ1-4 | T3 | bar |
| Canola* | RF2 (B94-2) | ACS-BNØØ2-5 | T3 | bar |
| Canola* | RF3 | ACS-BNØØ3-6 | T3 | bar |
| Bean | EMBRAPA 5.1 | EMB-PV051-1 | T6 | ac1 (sense and antisense) |
| Brinjal # | EE-1 | — | T7 | cry1Ac |
| Cotton | 19-51a | DD-Ø1951A-7 | T11 | S4-HrA |
| Cotton | 281-24-236 | DAS-24236-5 | T3, T7 | pat (syn); cry1F |
| Cotton | 3006-210-23 | DAS-21Ø23-5 | T3, T7 | pat (syn); cry1Ac |
| Cotton | 31707 | — | T5, T7 | bxn; cry1Ac |
| Cotton | 31803 | — | T5, T7 | bxn; cry1Ac |
| Cotton | 31807 | — | T5, T7 | bxn; cry1Ac |
| Cotton | 31808 | — | T5, T7 | bxn; cry1Ac |
| Cotton | 42317 | — | T5, T7 | bxn; cry1Ac |
| Cotton | BNLA-601 | — | T7 | cry1Ac |
| Cotton | BXN10211 | BXN10211-9 | T5 | bxn; cry1Ac |
| Cotton | BXN10215 | BXN10215-4 | T5 | bxn; cry1Ac |
| Cotton | BXN10222 | BXN10222-2 | T5 | bxn; cry1Ac |

Exhibit C

| Crop | Event Name | Event Code | Trait(s) | Gene(s) |
|---|---|---|---|---|
| Cotton | BXN10224 | BXN10224-4 | T5 | bxn; cry1Ac |
| Cotton | COT102 | SYN-IR102-7 | T7 | vip3A(a) |
| Cotton | COT67B | SYN-IR67B-1 | T7 | cry1Ab |
| Cotton | COT202 | — | T7 | vip3A |
| Cotton | Event 1 | — | T7 | cry1Ac |
| Cotton | GMF Cry1A | GTL-GMF311-7 | T7 | cry1Ab-Ac |
| Cotton | GHB119 | BCS-GH005-8 | T7 | cry2Ae |
| Cotton | GHB614 | BCS-GH002-5 | T1 | 2mepsps |
| Cotton | GK12 | — | T7 | cry1Ab-Ac |
| Cotton | LLCotton25 | ACS-GH001-3 | T3 | bar |
| Cotton | MLS 9124 | — | T7 | cry1C |
| Cotton | MON1076 | MON-89924-2 | T7 | cry1Ac |
| Cotton | MON1445 | MON-01445-2 | T1 | cp4 epsps (aroA:CP4) |
| Cotton | MON15985 | MON-15985-7 | T7 | cry1Ac; cry2Ab2 |
| Cotton | MON1698 | MON-89383-1 | T7 | cp4 epsps (aroA:CP4) |
| Cotton | MON531 | MON-00531-6 | T7 | cry1Ac |
| Cotton | MON757 | MON-00757-7 | T7 | cry1Ac |
| Cotton | MON88913 | MON-88913-8 | T1 | cp4 epsps (aroA:CP4) |
| Cotton | Nqwe Chi 6 Bt | — | T7 | — |
| Cotton | SKG321 | — | T7 | cry1A; CpTI |
| Cotton | T303-3 | BCS-GH003-6 | T3, T7 | cry1Ab; bar |
| Cotton | T304-40 | BCS-GH004-7 | T3, T7 | cry1Ab; bar |
| Cotton | CE43-67B | — | T7 | cry1Ab |
| Cotton | CE46-02A | — | T7 | cry1Ab |
| Cotton | CE44-69D | — | T7 | cry1Ab |
| Cotton | 1143-14A | — | T7 | cry1Ab |
| Cotton | 1143-51B | — | T7 | cry1Ab |
| Cotton | T342-142 | — | T7 | cry1Ab |
| Cotton | PV-GHGT07 (1445) | — | T1 | cp4 epsps (aroA:CP4) |
| Cotton | EE-GH3 | — | T1 | mepsps |
| Cotton | EE-GH5 | — | T7 | cry1Ab |
| Cotton | MON88701 | MON-88701-3 | T3, T12 | Modified dmo; bar |
| Cotton | OsCr11 | — | T13 | Modified Cry j |
| Flax | FP967 | CDC-FL001-2 | T11 | als |
| Lentil | RH44 | — | T16 | als |
| Maize | 3272 | SYN-E3272-5 | T17 | amy797E |
| Maize | 5307 | SYN-05307-1 | T7 | ecry3.1Ab |
| Maize | 59122 | DAS-59122-7 | T3, T7 | cry34Ab1; cry35Ab1; pat |
| Maize | 676 | PH-000676-7 | T3, T18 | pat; dam |
| Maize | 678 | PH-000678-9 | T3, T18 | pat; dam |
| Maize | 680 | PH-000680-2 | T3, T18 | pat; dam |
| Maize | 98140 | DP-098140-6 | T1, T11 | gat4621; zm-hra |
| Maize | Bt10 | — | T3, T7 | cry1Ab; pat |
| Maize | Bt176 (176) | SYN-EV176-9 | T3, T7 | cry1Ab; bar |
| Maize | BVLA430101 | — | T4 | phyA2 |
| Maize | CBH-351 | ACS-ZM004-3 | T3, T7 | cry9C; bar |
| Maize | DAS40278-9 | DAS40278-9 | T19 | aad-1 |
| Maize | DBT418 | DKB-89614-9 | T3, T7 | cry1Ac; pinII; bar |
| Maize | DLL25 (B16) | DKB-89790-5 | T3 | bar |
| Maize | GA21 | MON-00021-9 | T1 | mepsps |
| Maize | GG25 | — | T1 | mepsps |
| Maize | GJ11 | — | T1 | mepsps |
| Maize | FI117 | — | T1 | mepsps |
| Maize | GAT-ZM1 | — | T3 | pat |
| Maize | LY038 | REN-00038-3 | T20 | cordapA |
| Maize | MIR162 | SYN-IR162-4 | T7 | vip3Aa20 |
| Maize | MIR604 | SYN-IR604-5 | T7 | mcry3A |
| Maize | MON801 (MON80100) | MON801 | T1, T7 | cry1Ab; cp4 epsps (aroA:CP4); goxv247 |
| Maize | MON802 | MON-80200-7 | T1, T7 | cry1Ab; cp4 epsps (aroA:CP4); goxv247 |
| Maize | MON809 | PH-MON-809-2 | T1, T7 | cry1Ab; cp4 epsps (aroA:CP4); goxv247 |
| Maize | MON810 | MON-00810-6 | T1, T7 | cry1Ab; cp4 epsps (aroA:CP4); goxv247 |
| Maize | MON832 | — | T1 | cp4 epsps (aroA:CP4); goxv247 |
| Maize | MON863 | MON-00863-5 | T7 | cry3Bb1 |
| Maize | MON87427 | MON-87427-7 | T1 | cp4 epsps (aroA:CP4) |
| Maize | MON87460 | MON-87460-4 | T21 | cspB |
| Maize | MON88017 | MON-88017-3 | T1, T7 | cry3Bb1; cp4 epsps (aroA:CP4) |
| Maize | MON89034 | MON-89034-3 | T7 | cry2Ab2; cry1A.105 |
| Maize | MS3 | ACS-ZM001-9 | T3, T18 | bar; barnase |
| Maize | MS6 | ACS-ZM005-4 | T3, T18 | bar; barnase |
| Maize | NK603 | MON-00603-6 | T1 | cp4 epsps (aroA:CP4) |
| Maize | T14 | ACS-ZM002-1 | T3 | pat (syn) |

Exhibit C

| Crop | Event Name | Event Code | Trait(s) | Gene(s) |
|---|---|---|---|---|
| Maize | T25 | ACS-ZM003-2 | T3 | pat (syn) |
| Maize | TC1507 | DAS-01507-1 | T3, T7 | cry1Fa2; pat |
| Maize | TC6275 | DAS-06275-8 | T3, T7 | mocry1F; bar |
| Maize | VIP1034 | — | T3, T7 | vip3A; pat |
| Maize | 43A47 | DP-043A47-3 | T3, T7 | cry1F; cry34Ab1; cry35Ab1; pat |
| Maize | 40416 | DP-040416-8 | T3, T7 | cry1F; cry34Ab1; cry35Ab1; pat |
| Maize | 32316 | DP-032316-8 | T3, T7 | cry1F; cry34Ab1; cry35Ab1; pat |
| Maize | 4114 | DP-004114-3 | T3, T7 | cry1F; cry34Ab1; cry35Ab1; pat |
| Melon | Melon A | — | T22 | sam-k |
| Melon | Melon B | — | T22 | sam-k |
| Papaya | 55-1 | CUH-CP551-8 | T6 | prsv cp |
| Papaya | 63-1 | CUH-CP631-7 | T6 | prsv cp |
| Papaya | Huanong No. 1 | — | T6 | prsv rep |
| Papaya | X17-2 | UFL-X17CP-6 | T6 | prsv cp |
| Plum | C-5 | ARS-PLMC5-6 | T6 | ppv cp |
| Canola** | ZSR500 | — | T1 | cp4 epsps (aroA:CP4); goxv247 |
| Canola** | ZSR502 | — | T1 | cp4 epsps (aroA:CP4); goxv247 |
| Canola** | ZSR503 | — | T1 | cp4 epsps (aroA:CP4); goxv247 |
| Rice | 7Crp#242-95-7 | — | T13 | 7crp |
| Rice | 7Crp#10 | — | T13 | 7crp |
| Rice | GM Shanyou 63 | — | T7 | cry1Ab; cry1Ac |
| Rice | Huahui-1/TT51-1 | — | T7 | cry1Ab; cry1Ac |
| Rice | LLRICE06 | ACS-OS001-4 | T3 | bar |
| Rice | LLRICE601 | BCS-OS003-7 | T3 | bar |
| Rice | LLRICE62 | ACS-OS002-5 | T3 | bar |
| Rice | Tarom molaii + cry1Ab | — | T7 | cry1Ab (truncated) |
| Rice | GAT-OS2 | — | T3 | bar |
| Rice | GAT-OS3 | — | T3 | bar |
| Rice | PE-7 | — | T7 | Cry1Ac |
| Rice | 7Crp#10 | — | T13 | 7crp |
| Rice | KPD627-8 | — | T27 | OASA1D |
| Rice | KPD722-4 | — | T27 | OASA1D |
| Rice | KA317 | — | T27 | OASA1D |
| Rice | HW5 | — | T27 | OASA1D |
| Rice | HW1 | — | T27 | OASA1D |
| Rice | B-4-1-18 | — | T28 | Δ OsBRI1 |
| Rice | G-3-3-22 | — | T29 | OSGA2ox1 |
| Rice | AD77 | — | T6 | DEF |
| Rice | AD51 | — | T6 | DEF |
| Rice | AD48 | — | T6 | DEF |
| Rice | AD41 | — | T6 | DEF |
| Rice | 13pNasNa800725atAprt1 | — | T30 | HvNAS1; HvNAAT-A; APRT |
| Rice | 13pAprt1 | — | T30 | APRT |
| Rice | gHvNAS1-gHvNAAT-1 | — | T30 | HvNAS1; HvNAAT-A; HvNAAT-B |
| Rice | gHvIDS3-1 | — | T30 | HvIDS3 |
| Rice | gHvNAAT1 | — | T30 | HvNAAT-A; HvNAAT-B |
| Rice | gHvNAS1-1 | — | T30 | HvNAS1 |
| Rice | NIA-OS006-4 | — | T6 | WRKY45 |
| Rice | NIA-OS005-3 | — | T6 | WRKY45 |
| Rice | NIA-OS004-2 | — | T6 | WRKY45 |
| Rice | NIA-OS003-1 | — | T6 | WRKY45 |
| Rice | NIA-OS002-9 | — | T6 | WRKY45 |
| Rice | NIA-OS001-8 | — | T6 | WRKY45 |
| Rice | OsCr11 | — | T13 | Modified Cry j |
| Rice | 17053 | — | T1 | cp4 epsps (aroA:CP4) |
| Rice | 17314 | — | T2 | cp4 epsps (aroA:CP4) |
| Rose | WKS82/130-4-1 | IFD-52401-4 | T9 | 5AT; bp40 (f3'5'h) |
| Rose | WKS92/130-9-1 | IFD-52901-9 | T9 | 5AT; bp40 (f3'5'h) |
| Soybean | 260-05 (G94-1, G94-19, G168) | — | T9 | gm-fad2-1 (silencing locus) |
| Soybean | A2704-12 | ACS-GM005-3 | T3 | pat |
| Soybean | A2704-21 | ACS-GM004-2 | T3 | pat |
| Soybean | A5547-127 | ACS-GM006-4 | T3 | pat |
| Soybean | A5547-35 | ACS-GM008-6 | T3 | pat |
| Soybean | CV127 | BPS-CV127-9 | T16 | csr1-2 |
| Soybean | DAS68416-4 | DAS68416-4 | T3 | pat |
| Soybean | DP305423 | DP-305423-1 | T11, T31 | gm-fad2-1 (silencing locus); gm-hra |
| Soybean | DP356043 | DP-356043-5 | T1, T31 | gm-fad2-1 (silencing locus); gat4601 |
| Soybean | FG72 | MST-FG072-3 | T32, T1 | 2mepsps; hppdPF W336 |
| Soybean | GTS 40-3-2 (40-3-2) | MON-04032-6 | T1 | cp4 epsps (aroA:CP4) |
| Soybean | GU262 | ACS-GM003-1 | T3 | pat |
| Soybean | MON87701 | MON-87701-2 | T7 | cry1Ac |
| Soybean | MON87705 | MON-87705-6 | T1, T31 | fatb1-A (sense & antisense); |

Exhibit C

| Crop | Event Name | Event Code | Trait(s) | Gene(s) |
| --- | --- | --- | --- | --- |
| | | | | fad2-1A (sense & antisense); cp4 epsps (aroA:CP4) |
| Soybean | MON87708 | MON-87708-9 | T1, T12 | dmo; cp4 epsps (aroA:CP4) |
| Soybean | MON87769 | MON-87769-7 | T1, T31 | Pj.D6D; Nc.Fad3; cp4 epsps (aroA:CP4) |
| Soybean | MON89788 | MON-89788-1 | T1 | cp4 epsps (aroA:CP4) |
| Soybean | W62 | ACS-GM002-9 | T3 | bar |
| Soybean | W98 | ACS-GM001-8 | T3 | bar |
| Soybean | MON87754 | MON-87754-1 | T33 | dgat2A |
| Soybean | DAS21606 | DAS-21606 | T34, T3 | Modified aad-12; pat |
| Soybean | DAS44406 | DAS-44406-6 | T1, T3, T34 | Modified aad-12; 2mepsps; pat |
| Soybean | SYHT04R | SYN-0004R-8 | T35 | Modified avhppd |
| Soybean | 9582.814.19.1 | — | T3, T7 | cry1Ac, cry1F, PAT |
| Squash | CZW3 | SEM-ØCZW3-2 | T6 | cmv cp, zymv cp, wmv cp |
| Squash | ZW20 | SEM-0ZW20-7 | T6 | zymv cp, wmv cp |
| Sugar Beet | GTSB77 (T9100152) | SY-GTSB77-8 | T1 | cp4 epsps (aroA:CP4); goxv247 |
| Sugar Beet | H7-1 | KM-000H71-4 | T1 | cp4 epsps (aroA:CP4) |
| Sugar Beet | T120-7 | ACS-BV001-3 | T3 | pat |
| Sugar Beet | T227-1 | — | T1 | cp4 epsps (aroA:CP4) |
| Sugarcane | NXI-1T | — | T21 | EcbetA |
| Sunflower | X81359 | — | T16 | als |
| Pepper | PK-SP01 | — | T6 | cmv cp |
| Tobacco | C/F/93/08-02 | — | T5 | bxn |
| Tobacco | Vector 21-41 | — | T36 | NtQPT1 (antisense) |
| Sunflower | X81359 | — | T16 | als |
| Wheat | MON71800 | MON-718ØØ-3 | T1 | cp4 epsps (aroA:CP4) |

*Argentine (*Brassica napus*),
**Polish (*B. rapa*),
Eggplant

Although most typically, compounds of the invention are used to control undesired vegetation, contact of desired vegetation in the treated locus with compounds of the invention may result in super-additive or synergistic effects with genetic traits in the desired vegetation, including traits incorporated through genetic modification. For example, resistance to phytophagous insect pests or plant diseases, tolerance to biotic/abiotic stresses or storage stability may be greater than expected from the genetic traits in the desired vegetation.

Compounds of this invention can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the compounds of the invention with other herbicides can broaden the spectrum of activity against additional weed species, and suppress the proliferation of any resistant biotypes. Thus the present invention also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this invention may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, clodinafop-propargyl, clomazone, clomeprop, clopyralid, clopyralid-olamine, cloransulam-methyl, cumyluron, cyanazine, cycloate, cyclopyrimorate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fenquinotrione, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, hydantocidin, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, napropanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiafenacil, tiocarbazil, tolpyralate, topramezone, tralkoxydim, triallate, triafamone, triasulfuron, triaziflam, tribenuron-methyl, triclopyr, triclopyr-butotyl, triclopyr-triethylammonium, tridiphane, trietazine, trifloxysulfuron, trifludimoxazin, trifluralin, triflusulfuron-methyl, tritosulfuron, vernolate, 3-(2-chloro-3,6-difluorophenyl)-4-hydroxy-1-methyl-1,5-naphthyridin-2(1H)-one, 5-chloro-3-[(2-hydroxy-6-oxo-1-cyclohexen-1-yl)carbonyl]-1-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxypyrido[2,3-b]pyrazin-6(5H)-one), 4-(2,6-diethyl-4-methylphenyl)-5-hydroxy-2,6-dimethyl-3 (2H)-pyridazinone), 5-[[(2,6-difluorophenyl)methoxy] methyl]-4,5-dihydro-5-methyl-3-(3-methyl-2-thienyl)isoxazole (previously methioxolin), 4-(4-fluorophenyl)-6-[(2-hydroxy-6-oxo-1-cyclohexen-1-yl)carbonyl]-2-methyl-1,2,4-triazine-3,5(2H,4H)-dione, methyl 4-amino-3-chloro-6-(4-chloro-2-fluoro-3-methoxyphenyl)-5-fluoro-2-pyridinecarboxylate, 2-methyl-3-(methyl sulfonyl)-N-(1-methyl-1H-tetrazol-5-yl)-4-(trifluoromethyl)benzamide and 2-methyl-N-(4-methyl-1,2,5-oxadiazol-3-yl)-3-(methyl sulfinyl)-4-(trifluoromethyl)benzamide. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Compounds of this invention can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual, 13th Edition*, C. D. S. Tomlin, Ed., British Crop Protection Council, Farnham, Surrey, U. K., 2003 and *The BioPesticide Manual, 2nd Edition*, L. G. Copping, Ed., British Crop Protection Council, Farnham, Surrey, U. K., 2001.

For embodiments where one or more of these various mixing partners are used, the mixing partners are typically used in the amounts similar to amounts customary when the mixture partners are used alone. More particularly in mixtures, active ingredients are often applied at an application rate between one-half and the full application rate specified on product labels for use of active ingredient alone. These amounts are listed in references such as *The Pesticide Manual* and *The BioPesticide Manual*. The weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this invention with other biologically active (particularly herbicidal) compounds or agents (i.e. active ingredients) can result in a greater-than-additive (i.e. synergistic) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When synergism of herbicidal active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of the invention with at least one other herbicidal active ingredient. Of particular note is such a combination where the other herbicidal active ingredient has different site of action from the compound of the invention. In certain instances, a combination with at least one other herbicidal active ingredient having a similar spectrum of control but a different site of action will be particularly advantageous for resistance management. Thus, a composition of the present invention can further comprise (in a herbicidally effective amount) at least one additional herbicidal active ingredient having a similar spectrum of control but a different site of action.

Compounds of this invention can also be used in combination with herbicide safeners such as allidochlor, benoxacor, cloquintocet-mexyl, cumyluron, cyometrinil, cyprosulfonamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone naphthalic anhydride (1,8-naphthalic anhydride), oxabetrinil, N-(aminocarbonyl)-2-methylbenzenesulfonamide, N-(aminocarbonyl)-2-fluorobenzenesulfonamide, 1-bromo-4-[(chloromethyl) sulfonyl]benzene (BCS), 4-(dichloroacetyl)-1-oxa-4-azospiro[4.5]decane (MON 4660), 2-(dichloromethyl)-2-methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, and 3-oxo-1-cyclohexen-1-yl 1-(3,4-dimethylphenyl)-1,6-dihydro-6-oxo-2-phenyl-5-pyrimidinecarboxylate, 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide to increase safety to certain crops. Antidotally effective amounts of the herbicide safeners can be applied at the same time as the compounds of this invention, or applied as seed treatments. Therefore an aspect of the present invention relates to a herbicidal mixture comprising a compound of this invention and an antidotally effective amount of a herbicide safener. Seed treatment is particularly useful for selective weed control, because it physically restricts antidoting to the crop plants. Therefore a particularly useful embodiment of the present invention is a method for selectively controlling the growth of undesired vegetation in a crop comprising contacting the locus of the crop with a herbicidally effective amount of a compound of this invention wherein seed from which the crop is grown is treated with an antidotally effective amount of safener. Antidotally effective amounts of safeners can be easily determined by one skilled in the art through simple experimentation.

Compounds of the invention cans also be mixed with: (1) polynucleotides including but not limited to DNA, RNA, and/or chemically modified nucleotides influencing the amount of a particular target through down regulation, interference, suppression or silencing of the genetically derived transcript that render a herbicidal effect; or (2) polynucleotides including but not limited to DNA, RNA, and/or chemically modified nucleotides influencing the amount of a particular target through down regulation, interference, suppression or silencing of the genetically derived transcript that render a safening effect.

Of note is a composition comprising a compound of the invention (in a herbicidally effective amount), at least one additional active ingredient selected from the group consisting of other herbicides and herbicide safeners (in an effective amount), and at least one component selected from the group consisting of surfactants, solid diluents and liquid diluents.

Preferred for better control of undesired vegetation (e.g., lower use rate such as from synergism, broader spectrum of weeds controlled, or enhanced crop safety) or for preventing the development of resistant weeds are mixtures of a compound of this invention with another herbicide. Table A1 lists particular combinations of Component (a) (i.e. a specific compound of the present invention) with another herbicide as Component (b) illustrative of the mixtures, compositions and methods of the present invention. Compound 17 in the Component (a) column is identified in Index Table A. The second column of Table A1 lists the specific Component (b) compound (e.g., "2,4-D" in the first line). The third, fourth and fifth columns of Table A1 lists ranges of weight ratios for rates at which the Component (a) compound is typically applied to a field grown crop relative to Component (b) (i.e. (a):(b)). Thus, for example, the first line of Table A1 specifically discloses the combination of Component (a) (i.e. Compound 17 in Index Table A) with 2,4 D is typically applied in a weight ratio between 1:192-6:1. The remaining lines of Table A1 are to be construed similarly.

TABLE A1

| Component (a) (Compound #) | Component (b) | Typical Weight Ratio | More Typical Weight Ratio | Most Typical Weight Ratio |
|---|---|---|---|---|
| 1 | 2,4-D | 1:192-6:1 | 1:64-2:1 | 1:24-1:3 |
| 1 | Acetochlor | 1:768-2:1 | 1:256-1:2 | 1:96-1:11 |
| 1 | Acifluorfen | 1:96-12:1 | 1:32-4:1 | 1:12-1:2 |
| 1 | Aclonifen | 1:857-2:1 | 1:285-1:3 | 1:107-1:12 |
| 1 | Alachlor | 1:768-2:1 | 1:256-1:2 | 1:96-1:11 |
| 1 | Ametryn | 1:384-3:1 | 1:128-1:1 | 1:48-1:6 |
| 1 | Amicarbazone | 1:192-6:1 | 1:64-2:1 | 1:24-1:3 |
| 1 | Amidosulfuron | 1:6-168:1 | 1:2-56:1 | 1:1-11:1 |
| 1 | Aminocyclopyrachlor | 1:48-24:1 | 1:16-8:1 | 1:6-2:1 |
| 1 | Aminopyralid | 1:20-56:1 | 1:6-19:1 | 1:2-4:1 |
| 1 | Amitrole | 1:768-2:1 | 1:256-1:2 | 1:96-1:11 |
| 1 | Anilofos | 1:96-12:1 | 1:32-4:1 | 1:12-1:2 |
| 1 | Asulam | 1:960-2:1 | 1:320-1:3 | 1:120-1:14 |
| 1 | Atrazine | 1:192-6:1 | 1:64-2:1 | 1:24-1:3 |
| 1 | Azimsulfuron | 1:6-168:1 | 1:2-56:1 | 1:1-11:1 |
| 1 | Beflubutamid | 1:342-4:1 | 1:114-2:1 | 1:42-1:5 |
| 1 | Benfuresate | 1:617-2:1 | 1:205-1:2 | 1:77-1:9 |

TABLE A1-continued

| Component (a) (Compound #) | Component (b) | Typical Weight Ratio | More Typical Weight Ratio | Most Typical Weight Ratio |
|---|---|---|---|---|
| 1 | Bensulfuron-methyl | 1:25-45:1 | 1:8-15:1 | 1:3-3:1 |
| 1 | Bentazone | 1:192-6:1 | 1:64-2:1 | 1:24-1:3 |
| 1 | Benzobicyclon | 1:85-14:1 | 1:28-5:1 | 1:10-1:2 |
| 1 | Benzofenap | 1:257-5:1 | 1:85-2:1 | 1:32-1:4 |
| 1 | Bicyclopyrone | 1:42-27:1 | 1:14-9:1 | 1:5-2:1 |
| 1 | Bifenox | 1:257-5:1 | 1:85-2:1 | 1:32-1:4 |
| 1 | Bispyribac-sodium | 1:10-112:1 | 1:3-38:1 | 1:1-7:1 |
| 1 | Bromacil | 1:384-3:1 | 1:128-1:1 | 1:48-1:6 |
| 1 | Bromobutide | 1:384-3:1 | 1:128-1:1 | 1:48-1:6 |
| 1 | Bromoxynil | 1:96-12:1 | 1:32-4:1 | 1:12-1:2 |
| 1 | Butachlor | 1:768-2:1 | 1:256-1:2 | 1:96-1:11 |
| 1 | Butafenacil | 1:42-27:1 | 1:14-9:1 | 1:5-2:1 |
| 1 | Butylate | 1:1542-1:2 | 1:514-1:5 | 1:192-1:22 |
| 1 | Carfenstrole | 1:192-6:1 | 1:64-2:1 | 1:24-1:3 |
| 1 | Carfentrazone-ethyl | 1:128-9:1 | 1:42-3:1 | 1:16-1:2 |
| 1 | Chlorimuron-ethyl | 1:8-135:1 | 1:2-45:1 | 1:1-9:1 |
| 1 | Chlorotoluron | 1:768-2:1 | 1:256-1:2 | 1:96-1:11 |
| 1 | Chlorsulfuron | 1:6-168:1 | 1:2-56:1 | 1:1-11:1 |
| 1 | Cincosulfuron | 1:17-68:1 | 1:5-23:1 | 1:2-5:1 |
| 1 | Cinidon-ethyl | 1:384-3:1 | 1:128-1:1 | 1:48-1:6 |
| 1 | Cinmethylin | 1:34-34:1 | 1:11-12:1 | 1:4-3:1 |
| 1 | Clacyfos | 1:34-34:1 | 1:11-12:1 | 1:4-3:1 |
| 1 | Clethodim | 1:48-24:1 | 1:16-8:1 | 1:6-2:1 |
| 1 | Clodinafop-propargyl | 1:20-56:1 | 1:6-19:1 | 1:2-4:1 |
| 1 | Clomazone | 1:384-3:1 | 1:128-1:1 | 1:48-1:6 |
| 1 | Clomeprop | 1:171-7:1 | 1:57-3:1 | 1:21-1:3 |
| 1 | Clopyralid | 1:192-6:1 | 1:64-2:1 | 1:24-1:3 |
| 1 | Cloransulam-methyl | 1:12-96:1 | 1:4-32:1 | 1:1-6:1 |
| 1 | Cumyluron | 1:384-3:1 | 1:128-1:1 | 1:48-1:6 |
| 1 | Cyanazine | 1:384-3:1 | 1:128-1:1 | 1:48-1:6 |
| 1 | Cyclopyrimorate | 1:17-68:1 | 1:5-23:1 | 1:2-5:1 |
| 1 | Cyclosulfamuron | 1:17-68:1 | 1:5-23:1 | 1:2-5:1 |
| 1 | Cycloxydim | 1:96-12:1 | 1:32-4:1 | 1:12-1:2 |
| 1 | Cyhalofop | 1:25-45:1 | 1:8-15:1 | 1:3-3:1 |
| 1 | Daimuron | 1:192-6:1 | 1:64-2:1 | 1:24-1:3 |
| 1 | Desmedipham | 1:322-4:1 | 1:107-2:1 | 1:40-1:5 |
| 1 | Dicamba | 1:192-6:1 | 1:64-2:1 | 1:24-1:3 |
| 1 | Dichlobenil | 1:1371-1:2 | 1:457-1:4 | 1:171-1:20 |
| 1 | Dichlorprop | 1:925-2:1 | 1:308-1:3 | 1:115-1:13 |
| 1 | Diclofop-methyl | 1:384-3:1 | 1:128-1:1 | 1:48-1:6 |
| 1 | Diclosulam | 1:10-112:1 | 1:3-38:1 | 1:1-7:1 |
| 1 | Difenzoquat | 1:288-4:1 | 1:96-2:1 | 1:36-1:4 |
| 1 | Diflufenican | 1:857-2:1 | 1:285-1:3 | 1:107-1:12 |
| 1 | Diflufenzopyr | 1:12-96:1 | 1:4-32:1 | 1:1-6:1 |
| 1 | Dimethachlor | 1:768-2:1 | 1:256-1:2 | 1:96-1:11 |
| 1 | Dimethametryn | 1:192-6:1 | 1:64-2:1 | 1:24-1:3 |
| 1 | Dimethenamid-P | 1:384-3:1 | 1:128-1:1 | 1:48-1:6 |
| 1 | Dithiopyr | 1:192-6:1 | 1:64-2:1 | 1:24-1:3 |
| 1 | Diuron | 1:384-3:1 | 1:128-1:1 | 1:48-1:6 |
| 1 | EPTC | 1:768-2:1 | 1:256-1:2 | 1:96-1:11 |
| 1 | Esprocarb | 1:1371-1:2 | 1:457-1:4 | 1:171-1:20 |
| 1 | Ethalfluralin | 1:384-3:1 | 1:128-1:1 | 1:48-1:6 |
| 1 | Ethametsulfuron-methyl | 1:17-68:1 | 1:5-23:1 | 1:2-5:1 |
| 1 | Ethoxyfen | 1:8-135:1 | 1:2-45:1 | 1:1-9:1 |
| 1 | Ethoxysulfuron | 1:20-56:1 | 1:6-19:1 | 1:2-4:1 |
| 1 | Etobenzanid | 1:257-5:1 | 1:85-2:1 | 1:32-1:4 |
| 1 | Fenoxaprop-ethyl | 1:120-10:1 | 1:40-4:1 | 1:15-1:2 |
| 1 | Fenoxasulfone | 1:85-14:1 | 1:28-5:1 | 1:10-1:2 |
| 1 | Fenquinotrione | 1:17-68:1 | 1:5-23:1 | 1:2-5:1 |
| 1 | Fentrazamide | 1:17-68:1 | 1:5-23:1 | 1:2-5:1 |
| 1 | Flazasulfuron | 1:17-68:1 | 1:5-23:1 | 1:2-5:1 |
| 1 | Florasulam | 1:2-420:1 | 1:1-140:1 | 2:1-27:1 |
| 1 | Fluazifop-butyl | 1:192-6:1 | 1:64-2:1 | 1:24-1:3 |
| 1 | Flucarbazone | 1:8-135:1 | 1:2-45:1 | 1:1-9:1 |
| 1 | Flucetosulfuron | 1:8-135:1 | 1:2-45:1 | 1:1-9:1 |
| 1 | Flufenacet | 1:257-5:1 | 1:85-2:1 | 1:32-1:4 |
| 1 | Flumetsulam | 1:24-48:1 | 1:8-16:1 | 1:3-3:1 |
| 1 | Flumiclorac-pentyl | 1:10-112:1 | 1:3-38:1 | 1:1-7:1 |
| 1 | Flumioxazin | 1:25-45:1 | 1:8-15:1 | 1:3-3:1 |
| 1 | Fluometuron | 1:384-3:1 | 1:128-1:1 | 1:48-1:6 |
| 1 | Flupyrsulfuron-methyl | 1:3-336:1 | 1:1-112:1 | 2:1-21:1 |
| 1 | Fluridone | 1:384-3:1 | 1:128-1:1 | 1:48-1:6 |
| 1 | Fluroxypyr | 1:96-12:1 | 1:32-4:1 | 1:12-1:2 |
| 1 | Flurtamone | 1:857-2:1 | 1:285-1:3 | 1:107-1:12 |
| 1 | Fluthiacet-methyl | 1:48-42:1 | 1:16-14:1 | 1:3-3:1 |
| 1 | Fomesafen | 1:96-12:1 | 1:32-4:1 | 1:12-1:2 |
| 1 | Foramsulfuron | 1:13-84:1 | 1:4-28:1 | 1:1-6:1 |

TABLE A1-continued

| Component (a) (Compound #) | Component (b) | Typical Weight Ratio | More Typical Weight Ratio | Most Typical Weight Ratio |
|---|---|---|---|---|
| 1 | Glufosinate | 1:288-4:1 | 1:96-2:1 | 1:36-1:4 |
| 1 | Glyphosate | 1:288-4:1 | 1:96-2:1 | 1:36-1:4 |
| 1 | Halosulfuron-methyl | 1:17-68:1 | 1:5-23:1 | 1:2-5:1 |
| 1 | Halauxifen | 1:20-56:1 | 1:6-19:1 | 1:2-4:1 |
| 1 | Halauxifen-methyl | 1:20-56:1 | 1:6-19:1 | 1:2-4:1 |
| 1 | Haloxyfop-methyl | 1:34-34:1 | 1:11-12:1 | 1:4-3:1 |
| 1 | Hexazinone | 1:192-6:1 | 1:64-2:1 | 1:24-1:3 |
| 1 | Hydantocidin | 1:1100-16:1 | 1:385-8:1 | 1:144-4:1 |
| 1 | Imazamox | 1:13-84:1 | 1:4-28:1 | 1:1-6:1 |
| 1 | Imazapic | 1:20-56:1 | 1:6-19:1 | 1:2-4:1 |
| 1 | Imazapyr | 1:85-14:1 | 1:28-5:1 | 1:10-1:2 |
| 1 | Imazaquin | 1:34-34:1 | 1:11-12:1 | 1:4-3:1 |
| 1 | Imazethabenz-methyl | 1:171-7:1 | 1:57-3:1 | 1:21-1:3 |
| 1 | Imazethapyr | 1:24-48:1 | 1:8-16:1 | 1:3-3:1 |
| 1 | Imazosulfuron | 1:27-42:1 | 1:9-14:1 | 1:3-3:1 |
| 1 | Indanofan | 1:342-4:1 | 1:114-2:1 | 1:42-1:5 |
| 1 | Indaziflam | 1:25-45:1 | 1:8-15:1 | 1:3-3:1 |
| 1 | Iodosulfuron-methyl | 1:3-336:1 | 1:1-112:1 | 2:1-21:1 |
| 1 | Ioxynil | 1:192-6:1 | 1:64-2:1 | 1:24-1:3 |
| 1 | Ipfencarbazone | 1:85-14:1 | 1:28-5:1 | 1:10-1:2 |
| 1 | Isoproturon | 1:384-3:1 | 1:128-1:1 | 1:48-1:6 |
| 1 | Isoxaben | 1:288-4:1 | 1:96-2:1 | 1:36-1:4 |
| 1 | Isoxaflutole | 1:60-20:1 | 1:20-7:1 | 1:7-2:1 |
| 1 | Lactofen | 1:42-27:1 | 1:14-9:1 | 1:5-2:1 |
| 1 | Lenacil | 1:384-3:1 | 1:128-1:1 | 1:48-1:6 |
| 1 | Linuron | 1:384-3:1 | 1:128-1:1 | 1:48-1:6 |
| 1 | MCPA | 1:192-6:1 | 1:64-2:1 | 1:24-1:3 |
| 1 | MCPB | 1:288-4:1 | 1:96-2:1 | 1:36-1:4 |
| 1 | Mecoprop | 1:768-2:1 | 1:256-1:2 | 1:96-1:11 |
| 1 | Mefenacet | 1:384-3:1 | 1:128-1:1 | 1:48-1:6 |
| 1 | Mefluidide | 1:192-6:1 | 1:64-2:1 | 1:24-1:3 |
| 1 | Mesosulfuron-methyl | 1:5-224:1 | 1:1-75:1 | 1:1-14:1 |
| 1 | Mesotrione | 1:42-27:1 | 1:14-9:1 | 1:5-2:1 |
| 1 | Metamifop | 1:42-27:1 | 1:14-9:1 | 1:5-2:1 |
| 1 | Metazachlor | 1:384-3:1 | 1:128-1:1 | 1:48-1:6 |
| 1 | Metazosulfuron | 1:25-45:1 | 1:8-15:1 | 1:3-3:1 |
| 1 | Methabenzthiazuron | 1:768-2:1 | 1:256-1:2 | 1:96-1:11 |
| 1 | Metolachlor | 1:768-2:1 | 1:256-1:2 | 1:96-1:11 |
| 1 | Metosulam | 1:8-135:1 | 1:2-45:1 | 1:1-9:1 |
| 1 | Metribuzin | 1:192-6:1 | 1:64-2:1 | 1:24-1:3 |
| 1 | Metsulfuron-methyl | 1:2-560:1 | 1:1-187:1 | 3:1-35:1 |
| 1 | Molinate | 1:1028-2:1 | 1:342-1:3 | 1:128-1:15 |
| 1 | Napropamide | 1:384-3:1 | 1:128-1:1 | 1:48-1:6 |
| 1 | Napropamide-M | 1:192-6:1 | 1:64-2:1 | 1:24-1:3 |
| 1 | Naptalam | 1:192-6:1 | 1:64-2:1 | 1:24-1:3 |
| 1 | Nicosulfuron | 1:12-96:1 | 1:4-32:1 | 1:1-6:1 |
| 1 | Norflurazon | 1:1152-1:1 | 1:384-1:3 | 1:144-1:16 |
| 1 | Orbencarb | 1:1371-1:2 | 1:457-1:4 | 1:171-1:20 |
| 1 | Orthosulfamuron | 1:20-56:1 | 1:6-19:1 | 1:2-4:1 |
| 1 | Oryzalin | 1:514-3:1 | 1:171-1:2 | 1:64-1:8 |
| 1 | Oxadiargyl | 1:384-3:1 | 1:128-1:1 | 1:48-1:6 |
| 1 | Oxadiazon | 1:548-3:1 | 1:182-1:2 | 1:68-1:8 |
| 1 | Oxasulfuron | 1:27-42:1 | 1:9-14:1 | 1:3-3:1 |
| 1 | Oxaziclomefone | 1:42-27:1 | 1:14-9:1 | 1:5-2:1 |
| 1 | Oxyfluorfen | 1:384-3:1 | 1:128-1:1 | 1:48-1:6 |
| 1 | Paraquat | 1:192-6:1 | 1:64-2:1 | 1:24-1:3 |
| 1 | Pendimethalin | 1:384-3:1 | 1:128-1:1 | 1:48-1:6 |
| 1 | Penoxsulam | 1:10-112:1 | 1:3-38:1 | 1:1-7:1 |
| 1 | Penthoxamid | 1:384-3:1 | 1:128-1:1 | 1:48-1:6 |
| 1 | Pentoxazone | 1:102-12:1 | 1:34-4:1 | 1:12-1:2 |
| 1 | Phenmedipham | 1:102-12:1 | 1:34-4:1 | 1:12-1:2 |
| 1 | Picloram | 1:96-12:1 | 1:32-4:1 | 1:12-1:2 |
| 1 | Picolinafen | 1:34-34:1 | 1:11-12:1 | 1:4-3:1 |
| 1 | Pinoxaden | 1:25-45:1 | 1:8-15:1 | 1:3-3:1 |
| 1 | Pretilachlor | 1:192-6:1 | 1:64-2:1 | 1:24-1:3 |
| 1 | Primisulfuron-methyl | 1:8-135:1 | 1:2-45:1 | 1:1-9:1 |
| 1 | Prodiamine | 1:384-3:1 | 1:128-1:1 | 1:48-1:6 |
| 1 | Profoxydim | 1:42-27:1 | 1:14-9:1 | 1:5-2:1 |
| 1 | Prometryn | 1:384-3:1 | 1:128-1:1 | 1:48-1:6 |
| 1 | Propachlor | 1:1152-1:1 | 1:384-1:3 | 1:144-1:16 |
| 1 | Propanil | 1:384-3:1 | 1:128-1:1 | 1:48-1:6 |
| 1 | Propaquizafop | 1:48-24:1 | 1:16-8:1 | 1:6-2:1 |
| 1 | Propoxycarbazone | 1:17-68:1 | 1:5-23:1 | 1:2-5:1 |
| 1 | Propyrisulfuron | 1:17-68:1 | 1:5-23:1 | 1:2-5:1 |
| 1 | Propyzamide | 1:384-3:1 | 1:128-1:1 | 1:48-1:6 |
| 1 | Prosulfocarb | 1:1200-1:2 | 1:400-1:4 | 1:150-1:17 |
| 1 | Prosulfuron | 1:6-168:1 | 1:2-56:1 | 1:1-11:1 |

TABLE A1-continued

| Component (a) (Compound #) | Component (b) | Typical Weight Ratio | More Typical Weight Ratio | Most Typical Weight Ratio |
|---|---|---|---|---|
| 1 | Pyraclonil | 1:42-27:1 | 1:14-9:1 | 1:5-2:1 |
| 1 | Pyraflufen-ethyl | 1:5-224:1 | 1:1-75:1 | 1:1-14:1 |
| 1 | Pyrasulfotole | 1:13-84:1 | 1:4-28:1 | 1:1-6:1 |
| 1 | Pyrazolynate | 1:857-2:1 | 1:285-1:3 | 1:107-1:12 |
| 1 | Pyrazosulfuron-ethyl | 1:10-112:1 | 1:3-38:1 | 1:1-7:1 |
| 1 | Pyrazoxyfen | 1:5-224:1 | 1:1-75:1 | 1:1-14:1 |
| 1 | Pyribenzoxim | 1:10-112:1 | 1:3-38:1 | 1:1-7:1 |
| 1 | Pyributicarb | 1:384-3:1 | 1:128-1:1 | 1:48-1:6 |
| 1 | Pyridate | 1:288-4:1 | 1:96-2:1 | 1:36-1:4 |
| 1 | Pyriftalid | 1:10-112:1 | 1:3-38:1 | 1:1-7:1 |
| 1 | Pyriminobac-methyl | 1:20-56:1 | 1:6-19:1 | 1:2-4:1 |
| 1 | Pyrimisulfan | 1:17-68:1 | 1:5-23:1 | 1:2-5:1 |
| 1 | Pyrithiobac | 1:24-48:1 | 1:8-16:1 | 1:3-3:1 |
| 1 | Pyroxasulfone | 1:85-14:1 | 1:28-5:1 | 1:10-1:2 |
| 1 | Pyroxsulam | 1:5-224:1 | 1:1-75:1 | 1:1-14:1 |
| 1 | Quinclorac | 1:192-6:1 | 1:64-2:1 | 1:24-1:3 |
| 1 | Quizalofop-ethyl | 1:42-27:1 | 1:14-9:1 | 1:5-2:1 |
| 1 | Rimsulfuron | 1:13-84:1 | 1:4-28:1 | 1:1-6:1 |
| 1 | Saflufenacil | 1:25-45:1 | 1:8-15:1 | 1:3-3:1 |
| 1 | Sethoxydim | 1:96-12:1 | 1:32-4:1 | 1:12-1:2 |
| 1 | Simazine | 1:384-3:1 | 1:128-1:1 | 1:48-1:6 |
| 1 | Sulcotrione | 1:120-10:1 | 1:40-4:1 | 1:15-1:2 |
| 1 | Sulfentrazone | 1:147-8:1 | 1:49-3:1 | 1:18-1:3 |
| 1 | Sulfometuron-methyl | 1:34-34:1 | 1:11-12:1 | 1:4-3:1 |
| 1 | Sulfosulfuron | 1:8-135:1 | 1:2-45:1 | 1:1-9:1 |
| 1 | Tebuthiuron | 1:384-3:1 | 1:128-1:1 | 1:48-1:6 |
| 1 | Tefuryltrione | 1:42-27:1 | 1:14-9:1 | 1:5-2:1 |
| 1 | Tembotrione | 1:31-37:1 | 1:10-13:1 | 1:3-3:1 |
| 1 | Tepraloxydim | 1:25-45:1 | 1:8-15:1 | 1:3-3:1 |
| 1 | Terbacil | 1:288-4:1 | 1:96-2:1 | 1:36-1:4 |
| 1 | Terbuthylazine | 1:857-2:1 | 1:285-1:3 | 1:107-1:12 |
| 1 | Terbutryn | 1:192-6:1 | 1:64-2:1 | 1:24-1:3 |
| 1 | Thenylchlor | 1:85-14:1 | 1:28-5:1 | 1:10-1:2 |
| 1 | Thiazopyr | 1:384-3:1 | 1:128-1:1 | 1:48-1:6 |
| 1 | Thiencarbazone | 1:3-336:1 | 1:1-112:1 | 2:1-21:1 |
| 1 | Thifensulfuron-methyl | 1:5-224:1 | 1:1-75:1 | 1:1-14:1 |
| 1 | Tiafenacil | 1:17-68:1 | 1:5-23:1 | 1:2-5:1 |
| 1 | Thiobencarb | 1:768-2:1 | 1:256-1:2 | 1:96-1:11 |
| 1 | Tolpyralate | 1:31-37:1 | 1:10-13:1 | 1:3-3:1 |
| 1 | Topramzone | 1:6-168:1 | 1:2-56:1 | 1:1-11:1 |
| 1 | Tralkoxydim | 1:68-17:1 | 1:22-6:1 | 1:8-2:1 |
| 1 | Triafamone | 1:2-420:1 | 1:1-140:1 | 2:1-27:1 |
| 1 | Triallate | 1:768-2:1 | 1:256-1:2 | 1:96-1:11 |
| 1 | Triasulfuron | 1:5-224:1 | 1:1-75:1 | 1:1-14:1 |
| 1 | Triaziflam | 1:171-7:1 | 1:57-3:1 | 1:21-1:3 |
| 1 | Tribenuron-methyl | 1:3-336:1 | 1:1-112:1 | 2:1-21:1 |
| 1 | Triclopyr | 1:192-6:1 | 1:64-2:1 | 1:24-1:3 |
| 1 | Trifloxysulfuron | 1:2-420:1 | 1:1-140:1 | 2:1-27:1 |
| 1 | Trifludimoxazin | 1:25-45:1 | 1:8-15:1 | 1:3-3:1 |
| 1 | Trifluralin | 1:288-4:1 | 1:96-2:1 | 1:36-1:4 |
| 1 | Triflusulfuron-methyl | 1:17-68:1 | 1:5-23:1 | 1:2-5:1 |
| 1 | Tritosulfuron | 1:13-84:1 | 1:4-28:1 | 1:1-6:1 |

Table A2 is constructed the same as Table A1 above except that entries below the "Component (a)" column heading are replaced with the respective Component (a) Column Entry shown below. Compound 2 in the Component (a) column is identified in Index Table A. Thus, for example, in Table A2 the entries below the "Component (a) Column Entries" heading all recite "Compound 2" (i.e. Compound 2 as identified in Index Table A), and the first line below the column headings in Table A2 specifically discloses a mixture of Compound 2 with 2,4-D. Tables A3 through A35 are constructed similarly.

| Table Number | Component (a) Column Entries |
|---|---|
| A2 | Compound 2 |
| A3 | Compound 3 |
| A4 | Compound 4 |
| A5 | Compound 5 |
| A6 | Compound 6 |
| A7 | Compound 7 |
| A8 | Compound 8 |
| A9 | Compound 9 |
| A10 | Compound 10 |
| A11 | Compound 11 |
| A12 | Compound 12 |
| A13 | Compound 13 |
| A14 | Compound 14 |
| A15 | Compound 15 |
| A16 | Compound 16 |
| A17 | Compound 17 |
| A18 | Compound 18 |
| A19 | Compound 19 |
| A20 | Compound 20 |
| A21 | Compound 21 |
| A22 | Compound 22 |

-continued

| Table Number | Component (a) Column Entries |
|---|---|
| A23 | Compound 23 |
| A24 | Compound 24 |
| A25 | Compound 25 |
| A26 | Compound 26 |
| A27 | Compound 27 |
| A28 | Compound 28 |
| A29 | Compound 29 |
| A30 | Compound 30 |
| A31 | Compound 31 |
| A32 | Compound 32 |
| A33 | Compound 33 |
| A34 | Compound 34 |
| A35 | Compound 35 |

Preferred for better control of undesired vegetation (e.g., lower use rate such as from synergism, broader spectrum of weeds controlled, or enhanced crop safety) or for preventing the development of resistant weeds are mixtures of a compound of this invention with a herbicide selected from the group consisting of chlorimuron-ethyl, nicosulfuron, mesotrione, thifensulfuron-methyl, flupyrsulfuron-methyl, tribenuron, pyroxasulfone, pinoxaden, tembotrione, pyroxsulam, metolachlor and S-metolachlor.

The following Tests demonstrate the control efficacy of the compounds of this invention against specific weeds. The weed control afforded by the compounds is not limited, however, to these species. See Index Table A for compound descriptions. The following abbreviations are used in the Index Tables which follow: Ph is phenyl. The abbreviation "Cmpd. No." stands for "Compound Number". The abbreviation "Ex." stands for "Example" and is followed by a number indicating in which example the compound is prepared. Mass spectra are reported with an estimated precision within +0.5 Da as the molecular weight of the highest isotopic abundance parent ion (M+1) formed by addition of H+(molecular weight of 1) to the molecule observed by using atmospheric pressure chemical ionization (AP+). As depicted below for variable A, the bond projecting to the left is connected to the $Q^1$ moiety, and the bond projecting to the right is connected to the remainder of Formula 1.

INDEX TABLE A

| Cmpd. No. | $Q^1$ | $Q^2$ | A | m.p. (° C.) | M − 1 | M + 1 |
|---|---|---|---|---|---|---|
| 1 | Ph(3-Cl) | Ph(2,3-di-F) | —CH$_2$— | 132-134 | | |
| 2 | Ph(3-Cl) | Ph(2-F) | —CH$_2$— | 122-125 | | |
| 3 | Ph | Ph(2-F) | —CH$_2$— | 132-135 | | |
| 4 | Ph | Ph(2,3-di-F) | —CH$_2$— | 182-185 | | |
| 5 | Ph(2-CF$_3$) | Ph(2-CF$_3$) | —CH$_2$— | | 429 | 431 |
| 6 | Ph(4-CF$_3$) | Ph(2-CF$_3$) | —CH$_2$— | 136-139 | | |
| 7 | Ph(4-CF$_3$) | Ph(2,3-di-F) | —CH$_2$— | 198-201 | | |
| 8 | Ph(2,3-di-F) | Ph(2,3-di-F) | —CH$_2$— | 149-153 | | |
| 9 | Ph(2-CF$_3$) | Ph(2,3-di-F) | —CH$_2$— | 173-177 | | |
| 10 | Ph(2,3-di-F) | Ph(2-CF$_3$) | —CH$_2$— | 131-135 | | |
| 11 | Ph(3-CF$_3$) | Ph(2,3-di-F) | —CH$_2$— | 179-182 | | |
| 12 | Ph(3,4-di-F) | Ph(2,3-di-F) | —CH$_2$— | 162-168 | | |
| 13 (Ex. 1) | Ph(4-F) | Ph(2,3-di-F) | —CH$_2$— | 173-176 | | |
| 14 | Ph(4-F) | Ph(2-F) | —CH$_2$— | 135-138 | | |
| 15 | Ph(4-F) | Ph(2-F) | —NHC(=O)(CH$_2$)$_2$— | | 386 | 388 |
| 16 | Ph(4-F) | Ph(2,3-di-F) | —C≡C— | 185-188 | | |
| 17 | Ph(4-F) | Ph(2,3,4-tri-F) | —C≡C— | 186-189 | | |
| 18 | Ph(3-CF$_3$) | Ph(2,3-di-F) | —NHC(=O)— | | 426 | 428 |
| 19 | Ph(4-F) | Ph(2-F) | —C≡C— | 184-187 | | |
| 20 | Ph | Ph(2-F) | —(CH$_2$)$_2$— | 141-144 | | |
| 21 | Ph(3-CH$_3$) | Ph(2-F) | —C≡C— | 123-127 | | |
| 22 | Ph(3-CH$_3$) | Ph(2,3-di-F) | —C≡C— | 155-157 | | |
| 23 | Ph(3-CH$_3$) | Ph(2,3,4-tri-F) | —C≡C— | 172-176 | | |
| 24 | Ph(3-F) | Ph(2-F) | —HC=CH— * | 168-172 | | |
| 25 (Ex. 4) | Ph(3-Cl) | Ph(2,3-di-F) | —C≡C— | 154-156 | | |
| 26 | Ph(3-Cl) | Ph(2,3,4-tri-F) | —C≡C— | 178-182 | | |
| 27 | Ph(4-F) | Ph(2-F) | —HC=CH— * | 160-163 | | |
| 28 | Ph(2-F) | Ph(2,3-di-F) | —HC=CH— * | 204-206 | | |
| 29 | Ph(3-Cl) | Ph(2-F) | —C≡C— | 120-124 | | |
| 30 | Ph(3-F) | Ph(2,3-di-F) | —HC=CH— * | 181-185 | | |
| 31 | Ph(4-F) | Ph(2,3-di-F) | —HC=CH— * | 194-197 | | |
| 32 | Ph | Ph(2-F) | —HC=CH— * | 160-164 | | |
| 33 (Ex. 2) | Ph | Ph(2,3-di-F) | —HC=CH— * | 200-204 | | |
| 34 | Ph(2-F) | Ph(2-F) | —HC=CH— * | 161-164 | | |
| 35 (Ex. 3) | Ph | Ph(2,3-di-F) | —(CH$_2$)$_2$— | 142-145 | | |

* Prepared as the E isomer

Biological Examples of the Invention

Test A

Seeds of plant species selected from barnyardgrass (*Echinochloa crus-galli*), crabgrass (large crabgrass, *Digitaria sanguinalis*), kochia (*Kochia scoparia*), ragweed (common ragweed, *Ambrosia elatior*), morningglory (*Ipomoea* spp.), velvetleaf (*Abutilon theophrasti*), ryegrass, It. (Italian ryegrass, *Lolium multiflorum*), foxtail, giant (giant foxtail, *Setaria faberii*), wheat (*Triticum aestivum*), corn (*Zea mays*), and pigweed (*Amaranthus retroflexus*), were planted into a blend of loam soil and sand and treated preemergence with a directed soil spray using test chemicals formulated in a non-phytotoxic solvent mixture which included a surfactant.

At the same time, plants selected from these crop and weed species and also blackgrass (*Alopecurus myosuroides*), and galium (catchweed bedstraw, *Galium aparine*), were planted in pots containing the same blend of loam soil and sand and treated with postemergence applications of test chemicals formulated in the same manner. Plants ranged in height from 2 to 10 cm and were in the one- to two-leaf stage for the postemergence treatment. Treated plants and untreated controls were maintained in a greenhouse for approximately 10 d, after which time all treated plants were compared to untreated controls and visually evaluated for injury. Plant response ratings, summarized in Table A, are based on a 0 to 100 scale where 0 is no effect and 100 is complete control. A dash (-) response means no test result.

TABLE A

| 1000 g ai/ha | Compounds | | | | | |
|---|---|---|---|---|---|---|
| Postemergence | 1 | 2 | 3 | 4 | 13 | 14 |
| Barnyardgrass | 80 | 30 | 0 | 0 | 80 | 0 |
| Corn | 0 | 0 | 0 | 0 | 0 | 0 |
| Crabgrass | 80 | 80 | 0 | 20 | 80 | 20 |
| Foxtail, Giant | 80 | 60 | 0 | 0 | 60 | 0 |
| Morningglory | 0 | 0 | 0 | 0 | 0 | 0 |
| Pigweed | 0 | 0 | 0 | 0 | 0 | 0 |
| Velvetleaf | 10 | 0 | 0 | 0 | 0 | 0 |
| Wheat | 0 | 0 | 0 | 0 | 0 | 0 |

| 500 g ai/ha | Compounds | | | | | | | | | | | | |
|---|---|---|---|---|---|---|---|---|---|---|---|---|---|
| Postemergence | 5 | 6 | 7 | 8 | 9 | 10 | 11 | 12 | 15 | 16 | 17 | 18 | 19 | 20 |
| Barnyardgrass | 0 | 0 | 60 | 0 | 60 | 0 | 0 | 0 | 0 | 60 | 90 | 30 | 40 | 0 |
| Blackgrass | 0 | 0 | 0 | 0 | 0 | 0 | 0 | 0 | 0 | 0 | 0 | 30 | 0 | 0 |
| Corn | 0 | 0 | 0 | 0 | 0 | 0 | 0 | 0 | 0 | 0 | 0 | 0 | 0 | 0 |
| Foxtail, Giant | 0 | 0 | 20 | 0 | 0 | 0 | 0 | 0 | 0 | 40 | 50 | 50 | 20 | 0 |
| *Galium* | 0 | 0 | 0 | 0 | 0 | 0 | 0 | 0 | 0 | 0 | 0 | 50 | 0 | 0 |
| Kochia | 0 | 0 | 0 | 0 | 30 | 0 | 0 | 0 | 0 | 0 | 0 | 0 | 0 | 0 |
| Pigweed | 0 | 0 | 0 | 0 | 0 | 0 | 0 | 0 | 0 | 0 | 0 | 30 | 0 | 0 |
| Ragweed | 0 | 0 | 0 | 0 | 0 | 0 | 0 | 0 | 0 | 0 | 0 | 0 | 0 | 0 |
| Ryegrass, It. | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 |

| 500 g ai/ha | Compounds | | | | | | | | | | | | | | |
|---|---|---|---|---|---|---|---|---|---|---|---|---|---|---|---|
| Postemergence | 21 | 22 | 23 | 24 | 25 | 26 | 27 | 28 | 29 | 30 | 31 | 32 | 33 | 34 | 35 |
| Barnyardgrass | 50 | 70 | 50 | 70 | 70 | 60 | 60 | 70 | 60 | 80 | 70 | 90 | 90 | 60 | 30 |
| Blackgrass | 0 | 0 | 0 | 0 | 0 | 0 | 0 | 0 | 0 | 0 | 0 | 0 | 0 | 0 | 0 |
| Corn | 0 | 20 | 0 | 0 | 0 | 0 | 0 | 0 | 0 | 20 | 20 | 20 | 0 | 0 | 0 |
| Foxtail, Giant | 20 | 50 | 50 | 80 | 80 | 40 | 70 | 50 | 60 | 80 | 60 | 80 | 70 | 80 | 30 |
| *Galium* | 0 | 20 | 20 | 0 | 60 | 0 | 0 | 20 | 0 | 20 | 30 | 0 | 0 | 0 | 0 |
| Kochia | 0 | 0 | 20 | — | 0 | 0 | — | 0 | 0 | 0 | 30 | 0 | 0 | 0 | 0 |
| Pigweed | 0 | 0 | 0 | 0 | 20 | 0 | 20 | 0 | 0 | 0 | 0 | 0 | 0 | 0 | 0 |
| Ragweed | 0 | 0 | 0 | 0 | 0 | 0 | 0 | 0 | 0 | 0 | 20 | 10 | 10 | 0 | 0 |
| Ryegrass, It. | 0 | 0 | 0 | 0 | 0 | 0 | 0 | 0 | 0 | 0 | 20 | 0 | 0 | 0 | 0 |
| Wheat | 0 | 0 | 0 | 0 | 0 | 0 | 0 | 0 | 0 | 20 | 0 | 0 | 0 | 20 | 0 |

| 125 g ai/ha | Compounds | | | | | | | | | | | | |
|---|---|---|---|---|---|---|---|---|---|---|---|---|---|
| Postemergence | 5 | 6 | 7 | 8 | 9 | 10 | 11 | 12 | 15 | 16 | 17 | 18 | 19 | 20 |
| Barnyardgrass | 0 | 0 | 0 | 0 | 10 | 0 | 0 | 0 | 0 | 40 | 20 | 20 | 0 | 0 |
| Blackgrass | 0 | 0 | 0 | 0 | 0 | 0 | 0 | 0 | 0 | 0 | 0 | 20 | 0 | 0 |
| Corn | 0 | 0 | 0 | 0 | 0 | 0 | 0 | 0 | 0 | 0 | 0 | 0 | 0 | 0 |
| Foxtail, Giant | 0 | 0 | 0 | 0 | 0 | 0 | 0 | 0 | 0 | 20 | 0 | 20 | 0 | 0 |
| *Galium* | 0 | 0 | 0 | 0 | 0 | 0 | 0 | 0 | 0 | 0 | 0 | 0 | 0 | 0 |
| Kochia | 0 | 0 | 0 | 0 | 0 | 0 | 0 | 0 | 0 | 0 | 0 | 0 | 0 | 0 |
| Pigweed | 0 | 0 | 0 | 0 | 0 | 0 | 0 | 0 | 0 | 0 | 0 | 0 | 0 | 0 |
| Ragweed | 0 | 0 | 0 | 0 | 0 | 0 | 0 | 0 | 0 | 0 | 0 | 0 | 0 | 0 |

TABLE A-continued

| | | | | | | | | | | | | | | |
|---|---|---|---|---|---|---|---|---|---|---|---|---|---|---|
| Ryegrass, It. | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 |

| 125 g ai/ha | Compounds | | | | | | | | | | | | | | |
|---|---|---|---|---|---|---|---|---|---|---|---|---|---|---|---|
| Postemergence | 21 | 22 | 23 | 24 | 25 | 26 | 27 | 28 | 29 | 30 | 31 | 32 | 33 | 34 | 35 |
| Barnyardgrass | 0 | 40 | 20 | 0 | 40 | 0 | 0 | 50 | 0 | 50 | 30 | 40 | 50 | 0 | 0 |
| Blackgrass | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 20 | 0 | 0 |
| Foxtail, Giant | 0 | 20 | 20 | 30 | 30 | 0 | 0 | 20 | 0 | 40 | 30 | 20 | 70 | 20 | 0 |
| *Galium* | 0 | 0 | 0 | 0 | 0 | 0 | 0 | 0 | 0 | 0 | 0 | 0 | 0 | 0 | 0 |
| Kochia | 0 | 0 | 0 | — | 0 | 0 | — | 0 | 0 | 0 | 0 | 0 | 0 | 0 | 0 |
| Pigweed | 0 | 0 | 0 | 0 | 0 | 0 | 0 | 0 | 0 | 0 | 0 | 0 | 0 | 0 | 0 |
| Ragweed | 0 | 0 | 0 | 0 | 0 | 0 | 0 | 0 | 0 | 0 | 0 | 0 | 10 | 10 | 0 |
| Ryegrass, It. | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 |

| 1000 g ai/ha | Compounds | | | | | |
|---|---|---|---|---|---|---|
| Preemergence | 1 | 2 | 3 | 4 | 13 | 14 |
| Barnyardgrass | 70 | 30 | 0 | 0 | 80 | 20 |
| Corn | 0 | 0 | 0 | 0 | 0 | 0 |
| Crabgrass | 90 | 90 | 0 | 60 | 80 | 80 |
| Foxtail, Giant | 90 | 80 | 0 | 0 | 60 | 30 |
| Morningglory | 0 | 0 | 0 | 0 | 0 | 0 |
| Pigweed | 0 | 0 | 0 | 0 | 0 | 0 |
| Velvetleaf | 0 | 0 | 0 | 0 | 0 | 0 |
| Wheat | 0 | 0 | 0 | 0 | 0 | 0 |

| 500 g ai/ha | Compounds | | | | | | | | | | | | | |
|---|---|---|---|---|---|---|---|---|---|---|---|---|---|---|
| Preemergence | 5 | 6 | 7 | 8 | 9 | 10 | 11 | 12 | 15 | 16 | 17 | 18 | 19 | 20 |
| Barnyardgrass | 0 | 0 | 40 | 0 | 50 | 0 | 0 | 60 | 0 | 90 | 50 | 30 | 50 | 0 |
| Foxtail, Giant | 0 | 0 | 30 | 50 | 50 | 0 | 0 | 60 | 0 | 90 | 90 | 60 | 20 | 0 |
| Kochia | 0 | 0 | 0 | 0 | 50 | 0 | 0 | 0 | 0 | 0 | 0 | 0 | 0 | 0 |
| Pigweed | 0 | 0 | 0 | 0 | 0 | 0 | 0 | 0 | 0 | 0 | 20 | 0 | 0 | 0 |
| Ragweed | 0 | 0 | 0 | 0 | 30 | 0 | 0 | 0 | 0 | 0 | 0 | — | 0 | 0 |
| Ryegrass, It. | 0 | 0 | 0 | 0 | 0 | 0 | 0 | 0 | 0 | 0 | 0 | 20 | 0 | 0 |

| 500 g ai/ha | Compounds | | | | | | | | | | | | | | |
|---|---|---|---|---|---|---|---|---|---|---|---|---|---|---|---|
| Preemergence | 21 | 22 | 23 | 24 | 25 | 26 | 27 | 28 | 29 | 30 | 31 | 32 | 33 | 34 | 35 |
| Barnyardgrass | 80 | 80 | 80 | 70 | 90 | 70 | 50 | 90 | 70 | 90 | 70 | 60 | 90 | 80 | 30 |
| Foxtail, Giant | 0 | 70 | 80 | 90 | 90 | 70 | 60 | 90 | 60 | 90 | 70 | 80 | 90 | 80 | 60 |
| Kochia | 0 | 20 | 0 | 20 | 60 | 0 | 40 | 0 | 0 | 80 | 20 | 0 | 20 | 0 | 50 |
| Pigweed | 0 | 0 | 0 | 0 | 50 | 40 | 0 | 0 | 0 | 0 | 0 | 0 | 0 | 100 | 0 |
| Ragweed | 0 | 0 | 0 | 30 | 0 | 0 | 30 | 0 | 0 | 0 | 0 | 0 | 0 | 0 | 0 |
| Ryegrass, It. | 20 | 0 | 0 | 0 | 0 | 0 | 20 | 0 | 0 | 0 | 0 | 0 | 0 | 0 | 0 |

| 125 g ai/ha | Compounds | | | | | | | | | | | | | |
|---|---|---|---|---|---|---|---|---|---|---|---|---|---|---|
| Preemergence | 5 | 6 | 7 | 8 | 9 | 10 | 11 | 12 | 15 | 16 | 17 | 18 | 19 | 20 |
| Barnyardgrass | 0 | 0 | 0 | 0 | 0 | 0 | 0 | 0 | 0 | 20 | 20 | 20 | 0 | 0 |
| Foxtail, Giant | 0 | 0 | 0 | 0 | 0 | 0 | 0 | 0 | 0 | 60 | 30 | 50 | 0 | 0 |
| Kochia | 0 | 0 | 0 | 0 | 0 | 0 | 0 | 0 | 0 | 0 | 0 | 0 | 0 | 0 |
| Pigweed | 0 | 0 | 0 | 0 | 0 | 0 | 0 | 0 | 0 | 0 | 0 | 0 | 0 | 0 |
| Ragweed | 0 | 0 | 0 | 0 | 0 | 0 | 0 | 0 | 0 | 0 | 0 | 0 | 0 | 0 |
| Ryegrass, It. | 0 | 0 | 0 | 0 | 0 | 0 | 0 | 0 | 0 | 0 | 0 | 0 | 0 | 0 |

| 125 g ai/ha | Compounds | | | | | | | | | | | | | | |
|---|---|---|---|---|---|---|---|---|---|---|---|---|---|---|---|
| Preemergence | 21 | 22 | 23 | 24 | 25 | 26 | 27 | 28 | 29 | 30 | 31 | 32 | 33 | 34 | 35 |
| Barnyardgrass | 20 | 60 | 60 | 30 | 60 | 0 | 0 | 50 | 30 | 50 | 0 | 20 | 50 | 20 | 0 |
| Foxtail, Giant | 0 | 50 | 40 | 60 | 40 | 0 | 0 | 50 | 0 | 60 | 20 | 0 | 50 | 20 | 0 |
| Kochia | 0 | 0 | 0 | 0 | 0 | 0 | 0 | 0 | 0 | 70 | 0 | 0 | 0 | 0 | 0 |
| Pigweed | 0 | 0 | 0 | 0 | 0 | 0 | 0 | 0 | 0 | 0 | 0 | 0 | 0 | 80 | 0 |
| Ragweed | 0 | 0 | 0 | 0 | 0 | 0 | 0 | 0 | 0 | 0 | 0 | 0 | 0 | 0 | 0 |
| Ryegrass, It. | 0 | 0 | 0 | 0 | 0 | 0 | 0 | 0 | 0 | 0 | 0 | 0 | 0 | 0 | 0 |

Test B

Plant species in the flooded paddy test selected from rice (*Oryza sativa*), sedge, umbrella (small-flower umbrella sedge, *Cyperus difformis*), ducksalad (*Heteranthera limosa*), and barnyardgrass (*Echinochloa crus-galli*) were grown to the 2-leaf stage for testing. At time of treatment, test pots were flooded to 3 cm above the soil surface, treated by application of test compounds directly to the paddy water, and then maintained at that water depth for the duration of the test. Treated plants and controls were maintained in a greenhouse for 13 to 15 d, after which time all species were compared to controls and visually evaluated. Plant response ratings, summarized in Table B, are based on a scale of 0 to 100 where 0 is no effect and 100 is complete control. A dash (-) response means no test result.

TABLE B

| 1000 g ai/ha | Compounds | |
|---|---|---|
| Flood | 1 | 2 |
| Barnyardgrass | 0 | 0 |
| Ducksalad | 50 | 0 |
| Rice | 0 | 0 |
| Sedge, Umbrella | 0 | 0 |

| 250 g ai/ha Flood | Compound 13 |
|---|---|
| Barnyardgrass | 0 |
| Ducksalad | 0 |
| Rice | 0 |
| Sedge, Umbrella | 0 |

| 500 g ai/ha | Compounds | | | | | | | | |
|---|---|---|---|---|---|---|---|---|---|
| Flood | 5 | 6 | 7 | 8 | 9 | 10 | 11 | 12 | 15 |
| Barnyardgrass | 0 | 0 | 25 | 0 | 0 | 0 | 0 | 0 | 0 |
| Ducksalad | 0 | 0 | 75 | 0 | 40 | 0 | 0 | 0 | 70 |
| Rice | 0 | 0 | 0 | 0 | 0 | 0 | 0 | 0 | 0 |
| Sedge, Umbrella | 0 | 0 | 0 | 0 | 0 | 0 | 0 | 0 | 0 |

| 250 g ai/ha | Compounds | | | | | | | | | | | | |
|---|---|---|---|---|---|---|---|---|---|---|---|---|---|
| Flood | 16 | 17 | 18 | 19 | 20 | 21 | 22 | 23 | 24 | 25 | 26 | 27 | 28 |
| Barnyardgrass | 0 | 0 | 30 | 0 | 0 | 0 | 0 | 0 | 70 | 0 | 0 | 0 | 90 |
| Ducksalad | 70 | 70 | 40 | 0 | 50 | 40 | 70 | 0 | 90 | 85 | 75 | 80 | 90 |
| Rice | 0 | 0 | 15 | 0 | 0 | 0 | 0 | 0 | 0 | 20 | 0 | 0 | 10 |
| Sedge, Umbrella | 0 | 0 | 0 | 0 | 0 | 0 | 0 | 0 | 0 | 0 | 0 | 0 | 50 |

| 250 g ai/ha | Compounds | | | | | | |
|---|---|---|---|---|---|---|---|
| Flood | 29 | 30 | 31 | 32 | 33 | 34 | 35 |
| Barnyardgrass | 0 | 70 | 40 | 0 | 40 | 0 | 0 |
| Ducksalad | 75 | 95 | 80 | 70 | 95 | 80 | 70 |
| Rice | 0 | 15 | 15 | 0 | 0 | 15 | 0 |
| Sedge, Umbrella | 0 | 0 | 50 | 0 | 0 | 60 | 0 |

What is claimed is:

1. A compound selected from Formula 1, N oxides and salts thereof,

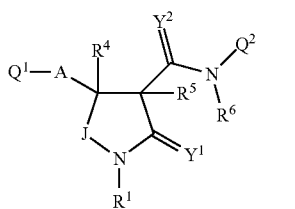

1 wherein

A is a saturated, partially unsaturated or fully unsaturated chain containing 1 to 3 atoms selected from up to 3 carbon, up to 1 O, up to 1 S and up to 2 N atoms, wherein up to 2 carbon members are independently selected from C(=O) and C(=S) and the sulfur atom member is selected from $S(=O)_u(=NR^8)_v$; the said chain optionally substituted with up to 5 substituents independently selected from $R^{15}$ on carbon atoms and $R^{16}$ on nitrogen atoms;

$Q^1$ is a phenyl ring or a naphthalenyl ring system, each ring or ring system optionally substituted with up to 5 substituents independently selected from $R^7$; or a 5- to 6-membered heteroaromatic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^7$ on carbon atom ring members and selected from $R^9$ on nitrogen atom ring members;

$Q^2$ is a phenyl ring or a naphthalenyl ring system, each ring or ring system optionally substituted with up to 5 substituents independently selected from $R^{10}$; or a 5- to 6-membered heteroaromatic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^{10}$ on carbon atom ring members and selected from $R^{11}$ on nitrogen atom ring members;

$Y^1$ and $Y^2$ are each independently O, S or $NR^{12}$;

J is $CR^2R^3$; or $-CR^2R^3-CR^{2a}R^{3a}-$ wherein the $-CR^2R^3-$ moiety is directly connected to N;

$R^1$ is H, hydroxy, amino, cyano, formyl, $C_3$-$C_8$ alkylcarbonylalkyl, $-C(C_1$-$C_4$ alkyl)$=N-O(C_1$-$C_4$ alkyl), $-C(O)NH_2$, $C_1$-$C_6$ alkyl, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkenylalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_5$-$C_{10}$ cycloalkylcarbonylalkyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminoalkyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl; or arylcarbonyl, arylalkenylalkyl, arylcarbonylalkyl or $-CPh=N-O(C_1$-$C_4$ alkyl), each optionally substituted on ring members with up to 5 substituents independently selected from $R^{13}$; or $G^1$;

$R^2$ and $R^3$ are each independently H, halogen, hydroxy, $C_1$-$C_4$ alkyl, $C_1$-$C_4$ haloalkyl or $C_1$-$C_4$ alkoxy; or $R^2$ and $R^3$ are taken together with the carbon atom to which they are bonded to form a $C_3$-$C_7$ cycloalkyl ring;

$R^{2a}$ and $R^{3a}$ are each independently H, halogen or $C_1$-$C_4$ alkyl; or $R^{2a}$ and $R^{3a}$ are taken together with the carbon atom to which they are bonded to form a $C_3$-$C_7$ cycloalkyl ring;

each $R^4$ is independently H, halogen, hydroxy, $C_1$-$C_4$ alkoxy or $C_1$-$C_4$ alkyl;

each $R^5$ is independently H, halogen, hydroxy, $C_1$-$C_4$ alkoxy, cyano or $C_1$-$C_4$ alkyl;

$R^6$ is H, hydroxy, amino, $C_1$-$C_6$ alkyl, $C_1$-$C_6$ haloalkyl, $C_2$-$C_6$ alkenyl, $C_3$-$C_6$ alkynyl, $C_2$-$C_8$ alkoxyalkyl, $C_3$-$C_8$ alkoxyalkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl or $C_3$-$C_{10}$ trialkylsilyl; or $G^1$;

each $R^7$ is independently halogen, hydroxy, cyano, nitro, $C_1$-$C_8$ alkyl, $C_2$-$C_8$ cyanoalkyl, $C_1$-$C_8$ cyanoalkoxy, $C_1$-$C_8$ haloalkyl, $C_2$-$C_8$ alkenyl, $C_2$-$C_8$ haloalkenyl, $C_2$-$C_8$ alkynyl, $C_2$-$C_8$ haloalkynyl, $C_1$-$C_8$ nitroalkyl, $C_2$-$C_8$ nitroalkenyl, $C_2$-$C_8$ alkoxyalkyl, $C_3$-$C_8$ alkoxyalkoxyalkyl, $C_2$-$C_8$ haloalkoxyalkyl, $C_3$-$C_8$ cycloalkyl, $C_3$-$C_8$ halocycloalkyl, $C_4$-$C_{10}$ cycloalkylalkyl, $C_4$-$C_{10}$ alkylcyclolalkyl, $C_1$-$C_8$ alkoxy, $C_1$-$C_8$ haloalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_1$-$C_8$ alkylthio, $C_1$-$C_8$ haloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, hydroxy, formyl, $C_2$-$C_8$ alkylcarbonyl, $C_2$-$C_8$ alkylcarbonyloxy, $C_1$-$C_8$ alkylsulfonyloxy, $C_1$-$C_8$ haloalkylsulfonyloxy, amino, $C_1$-$C_4$ alkylamino, $C_2$-$C_4$ dialkylamino, formylamino, $C_2$-$C_4$ alkylcarbonylamino, $-SF_5$, $-SCN$, $C_4$-$C_{10}$ cycloalkylalkoxy, $C_4$-$C_{10}$ cycloalkylalkyl, $C_2$-$C_8$ alkenyloxy, $C_2$-$C_8$ haloalkenyloxy, $C_2$-$C_8$ alkoxyalkoxy, $C_2$-$C_8$ alkylthioalkyl, $C_2$-$C_8$ alkylsulfinylalkyl, $C_2$-$C_8$ alkylsulfonylalkyl, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_2$-$C_8$ alkynyl, $C_2$-$C_8$ haloalkynyl, $C_2$-$C_8$ alkoxyalkyl, $C_2$-$C_8$ haloalkoxyalkyl, $C_3$-$C_8$ haloalkoxyalkoxy, $C_2$-$C_8$ haloalkoxyhaloalkyl, $C_1$-$C_8$ haloalkyl, $C_3$-$C_8$ halocycloalkyl, $C_2$-$C_8$ alkylcarbonyloxy, $C_2$-$C_8$ haloalkylcarbonyloxy, $C_3$-$C_{12}$ trialkylsilyl, trimethylsilylmethyl or trimethylsilylmethoxy; or $G^2$; or $R^{17}ON=CR^{17a}-$, $(R^{18})_2C=NO-$, $(R^{19})_2NN=CR^{17a}-$, $(R^{18})_2C=NNR^{20a}-$, $R^{20}N=CR^{17a}-$, $(R^{18})_2C=N-$, $R^{17}ON=CR^{17a}C(R^{23b})_2-$ or $(R^{18})_2C=NOC(R^{24a})_2-$, wherein the free bond projecting to the right indicates the connecting point to $Q^1$; or two adjacent $R^7$ are taken together along with the carbon atoms to which they are bonded to form a $C_3$-$C_7$ cycloalkyl ring;

each $R^{10}$ is independently halogen, hydroxy, cyano, nitro, $C_1$-$C_8$ alkyl, $C_2$-$C_8$ cyanoalkyl, $C_1$-$C_8$ cyanoalkoxy, $C_1$-$C_8$ haloalkyl, $C_2$-$C_8$ alkenyl, $C_2$-$C_8$ haloalkenyl, $C_2$-$C_8$ alkynyl, $C_2$-$C_8$ haloalkynyl, $C_1$-$C_8$ nitroalkyl, $C_2$-$C_8$ nitroalkenyl, $C_2$-$C_8$ alkoxyalkyl, $C_3$-$C_8$ alkoxyalkoxyalkyl, $C_2$-$C_8$ haloalkoxyalkyl, $C_3$-$C_8$ cycloalkyl, $C_3$-$C_8$ halocycloalkyl, $C_4$-$C_{10}$ cycloalkylalkyl, $C_4$-$C_{10}$ alkylcyclolalkyl, $C_1$-$C_8$ alkoxy, $C_1$-$C_8$ haloalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_1$-$C_8$ alkylthio, $C_1$-$C_8$ haloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, hydroxy, formyl, $C_2$-$C_8$ alkylcarbonyl, $C_2$-$C_8$ alkylcarbonyloxy, $C_1$-$C_8$ alkylsulfonyloxy, $C_1$-$C_8$ haloalkylsulfonyloxy, amino, $C_1$-$C_4$ alkylamino, $C_2$-$C_4$ dialkylamino, formylamino, $C_2$-$C_4$ alkylcarbonylamino, $-SF_5$, $-SCN$, $C_4$-$C_{10}$ cycloalkylalkoxy, $C_4$-$C_{10}$ cycloalkylalkyl, $C_2$-$C_8$ alkenyloxy, $C_2$-$C_8$ haloalkenyloxy, $C_2$-$C_8$ alkoxyalkoxy, $C_2$-$C_8$ alkylthioalkyl, $C_2$-$C_8$ alkylsulfinylalkyl, $C_2$-$C_8$ alkylsulfonylalkyl, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_2$-$C_8$ alkynyl, $C_2$-$C_8$ haloalkynyl, $C_2$-$C_8$ alkoxyalkyl, $C_2$-$C_8$ haloalkoxyalkyl, $C_3$-$C_8$ haloalkoxyalkoxy, $C_2$-$C_8$ haloalkoxyhaloalkyl, $C_1$-$C_8$ haloalkyl, $C_3$-$C_8$ halocycloalkyl, $C_2$-$C_8$ alkylcarbonyloxy, $C_2$-$C_8$ haloalkylcarbonyloxy, $C_3$-$C_{12}$ trialkylsilyl, trimethylsilylmethyl or trimethylsilylmethoxy; or $G^2$; or $R^{17}ON=CR^{17a}$—, $(R^{18})_2C=NO$—, $(R^{19})_2NN=CR^{17a}$—, $(R^{18})_2C=NNR^{20a}$—, $R^{20}N=CR^{17a}$—, $(R^{18})_2C=N$—, $R^{17}ON=CR^{17a}C(R^{23b})_2$— or $(R^{18})_2C=NOC(R^{24a})_2$—, wherein the free bond projecting to the right indicates the connecting point to $Q^2$; or two adjacent $R^{10}$ are taken together along with the carbon atoms to which they are bonded to form a $C_3$-$C_7$ cycloalkyl ring;

each $R^8$ is independently H, cyano, $C_2$-$C_3$ alkylcarbonyl or $C_2$-$C_3$ haloalkylcarbonyl;

each $R^9$ and $R^{11}$ is independently cyano, $C_1$-$C_3$ alkyl, $C_2$-$C_3$ alkenyl, $C_2$-$C_3$ alkynyl, $C_3$-$C_6$ cycloalkyl, $C_2$-$C_3$ alkoxyalkyl, $C_1$-$C_3$ alkoxy, $C_2$-$C_3$ alkylcarbonyl, $C_2$-$C_3$ alkoxycarbonyl, $C_2$-$C_3$ alkylaminoalkyl or $C_3$-$C_4$ dialkylaminoalkyl;

each $R^{12}$ is independently H, cyano, $C_1$-$C_4$ alkyl, $C_1$-$C_4$ haloalkyl, $C_1$-$C_4$ alkoxy, $C_1$-$C_4$ haloalkoxy, —(C=O)CH$_3$ or —(C=O)CF$_3$;

each $G^1$ is independently phenyl, phenylmethyl, pyridinylmethyl, phenylcarbonyl, phenoxy, phenylethynyl, phenylsulfonyl, phenylcarbonylalkyl, 2-, 3- or 4-pyridinyloxy or a 5- or 6-membered heteroaromatic ring, each optionally substituted on ring members with up to 5 substituents independently selected from $R^{13}$;

each $G^2$ is independently phenyl, phenylmethyl, pyridinylmethyl, phenylcarbonyl, phenylcarbonylalkyl, phenoxy, phenylethynyl, phenylsulfonyl, 2-, 3- or 4-pyridinyloxy or a 5- or 6-membered heteroaromatic ring, each optionally substituted on ring members with up to 5 substituents independently selected from $R^{14}$;

each $R^{13}$ and $R^{14}$ is independently halogen, cyano, hydroxy, amino, nitro, —CHO, —C(=O)OH, —C(=O)NH$_2$, —SO$_2$NH$_2$, $C_1$-$C_6$ alkyl, $C_1$-$C_6$ haloalkyl, $C_2$-$C_6$ alkenyl, $C_2$-$C_6$ alkynyl, $C_2$-$C_8$ alkylcarbonyl, $C_2$-$C_8$ haloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylaminosulfonyl, $C_2$-$C_8$ dialkylaminosulfonyl, $C_3$-$C_{10}$ trialkylsilyl, $C_1$-$C_6$ alkylamino, $C_2$-$C_8$ dialkylamino, $C_2$-$C_8$ alkylcarbonylamino, $C_1$-$C_6$ alkylsulfonylamino, phenyl, pyridinyl or thienyl;

each $R^{15}$ is independently halogen, cyano, hydroxy, $C_1$-$C_4$ alkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl, $C_3$-$C_6$ cycloalkyl or $C_4$-$C_8$ cycloalkylalkyl; or two $R^{15}$ are taken together with the carbon atom or atoms to which they are bonded to form a $C_3$-$C_7$ cycloalkyl ring;

each $R^{16}$ is independently cyano, $C_1$-$C_4$ alkyl, $C_1$-$C_4$ haloalkyl, $C_1$-$C_4$ alkoxy, $C_2$-$C_4$ alkylcarbonyl, $C_2$-$C_4$ alkoxycarbonyl or $C_3$-$C_6$ cycloalkyl;

each $R^{17}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl or $C_3$-$C_{10}$ trialkylsilyl; or $G^1$;

each $R^{17a}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy, $C_1$-$C_6$ alkylthio, $C_1$-$C_6$ haloalkylthio, $C_3$-$C_8$ cycloalkylthio or $C_3$-$C_{10}$ trialkylsilyl; or $G^1$;

each $R^{18}$ is independently H, hydroxy, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl or $C_3$-$C_{10}$ trialkylsilyl; or $G^1$;

each $R^{19}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl or $C_3$-$C_{10}$ trialkylsilyl; or $G^1$;

each $R^{20}$ is independently H, hydroxy, amino, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl or $C_3$-$C_{10}$ trialkylsilyl; or $G^1$;

each $R^{20a}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy or $C_3$-$C_{10}$ trialkylsilyl; or $G^1$;

each $R^{23b}$ is independently H, halogen, cyano, hydroxy, $C_1$-$C_4$ alkyl, $C_3$-$C_8$ cycloalkyl, $C_4$-$C_8$ cycloalkylalkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl or $C_3$-$C_6$ cycloalkyl;

each $R^{24a}$ is independently H, $C_1$-$C_4$ alkyl, $C_3$-$C_8$ cycloalkyl, $C_4$-$C_8$ cycloalkylalkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl or $C_3$-$C_6$ cycloalkyl; and each u and v are independently 0, 1 or 2 in each instance of $S(=O)_u(=NR^8)_v$, provided that the sum of u and v is 0, 1 or 2;

provided when A is S and $Q^1$ is unsubstituted phenyl, $Q^2$ is other than unsubstituted phenyl.

2. The compound of claim 1 wherein
A is —$CH_2$—, —$CH_2O$—, —$CH_2NH$—, —$OCH_2$—, —$NHCH_2$—, —CH=CH—, —C≡C—, —NH— or —O— wherein the free bond projecting to the left indicates the connecting point of A to $Q^1$ and the free bond projecting to the right indicates the connecting point of A to the remainder of Formula 1;
$Q^1$ is a phenyl ring substituted with up to 2 substituents independently selected from $R^7$;
$Q^2$ is a phenyl ring substituted with up to 3 substituents independently selected from $R^{10}$;
$Y^1$ and $Y^2$ are both O; and
J is —$CR^2R^3$—.

3. The compound of claim 1 wherein
A is —$CH_2$—, —$CH_2O$—, —$CH_2NH$—, —$OCH_2$—, —$NHCH_2$—, —CH=CH—, —C≡C—, —NH— or —O— wherein the free bond projecting to the left indicates the connecting point of A to $Q^1$ and the free bond projecting to the right indicates the connecting point of A to the remainder of Formula 1;
$Q^1$ is a phenyl ring substituted with up to 2 substituents independently selected from $R^7$;
$Q^2$ is a phenyl ring substituted with up to 3 substituents independently selected from $R^{10}$;
$Y^1$ and $Y^2$ are both O; and
J is —$CR^2R^3$—$CR^{2a}R^{3a}$.

4. The compound of claim 2 wherein
A is —$CH_2$—;
$R^1$ is H, Me or Et;
$R^2$ is H;
$R^3$ is H;
$R^4$ is H;
$R^5$ is H;
$R^6$ is H;
$R^7$ is independently is independently halogen, cyano, nitro, $C_1$-$C_8$ alkyl, $C_2$-$C_8$ cyanoalkyl, $C_1$-$C_8$ cyanoalkoxy, $C_1$-$C_8$ haloalkyl, $C_2$-$C_8$ alkenyl, $C_2$-$C_8$ haloalkenyl, $C_2$-$C_8$ alkynyl, $C_2$-$C_8$ haloalkynyl, $C_1$-$C_8$ nitroalkyl, $C_2$-$C_8$ nitroalkenyl, $C_2$-$C_8$ alkoxyalkyl, $C_3$-$C_8$ alkoxyalkoxyalkyl, $C_2$-$C_8$ haloalkoxyalkyl, $C_3$-$C_8$ cycloalkyl, $C_3$-$C_8$ halocycloalkyl, $C_4$-$C_{10}$ cycloalkylalkyl, $C_4$-$C_{10}$ alkylcyclolalkyl, $C_1$-$C_8$ alkoxy, $C_1$-$C_8$ haloalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_1$-$C_8$ alkylthio, $C_1$-$C_8$ haloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, hydroxy, formyl, $C_2$-$C_8$ alkylcarbonyl, $C_2$-$C_8$ alkylcarbonyloxy, $C_1$-$C_8$ alkylsulfonyloxy, $C_1$-$C_8$ haloalkylsulfonyloxy, amino, $C_1$-$C_4$ alkylamino, $C_2$-$C_4$ dialkylamino, formylamino, $C_2$-$C_4$ alkylcarbonylamino, —$SF_5$, —SCN, $C_3$-$C_{12}$ trialkylsilyl, trimethylsilylmethyl or trimethylsilylmethoxy; and
$R^{10}$ is independently halogen, cyano, nitro, $C_1$-$C_2$ alkyl, $C_1$-$C_3$ haloalkyl or $C_1$-$C_3$ alkylsulfonyl.

5. The compound of claim 3 wherein
A is —$CH_2$—;
$R^1$ is H, Me or Et;
$R^2$ is H;
$R^3$ is H;
$R^{2a}$ is H;
$R^{3a}$ is H;
$R^4$ is H;
$R^5$ is H;
$R^6$ is H;
$R^7$ is independently is independently halogen, cyano, nitro, $C_1$-$C_8$ alkyl, $C_2$-$C_8$ cyanoalkyl, $C_1$-$C_8$ cyanoalkoxy, $C_1$-$C_8$ haloalkyl, $C_2$-$C_8$ alkenyl, $C_2$-$C_8$ haloalkenyl, $C_2$-$C_8$ alkynyl, $C_2$-$C_8$ haloalkynyl, $C_1$-$C_8$ nitroalkyl, $C_2$-$C_8$ nitroalkenyl, $C_2$-$C_8$ alkoxyalkyl, $C_3$-$C_8$ alkoxyalkoxyalkyl, $C_2$-$C_8$ haloalkoxyalkyl, $C_3$-$C_8$ cycloalkyl, $C_3$-$C_8$ halocycloalkyl, $C_4$-$C_{10}$ cycloalkylalkyl, $C_4$-$C_{10}$ alkylcyclolalkyl, $C_1$-$C_8$ alkoxy, $C_1$-$C_8$ haloalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_1$-$C_8$ alkylthio, $C_1$-$C_8$ haloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, hydroxy, formyl, $C_2$-$C_8$ alkylcarbonyl, $C_2$-$C_8$ alkylcarbonyloxy, $C_1$-$C_8$ alkylsulfonyloxy, $C_1$-$C_8$ haloalkylsulfonyloxy, amino, $C_1$-$C_4$ alkylamino, $C_2$-$C_4$ dialkylamino, formylamino, $C_2$-$C_4$ alkylcarbonylamino, —$SF_5$, —SCN, $C_3$-$C_{12}$ trialkylsilyl, trimethylsilylmethyl or trimethylsilylmethoxy; and
$R^{10}$ is independently halogen, cyano, nitro, $C_1$-$C_2$ alkyl, $C_1$-$C_3$ haloalkyl or $C_1$-$C_3$ alkylsulfonyl.

6. The compound of claim 4 wherein
each $R^7$ is independently halogen, cyano, $C_1$-$C_2$ alkyl, $C_1$-$C_3$ haloalkyl or $C_1$-$C_3$ alkylsulfonyl; and
each $R^{10}$ is independently halogen or $C_1$-$C_2$ haloalkyl.

7. The compound of claim 6 wherein
$Q^1$ is a phenyl ring substituted with 1 substituent independently selected from $R^7$;
$Q^2$ is a phenyl ring having 2 substituents selected from $R^{10}$ and one of the said substituents is at an ortho position and the other said substituent is at meta or para position.

8. The compound of claim 6 wherein
$Q^2$ is a phenyl ring substituted with three substituents selected from $R^{10}$ and the three substituents are at an ortho, meta and para positions of the phenyl ring.

9. The compound of claim 1 wherein
A is selected from —ON=CH—, —ON=C($CH_3$)—, —NHN=CH—, —NHN=C($CH_3$)—, —N=CH—, —N=C($CH_3$)—, —CH=NO—, —C($CH_3$)=NO—, —CH=NNH—, —C($CH_3$)=NNH—, —CH=N—, —C($CH_3$)=N—, —$CH_2CH_2CH_2$—, —$CH_2CH_2$—, —CH$_2$—, —CF$_2$—, —C(=O)—, —CH=CH—, —CH=CHCH$_2$—, —CH$_2$CH=CH—, —C≡—, —C≡CCH$_2$—, —CH$_2$C≡C—, —CH$_2$CH$_2$O—, —O—, —OCH$_2$CH$_2$—, —OCH$_2$—, —CH$_2$CH$_2$S—, —CH$_2$S—, —S—, —SO—, —SO$_2$—, —SCH$_2$CH$_2$—, —SCH$_2$—, —CH$_2$CH$_2$NH—, —CH$_2$NH—, —NH—, —NHCH$_2$— and —NHCH$_2$CH$_2$—, wherein the bond projecting to the left is connected to the Q$^1$ moiety, and the bond projecting to the right is connected to the remainder of Formula 1;

Q$^1$ is a phenyl ring optionally substituted with 1 to 4 substituents independently selected from R$^7$; or a 5- to 6-membered heteroaromatic ring containing ring members selected from carbon atoms and 1 to 4 heteroatoms independently selected from up to 2 O, up to 2 S and up to 4 N atoms, optionally substituted with up to 4 substituents independently selected from R$^7$ on carbon atom ring members and selected from R$^9$ on nitrogen atom ring members;

Q$^2$ is a phenyl ring optionally substituted with up to 5 substituents independently selected from R$^{10}$; or a 5- to 6-membered fully unsaturated heterocyclic ring, each ring containing ring members selected from carbon atoms and 1 to 4 heteroatoms independently selected from up to 2 O, up to 2 S and up to 4 N atoms, each ring or ring system optionally substituted with up to 5 substituents independently selected from R$^{11}$ on carbon atom ring members and selected from R$^{11}$ on nitrogen atom ring members;

Y$^1$ and Y$^2$ are both 0;

R$^1$ is H, hydroxy, amino, cyano, formyl, C$_3$-C$_8$ alkylcarbonylalkyl, —C(C$_1$-C$_4$ alkyl)=N—O(C$_1$-C$_4$ alkyl), —C(O)NH$_2$, C$_1$-C$_6$ alkyl, C$_1$-C$_6$ haloalkyl, C$_2$-C$_6$ alkenyl, C$_3$-C$_6$ alkynyl, C$_2$-C$_6$ cyanoalkyl, C$_3$-C$_6$ cycloalkyl, C$_4$-C$_8$ cycloalkylalkyl, C$_2$-C$_8$ alkoxyalkyl, C$_3$-C$_8$ alkoxyalkoxyalkyl or C$_2$-C$_8$ haloalkoxyalkyl;

R$^6$ is H, hydroxy, amino, C$_1$-C$_6$ alkyl, C$_1$-C$_6$ haloalkyl, C$_2$-C$_6$ alkenyl, C$_3$-C$_6$ alkynyl, C$_2$-C$_8$ alkoxyalkyl, C$_3$-C$_8$ alkoxyalkoxyalkyl or C$_2$-C$_8$ haloalkoxyalkyl;

each R$^7$ is independently halogen, cyano, nitro, C$_1$-C$_8$ alkyl, C$_2$-C$_8$ cyanoalkyl, C$_1$-C$_8$ cyanoalkoxy, C$_1$-C$_8$ haloalkyl, C$_2$-C$_8$ alkenyl, C$_2$-C$_8$ haloalkenyl, C$_2$-C$_8$ alkynyl, C$_2$-C$_8$ haloalkynyl, C$_1$-C$_8$ nitroalkyl, C$_2$-C$_8$ nitroalkenyl, C$_2$-C$_8$ alkoxyalkyl, C$_3$-C$_8$ alkoxyalkoxyalkyl, C$_2$-C$_8$ haloalkoxyalkyl, C$_3$-C$_8$ cycloalkyl, C$_3$-C$_8$ halocycloalkyl, C$_4$-C$_{10}$ cycloalkylalkyl, C$_4$-C$_{10}$ alkylcyclolalkyl, C$_1$-C$_8$ alkoxy, C$_1$-C$_8$ haloalkoxy, C$_2$-C$_8$ alkenyloxy, C$_2$-C$_8$ haloalkenyloxy, C$_3$-C$_8$ alkynyloxy, C$_3$-C$_8$ haloalkynyloxy, C$_3$-C$_8$ cycloalkoxy, C$_1$-C$_8$ alkylthio, C$_1$-C$_8$ haloalkylthio, C$_1$-C$_8$ alkylsulfinyl, C$_1$-C$_8$ haloalkylsulfinyl, C$_1$-C$_8$ alkylsulfonyl, C$_1$-C$_8$ haloalkylsulfonyl, hydroxy, formyl, C$_2$-C$_8$ alkylcarbonyl, C$_2$-C$_8$ alkylcarbonyloxy, C$_1$-C$_8$ alkylsulfonyloxy, C$_1$-C$_8$ haloalkylsulfonyloxy, amino, C$_1$-C$_4$ alkylamino, C$_2$-C$_4$ dialkylamino, formylamino, C$_2$-C$_4$ alkylcarbonylamino, —SF$_5$, —SCN, C$_3$-C$_{12}$ trialkylsilyl, trimethylsilylmethyl or trimethylsilylmethoxy; and each R$^{10}$ is independently halogen, hydroxy, cyano, nitro, C$_1$-C$_8$ alkyl, C$_2$-C$_8$ cyanoalkyl, C$_1$-C$_8$ cyanoalkoxy, C$_1$-C$_8$ haloalkyl, C$_2$-C$_8$ alkenyl, C$_2$-C$_8$ haloalkenyl, C$_2$-C$_8$ alkynyl, C$_2$-C$_8$ haloalkynyl, C$_1$-C$_8$ nitroalkyl, C$_2$-C$_8$ nitroalkenyl, C$_2$-C$_8$ alkoxyalkyl, C$_3$-C$_8$ alkoxyalkoxyalkyl, C$_2$-C$_8$ haloalkoxyalkyl or C$_3$-C$_8$ cycloalkyl.

10. The compound of claim 1 selected from the group consisting of
N-(2,3-difluorophenyl)-4-[(4-fluorophenyl)methyl]-2-oxo-3-pyrrolidinecarboxamide; and
4-[(3-chlorophenyl)methyl]-N-(2,3-difluorophenyl)-2-oxo-3-pyrrolidinecarboxamide.

11. A herbicidal composition comprising a compound of claim 1 and at least one component selected from the group consisting of surfactants, solid diluents and liquid diluents.

12. A herbicidal composition comprising a compound of claim 1, at least one active ingredient selected from the group consisting of herbicides and herbicide safeners, and at least one component selected from the group consisting of surfactants, solid diluents and liquid diluents.

13. A herbicidal mixture comprising (a) a compound of claim 1, and (b) at least one active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solanesyltransferase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, hydantocidin, metam, methyldymron, oleic acid, oxaziclomefone, pelargonic acid and pyributicarba, (b16) herbicide safeners, and salts of compounds of (b1) through (b16).

14. A method for controlling the growth of undesired vegetation comprising contacting the vegetation or its environment with a herbicidally effective amount of a compound of claim 1.

* * * * *